US012167966B2

(12) United States Patent
Deransart et al.

(10) Patent No.: US 12,167,966 B2
(45) Date of Patent: *Dec. 17, 2024

(54) SHOULDER PROSTHESIS COMPONENTS AND ASSEMBLIES

(71) Applicant: HOWMEDICA OSTEONICS CORP., Mahwah, NJ (US)

(72) Inventors: Pierric Deransart, Saint Martin d'uriage (FR); Christopher K. Bade, Missoula, MT (US); William J. Slone, Silver Lake, IN (US); Robert J. Ball, West Olive, MI (US); Gilles Walch, Lyons (FR); Pascal Boileau, Nice (FR); George S. Athwal, London (CA); Jon JP Warner, Weston, MA (US); Robert Z. Tashjian, Salt Lake City, UT (US); Jay D. Keener, St. Louis, MO (US); Shawn M. Gargac, Fort Wayne, IN (US); Austin Wyatt Mutchler, Warsaw, IN (US); David R. Stump, Columbia City, IN (US); Alexander Paul Wolfe, Fort Wayne, IN (US); Kevin P. Knox, Fort Wayne, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/664,435

(22) Filed: May 23, 2022

(65) Prior Publication Data
US 2022/0273451 A1 Sep. 1, 2022

Related U.S. Application Data

(63) Continuation of application No. 17/250,964, filed as application No. PCT/US2019/054005 on Oct. 1, 2019, now Pat. No. 11,364,127.

(Continued)

(51) Int. Cl.
A61F 2/40 (2006.01)
A61F 2/30 (2006.01)
(52) U.S. Cl.
CPC ........ *A61F 2/4014* (2013.01); *A61F 2/30749* (2013.01); *A61F 2/30771* (2013.01);
(Continued)
(58) Field of Classification Search
CPC ................. A61F 2/4003; A61F 2/4014; A61F 2002/4007; A61F 2002/4022;
(Continued)

(56) References Cited

U.S. PATENT DOCUMENTS

| 448,126 A | 3/1891 | Craig |
| 1,065,456 A | 6/1913 | Lowrey |

(Continued)

FOREIGN PATENT DOCUMENTS

| CA | 211530 | 5/2022 |
| CN | 202051851 U | 11/2011 |

(Continued)

OTHER PUBLICATIONS

First Office Action issued in connection with Japanese Patent Application No. 2022-520122, Apr. 18, 2023, 4 pages.

(Continued)

*Primary Examiner* — Megan Y Wolf
(74) *Attorney, Agent, or Firm* — DUANE MORRIS LLP

(57) ABSTRACT

Various embodiments disclosed herein relate to stemmed and stemless humeral anchors for use in shoulder arthroplasty procedures. For example, the humeral anchor can include a first end, a second end, and an interior surface extending between the first end and the second end. The interior surface can be disposed about a recess disposed between the first end and the second end. The recess can be (Continued)

configured to secure a coupling of a shoulder articular body directly to the interior surface.

14 Claims, 37 Drawing Sheets

Related U.S. Application Data

(60) Provisional application No. 62/740,333, filed on Oct. 2, 2018.

(52) U.S. Cl.
CPC ... *A61F 2/4003* (2013.01); *A61F 2002/30011* (2013.01); *A61F 2002/30224* (2013.01); *A61F 2002/30383* (2013.01); *A61F 2002/30428* (2013.01); *A61F 2002/30495* (2013.01); *A61F 2002/30607* (2013.01); *A61F 2002/30884* (2013.01); *A61F 2002/4022* (2013.01)

(58) Field of Classification Search
CPC .. A61F 2002/30214; A61F 2002/30215; A61F 2002/30385; A61F 2002/30403; A61F 2002/30428
See application file for complete search history.

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,601,289 A | 7/1986 | Chiarizzio et al. |
| 4,623,353 A | 11/1986 | Buechel et al. |
| 4,632,111 A | 12/1986 | Roche |
| 4,743,262 A | 5/1988 | Tronzo |
| D296,714 S | 7/1988 | Averill et al. |
| 4,865,605 A | 9/1989 | Dines et al. |
| 4,883,491 A | 11/1989 | Mallory et al. |
| 4,919,670 A | 4/1990 | Dale et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,257,995 A | 11/1993 | Umber et al. |
| 5,282,865 A | 2/1994 | Dong |
| 5,358,526 A | 10/1994 | Tornier |
| 5,383,938 A * | 1/1995 | Rohr ............... F16B 21/183 623/22.29 |
| 5,443,471 A | 8/1995 | Swajger |
| 5,489,309 A | 2/1996 | Lackey et al. |
| 5,489,310 A | 2/1996 | Mikhail |
| 5,507,817 A | 4/1996 | Craig et al. |
| 5,514,136 A | 5/1996 | Richelsoph |
| 5,534,006 A | 7/1996 | Szabo et al. |
| 5,540,697 A | 7/1996 | Rehmann et al. |
| 5,681,134 A | 10/1997 | Ebert |
| 5,702,486 A | 12/1997 | Craig et al. |
| 5,720,750 A | 2/1998 | Koller et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,849,015 A | 12/1998 | Haywood et al. |
| 5,954,727 A | 9/1999 | Collazo |
| 5,976,148 A | 11/1999 | Charpenet et al. |
| 6,045,582 A | 4/2000 | Prybyla |
| 6,063,124 A | 5/2000 | Amstutz |
| 6,099,214 A | 8/2000 | Lee et al. |
| 6,110,179 A | 8/2000 | Flivik et al. |
| 6,113,605 A | 9/2000 | Storer |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,322,564 B1 | 11/2001 | Surma |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Okun et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,626,913 B1 | 9/2003 | McKinnon et al. |
| 6,666,874 B2 | 12/2003 | Heitzmann et al. |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,208,222 B2 | 4/2007 | Rolfe et al. |
| 7,344,565 B2 | 3/2008 | Seyer et al. |
| 7,465,319 B2 | 12/2008 | Tornier |
| 7,476,228 B2 | 1/2009 | Abou |
| 7,476,253 B1 | 1/2009 | Craig et al. |
| 7,585,327 B2 | 9/2009 | Winslow |
| 7,615,080 B2 | 11/2009 | Ondrla |
| 7,637,703 B2 | 12/2009 | Khangar et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,758,650 B2 | 7/2010 | Dews et al. |
| 7,887,544 B2 | 2/2011 | Tornier et al. |
| 7,927,376 B2 | 4/2011 | Leisinger et al. |
| D643,926 S | 8/2011 | Collins |
| 8,021,370 B2 | 9/2011 | Fenton et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,221,037 B2 | 7/2012 | Neitzell |
| 8,231,682 B2 | 7/2012 | LaFosse |
| 8,246,687 B2 | 8/2012 | Katrana et al. |
| 8,262,667 B1 | 9/2012 | Silver et al. |
| D668,331 S | 10/2012 | Ren et al. |
| 8,277,512 B2 | 10/2012 | Parrott et al. |
| 8,317,871 B2 | 11/2012 | Stone et al. |
| 8,409,798 B2 | 4/2013 | Luy et al. |

(56) References Cited

U.S. PATENT DOCUMENTS

| | | |
|---|---|---|
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| D691,710 S | 10/2013 | White |
| 8,591,592 B2 | 11/2013 | Dreyfuss |
| 8,641,773 B2 | 2/2014 | Bergin et al. |
| 8,647,387 B2 | 2/2014 | Winslow |
| 8,663,334 B2 | 3/2014 | Viscardi et al. |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,795,379 B2 | 8/2014 | Smith et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| 8,992,623 B2 | 3/2015 | Hopkins et al. |
| D745,678 S | 12/2015 | Courtney et al. |
| 9,233,003 B2 | 1/2016 | Roche et al. |
| 9,241,804 B2 | 1/2016 | Iannotti |
| 9,289,218 B2 | 3/2016 | Courtney, Jr. et al. |
| 9,326,865 B2 | 5/2016 | Katrana et al. |
| 9,364,334 B2 | 6/2016 | Katrana et al. |
| 9,498,345 B2 | 11/2016 | Burkhead et al. |
| 9,510,839 B2 | 12/2016 | Maroney et al. |
| 9,510,951 B2 | 12/2016 | Bachmaier |
| 9,603,712 B2 | 3/2017 | Bachmaier |
| 9,610,165 B2 | 4/2017 | Poncet et al. |
| 9,615,928 B2 | 4/2017 | Visser et al. |
| 9,820,859 B2 | 11/2017 | Gervasi et al. |
| 9,956,083 B2 | 5/2018 | Humphrey |
| D831,218 S | 10/2018 | da Costa |
| 10,166,032 B2 | 1/2019 | Stone et al. |
| D840,539 S | 2/2019 | Courtney et al. |
| 10,335,285 B2 | 7/2019 | Viscardi et al. |
| 10,368,999 B2 | 8/2019 | Greiwe |
| 10,433,969 B2 | 10/2019 | Humphrey |
| 10,456,264 B2 | 10/2019 | Hodorek et al. |
| 10,463,499 B2 | 11/2019 | Emerick et al. |
| D875,936 S | 2/2020 | Martin |
| 10,722,373 B2 | 7/2020 | Hodorek et al. |
| 10,898,348 B2 | 1/2021 | Vivanz et al. |
| 10,945,862 B2 | 3/2021 | Roby et al. |
| 11,076,962 B2 | 8/2021 | Kemp et al. |
| D938,034 S | 12/2021 | Knox et al. |
| 11,229,524 B2 | 1/2022 | Sperling |
| D951,449 S | 5/2022 | Knox et al. |
| D952,143 S | 5/2022 | Conklin |
| 11,364,127 B2* | 6/2022 | Deransart ............ A61F 2/4003 |
| D983,372 S | 4/2023 | Knox et al. |
| D985,125 S | 5/2023 | Knox et al. |
| 2001/0034553 A1 | 10/2001 | Michelson |
| 2001/0047210 A1 | 11/2001 | Wolf |
| 2001/0049561 A1 | 12/2001 | Dews et al. |
| 2002/0116007 A1 | 8/2002 | Lewis |
| 2002/0156534 A1 | 10/2002 | Grusin et al. |
| 2003/0028253 A1 | 2/2003 | Stone et al. |
| 2003/0031521 A1 | 2/2003 | Haughton et al. |
| 2003/0114933 A1 | 6/2003 | Bouttens et al. |
| 2003/0125810 A1 | 7/2003 | Sullivan et al. |
| 2004/0010262 A1 | 1/2004 | Parkinson et al. |
| 2004/0049270 A1 | 3/2004 | Gewirtz |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0225367 A1 | 11/2004 | Glien et al. |
| 2004/0243136 A1 | 12/2004 | Gupta et al. |
| 2004/0254646 A1 | 12/2004 | Stone et al. |
| 2005/0107882 A1 | 5/2005 | Stone et al. |
| 2005/0112397 A1 | 5/2005 | Rolfe et al. |
| 2005/0203539 A1 | 9/2005 | Grimm et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0064173 A1 | 3/2006 | Guederian |
| 2006/0079963 A1 | 4/2006 | Hansen |
| 2006/0089656 A1 | 4/2006 | Allard et al. |
| 2006/0142866 A1 | 6/2006 | Baratz et al. |
| 2006/0195105 A1 | 8/2006 | Teeny et al. |
| 2006/0200165 A1 | 9/2006 | Tulkis |
| 2006/0200249 A1 | 9/2006 | Beguin et al. |
| 2007/0010825 A1 | 1/2007 | Leisinger et al. |
| 2007/0055380 A1 | 3/2007 | Berelsman et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162038 A1 | 7/2007 | Tuke |
| 2007/0162141 A1 | 7/2007 | Dews et al. |
| 2007/0173945 A1 | 7/2007 | Wiley et al. |
| 2007/0025817 A1 | 9/2007 | Reubelt et al. |
| 2007/0212179 A1 | 9/2007 | Khangar et al. |
| 2007/0219562 A1 | 9/2007 | Slone et al. |
| 2007/0219638 A1 | 9/2007 | Jones et al. |
| 2007/0233132 A1 | 10/2007 | Valla |
| 2007/0288096 A1 | 12/2007 | Surma |
| 2008/0004711 A1 | 1/2008 | Li et al. |
| 2008/0021564 A1 | 1/2008 | Gunther |
| 2008/0077146 A1 | 3/2008 | Pernsteiner et al. |
| 2008/0172061 A1 | 7/2008 | Ragbir |
| 2008/0177393 A1 | 7/2008 | Grant et al. |
| 2008/0195111 A1 | 8/2008 | Anderson |
| 2008/0221576 A1 | 9/2008 | Keller |
| 2008/0228281 A1 | 9/2008 | Forrer et al. |
| 2008/0249577 A1 | 10/2008 | Dreyfuss |
| 2009/0099662 A1 | 4/2009 | Splieth et al. |
| 2009/0171462 A1 | 7/2009 | Poncet et al. |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0087927 A1 | 4/2010 | Roche et al. |
| 2010/0114326 A1 | 5/2010 | Winslow et al. |
| 2010/0121331 A1 | 5/2010 | Sharp et al. |
| 2010/0191340 A1 | 7/2010 | Dreyfuss |
| 2010/0268238 A1 | 10/2010 | Sikora et al. |
| 2010/0274359 A1 | 10/2010 | Brunnarius et al. |
| 2010/0274360 A1 | 10/2010 | Gunther |
| 2010/0278601 A1 | 11/2010 | Beynon |
| 2010/0331902 A1 | 12/2010 | Biegun |
| 2011/0082587 A1 | 4/2011 | Ziaei et al. |
| 2011/0153023 A1 | 6/2011 | Deffenbaugh et al. |
| 2011/0224673 A1 | 9/2011 | Smith |
| 2011/0276144 A1 | 11/2011 | Wirth et al. |
| 2011/0313533 A1 | 12/2011 | Gunther |
| 2012/0022664 A1 | 1/2012 | Vandermeulen et al. |
| 2012/0071985 A1 | 3/2012 | Hodorek et al. |
| 2012/0083769 A1 | 4/2012 | Burgi et al. |
| 2012/0109321 A1 | 5/2012 | Stone et al. |
| 2012/0184964 A1 | 7/2012 | Hudak, Jr. |
| 2012/0221111 A1 | 8/2012 | Burkhead, Jr. et al. |
| 2012/0232562 A1 | 9/2012 | Mani et al. |
| 2012/0265315 A1 | 10/2012 | Kusogullari et al. |
| 2012/0265319 A1 | 10/2012 | Prybyla et al. |
| 2012/0277880 A1 | 11/2012 | Winslow et al. |
| 2012/0290099 A1 | 11/2012 | Gibson et al. |
| 2012/0296435 A1 | 11/2012 | Ambacher |
| 2013/0018382 A1 | 1/2013 | Jones et al. |
| 2013/0018476 A1 | 1/2013 | Katrana et al. |
| 2013/0123929 A1 | 5/2013 | McDaniel et al. |
| 2013/0123930 A1 | 5/2013 | Burt |
| 2013/0150972 A1 | 6/2013 | Iannotti et al. |
| 2013/0173006 A1 | 7/2013 | Duport |
| 2013/0178943 A1 | 7/2013 | Duport |
| 2013/0190882 A1 | 7/2013 | Humphrey |
| 2013/0211539 A1 | 8/2013 | McDaniel et al. |

(56) References Cited

U.S. PATENT DOCUMENTS

| | | |
|---|---|---|
| 2013/0261626 A1 | 10/2013 | Chavarria et al. |
| 2013/0261629 A1 | 10/2013 | Anthony et al. |
| 2013/0261630 A1 | 10/2013 | Courtney, Jr. et al. |
| 2013/0261754 A1 | 10/2013 | Anthony et al. |
| 2013/0261755 A1 | 10/2013 | Anthony et al. |
| 2013/0282129 A1 | 10/2013 | Phipps |
| 2013/0331849 A1 | 12/2013 | Splieth et al. |
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0074246 A1 | 3/2014 | Huebner et al. |
| 2014/0081270 A1 | 3/2014 | Klotz et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257499 A1 | 9/2014 | Winslow et al. |
| 2014/0288657 A1 | 9/2014 | Lederman et al. |
| 2014/0296988 A1 | 10/2014 | Winslow et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0134066 A1 | 5/2015 | Bachmaier |
| 2015/0250601 A1 | 9/2015 | Humphrey |
| 2015/0265411 A1 | 9/2015 | Deransart et al. |
| 2015/0289984 A1 | 10/2015 | Budge |
| 2015/0297354 A1 | 10/2015 | Walch et al. |
| 2015/0328015 A1 | 11/2015 | Olson et al. |
| 2016/0051367 A1 | 2/2016 | Gervasi et al. |
| 2016/0059403 A1 | 3/2016 | Mugnier |
| 2016/0157911 A1 | 6/2016 | Courtney, Jr. et al. |
| 2016/0206445 A1 | 7/2016 | Gheevarughese et al. |
| 2016/0324648 A1 | 11/2016 | Hodorek et al. |
| 2016/0331551 A1 | 11/2016 | Slade et al. |
| 2016/0374815 A1 | 12/2016 | Siccardi et al. |
| 2017/0056187 A1 | 3/2017 | Humphrey et al. |
| 2017/0105843 A1 | 4/2017 | Britton et al. |
| 2017/0112634 A1 | 4/2017 | Gunn et al. |
| 2017/0273800 A1 | 9/2017 | Emerick et al. |
| 2017/0304063 A1 | 10/2017 | Hatzidakis et al. |
| 2017/0367714 A1 | 12/2017 | McCulloch et al. |
| 2017/0367836 A1 | 12/2017 | Cardon et al. |
| 2018/0028249 A1 | 2/2018 | Jaumard |
| 2018/0092757 A1 | 4/2018 | Behzadi et al. |
| 2018/0092760 A1 | 4/2018 | Sperling et al. |
| 2018/0103967 A1 | 4/2018 | Rouyer et al. |
| 2018/0161176 A1 | 6/2018 | Vivanz et al. |
| 2018/0193168 A1 | 7/2018 | Termanini et al. |
| 2018/0200067 A1 | 7/2018 | Axelson et al. |
| 2018/0206859 A1 | 7/2018 | Pendleton et al. |
| 2018/0271667 A1 | 9/2018 | Kemp et al. |
| 2018/0271668 A1 | 9/2018 | Kemp et al. |
| 2018/0280152 A1 | 10/2018 | Mutchler et al. |
| 2019/0105165 A1 | 4/2019 | Sikora et al. |
| 2019/0105169 A1 | 4/2019 | Sperling |
| 2019/0159906 A1 | 5/2019 | Knox et al. |
| 2019/0175354 A1 | 6/2019 | Knox et al. |
| 2019/0216518 A1 | 7/2019 | Courtney, Jr. et al. |
| 2019/0231544 A1 | 8/2019 | Boileau et al. |
| 2019/0231558 A1 | 8/2019 | Beck et al. |
| 2019/0328536 A1 | 10/2019 | Martin et al. |
| 2019/0336307 A1 | 11/2019 | Sungu et al. |
| 2019/0374349 A1 | 12/2019 | Müller |
| 2020/0000573 A1 | 1/2020 | Whittaker et al. |
| 2020/0008947 A1 | 1/2020 | Emerick et al. |
| 2020/0121474 A1 | 4/2020 | Pendleton et al. |
| 2020/0188123 A1 | 6/2020 | Hodorek et al. |
| 2020/0188125 A1 | 6/2020 | Hodorek et al. |
| 2020/0214845 A1 | 7/2020 | Knox et al. |
| 2020/0214853 A1 | 7/2020 | Sweitzer |
| 2020/0222205 A1 | 7/2020 | Gosik-Wolfe et al. |
| 2021/0030565 A1 | 2/2021 | Dun et al. |
| 2021/0045895 A1 | 2/2021 | Sapio et al. |
| 2021/0077264 A1 | 3/2021 | Hodorek et al. |
| 2021/0212840 A1 | 7/2021 | Sweitzer et al. |
| 2021/0212841 A1 | 7/2021 | Sweitzer et al. |
| 2021/0228362 A1 | 7/2021 | Whitwell et al. |
| 2021/0228370 A1 | 7/2021 | Ek et al. |
| 2021/0228372 A1 | 7/2021 | Knox et al. |
| 2021/0244487 A1 | 8/2021 | Beck |
| 2021/0251643 A1 | 8/2021 | Stump |
| 2021/0290411 A1 | 9/2021 | Gosik-Wolfe |
| 2021/0315713 A1 | 10/2021 | Keach et al. |
| 2021/0330476 A1 | 10/2021 | Alden |
| 2021/0338456 A1 | 11/2021 | Wolfe et al. |
| 2021/0386558 A1 | 12/2021 | Alden |
| 2021/0393414 A1 | 12/2021 | Robicheaux et al. |
| 2022/0023053 A1 | 1/2022 | Kim et al. |
| 2022/0023071 A1 | 1/2022 | Sweitzer |
| 2022/0031464 A1 | 2/2022 | Knox et al. |
| 2022/0039811 A1 | 2/2022 | Bahk |
| 2022/0104835 A1 | 4/2022 | Blaser et al. |
| 2022/0117756 A1 | 4/2022 | Blaser et al. |
| 2022/0125591 A1 | 4/2022 | Rivera, Jr. |
| 2022/0151794 A1 | 5/2022 | Fattori et al. |
| 2022/0233322 A1 | 7/2022 | Knox et al. |
| 2023/0145300 A1 | 5/2023 | Paterson et al. |
| 2023/0149177 A1 | 5/2023 | Hodorek et al. |

FOREIGN PATENT DOCUMENTS

| | | |
|---|---|---|
| DE | 4220217 | 12/1993 |
| DE | 10233204 | 1/2004 |
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 952 788 | 8/2008 |
| EP | 1 867 303 | 9/2010 |
| EP | 1 977 720 | 1/2011 |
| EP | 1 550 420 | 2/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2586387 A1 | 5/2013 |
| EP | 2 616 013 | 7/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 12/2014 |
| EP | 2 353 549 | 6/2016 |
| EP | 3 117 801 | 1/2017 |
| EP | 2 965 720 B1 | 7/2017 |
| FR | 2 674 122 | 9/1992 |
| FR | 2980685 B1 | 10/2013 |
| FR | 2997290 B1 | 11/2015 |
| GB | 2405346 | 3/2005 |
| JP | 2002506361 A | 2/2002 |
| JP | 2005511243 A | 4/2005 |
| JP | 2009523578 A | 6/2009 |
| JP | 2015532863 A | 11/2015 |
| JP | 2016528956 A | 9/2016 |
| JP | 2019506281 A | 3/2019 |
| WO | WO 01/67988 | 9/2001 |
| WO | WO 02/17822 | 3/2002 |
| WO | WO 2008/011078 | 1/2008 |
| WO | WO 2008/146124 | 12/2008 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |
| WO | WO 2014/058314 | 4/2014 |
| WO | WO 2015/112307 | 7/2015 |
| WO | 2016094739 A1 | 6/2016 |

(56) References Cited

FOREIGN PATENT DOCUMENTS

| WO | WO 2016/094739 | 6/2016 |
|---|---|---|
| WO | WO 2017/165090 | 9/2017 |
| WO | WO 2017/184792 | 10/2017 |
| WO | WO 2018/022227 | 2/2018 |
| WO | WO 2019/060780 | 3/2019 |
| WO | WO 2019/106278 | 6/2019 |
| WO | 2019133905 A1 | 7/2019 |

OTHER PUBLICATIONS

First Examination Report issued in connection with Australian Patent Application No. 2020360410, Nov. 24, 2022, 5 pages.
Final Office Action issued in connection with Japanese Patent Application No. 2022-520122, Sep. 26, 2023, 3 pages.
Non-Final Office Action issued in connection with U.S. Appl. No. 17/281,683, filed Oct. 6, 2023, 7 pages.
Office Action issued in connection with Japanese Patent Application No. 2021-518159, May 24, 2022, 5 pages.
Third Examination Report issued in connection with Australian Patent Application No. 2019355854, May 10, 2022, 4 pages.
First Examination Report issued in connection with Australian Patent Application No. 2021250994, Jun. 2, 2022, 5 pages.
Non-Final Office Action issued in connection with U.S. Appl. No. 17/717,253, filed Jun. 29, 2022, 56 pages.
Office Action issued in connection with Japanese Patent Application No. 2021-518174, May 24, 2022, 7 pages.
Notice of Allowance issued in connection with U.S. Appl. No. 18/150,254, filed Mar. 20, 2024, 11 pages.
Non-Final Office Action issued in connection with U.S. Appl. No. 18/448,494, filed Mar. 19, 2024, 15 pages.
Barth, et al., "Is global humeral head offset related to intramedullary canal width? A computer tomography morphometric study," Journal of Experimental Orthopaedics, 2018, vol. 5, pp. 1-8.
Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.
Routman, et al., "Reverse Shoulder Arthroplasty Prosthesis Design Classification System," Bulletin of the Hospital for Joint Diseases, 2015, vol. 73 (Suppl 1), pp. S5-S14.
International Search Report and Written Opinion for PCT/US2018/052294 mailed Apr. 4, 2019 in 13 pages.
Non-Final Office Action issued in connection with U.S. Appl. No. 16/648,128, filed Mar. 28, 2022, 15 pages.
First Office Action issued in connection with Japanese Patent Application No. 2019-555151, Feb. 21, 2022, 5 pages.
Non-Final Office Action issued in connection with U.S. Appl. No. 16/519,937, filed Aug. 17, 2021, 21 pages.
Final Rejection issued in connection with U.S. Appl. No. 16/249,720, filed Aug. 20, 2021, 40 pages.
Final Rejection issued in connection with U.S. Appl. No. 16/580,367, filed Aug. 24, 2021, 9 pages.
Office Action issued in connection with Canadian Patent Application No. 3,114,804, May 25, 2021, 7 pages.
First Examination Report issued in connection with Australian Patent Application No. 2019352591, May 19, 2021, 4 pages.
International Search Report and Written Opinion issued in connection with corresponding International Patent Application No. PCT/US2019/054005, Oct. 1, 2019, 21 pages.
Non-Final Office Action issued in connection with U.S. Appl. No. 17/634,623, 11 pages, filed Apr. 30, 2024.
Med Gadget, "Tornier Announces First Implant in U.S. Trial of Its Simpliciti Stemless Shoulder Joint Replacement System", first available Aug. 5, 2011. (https:/Avwww.medgadget.com/2011/08/tornier-announces-first-implant-in-u-s-trial-of-its-simpliciti-stemless-shoulder-joint-replacement-system.html) (Year: 2011).
Wright Media, "Tornier Aequalis Reversed FX", first available May 19, 2016. (https:/Awww.wrightemedia.com/ProductFiles/Files/PDFs/ CAW-1146_EN_LR_LE.pdf) (Year: 2016).
Wright Media, "Aequalis Ascend Flex", first available Jul. 30, 2019. (https:/Awww.wrightemedia.com/ProductFiles/Files/PDFs/AP-010187_EN_LR_LE.pdf) (Year: 2019).
Arthrex, "Univers Revers Shoulder System", first available Apr. 24, 2019. (https:/Awww.arthrex.com/resources/surgical-technique-guide/ qkv6M00_50qt2QFBx1PKnA/univers-revers-shoulder-system) (Year: 2019).
First Office Action issued in connection with Chinese Patent Application No. 202080069828.6, Aug. 15, 2024, 9 pages.

\* cited by examiner

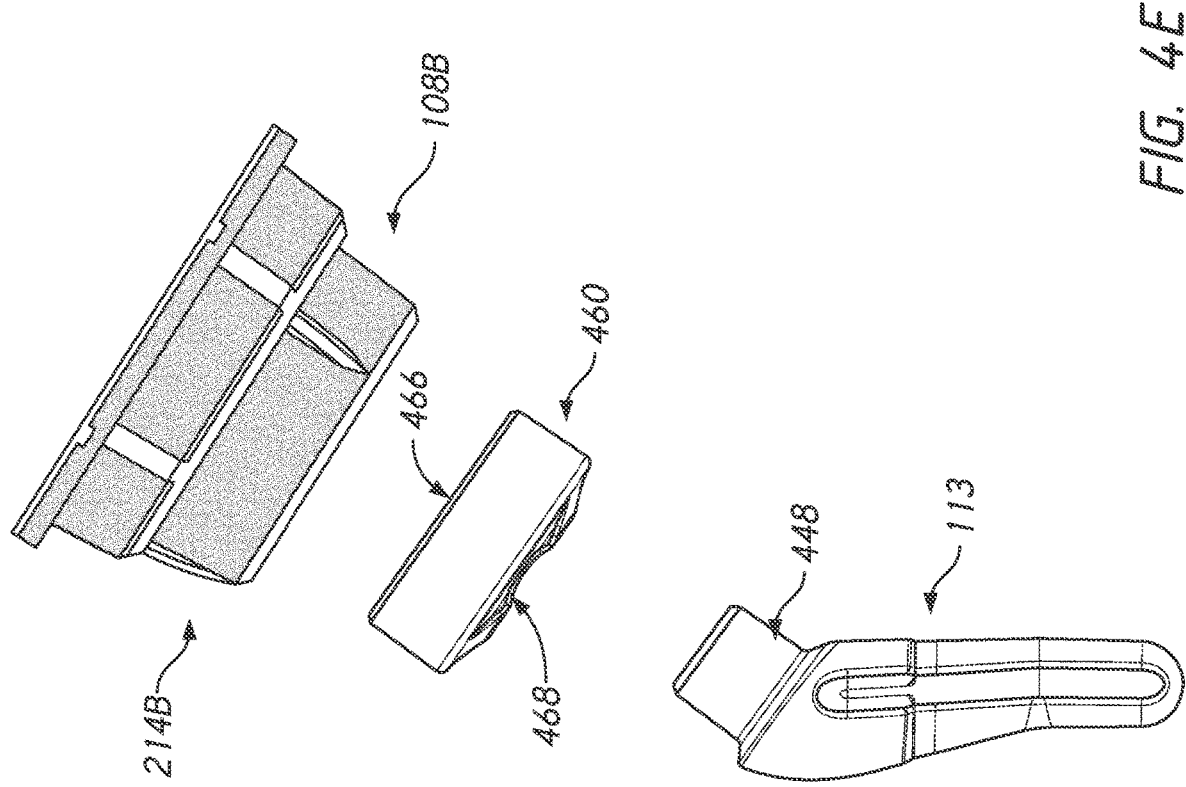

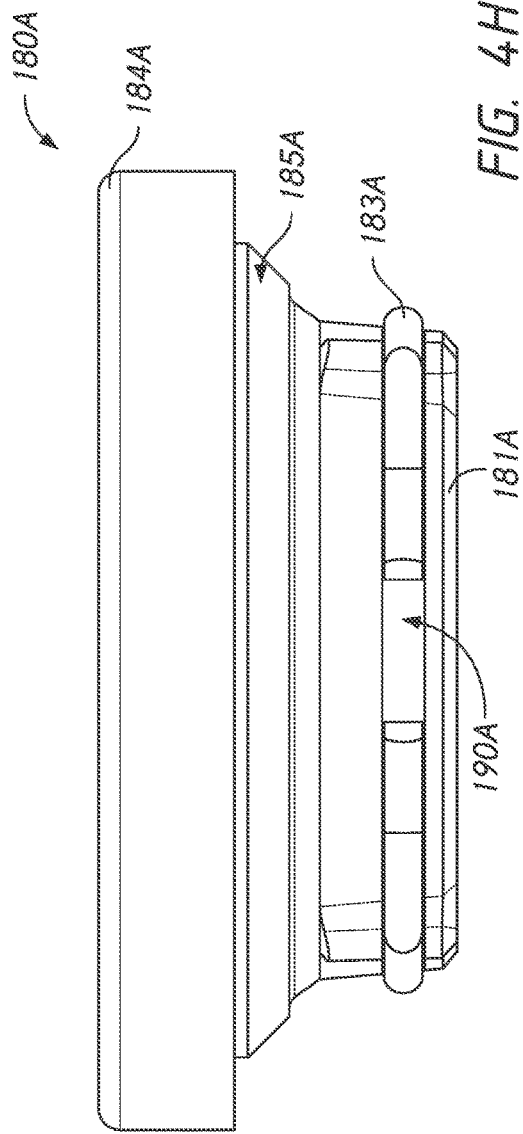
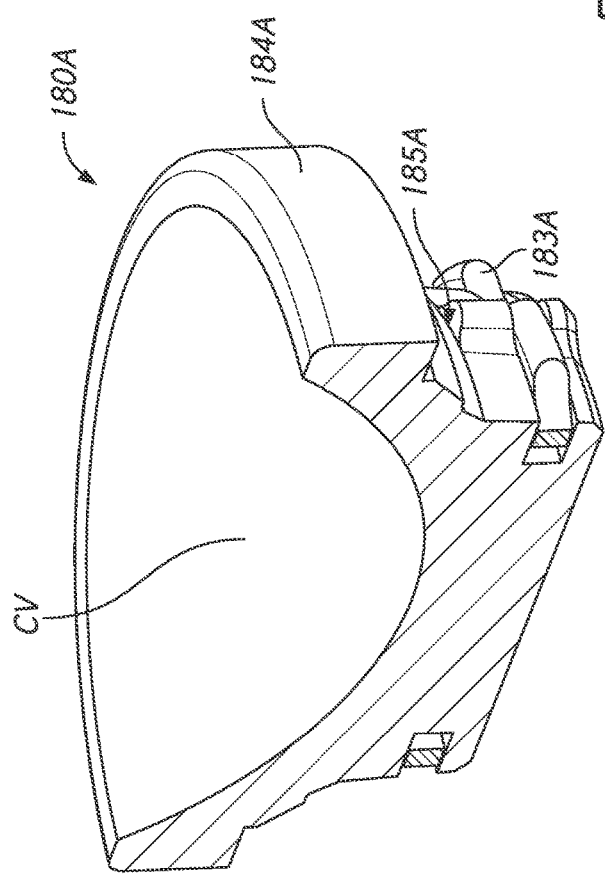
FIG. 4H
FIG. 4I

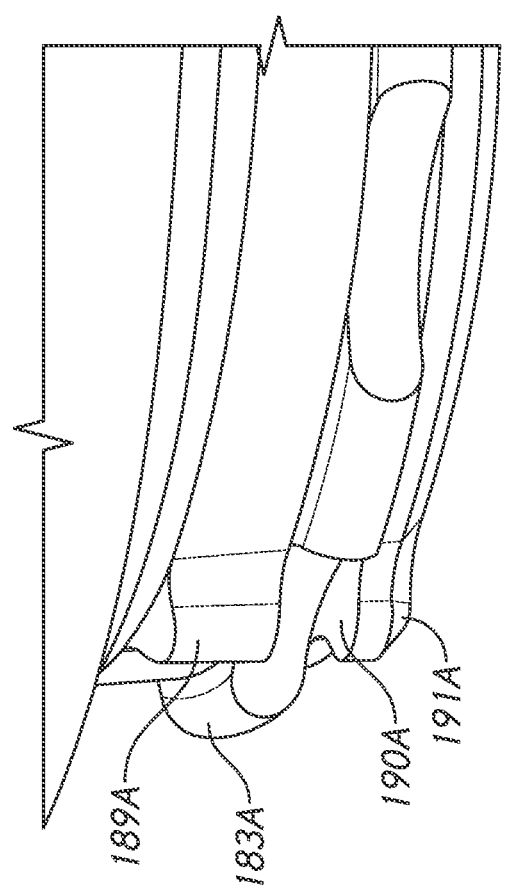

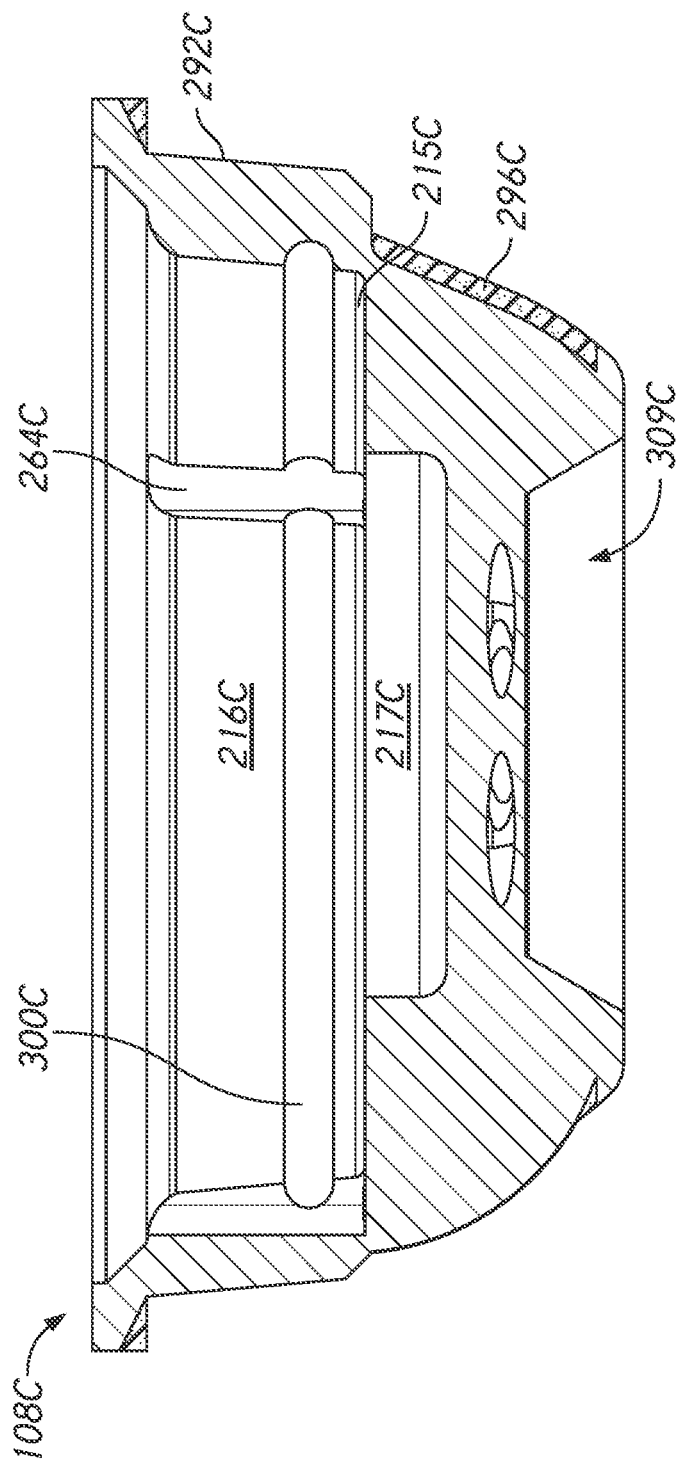

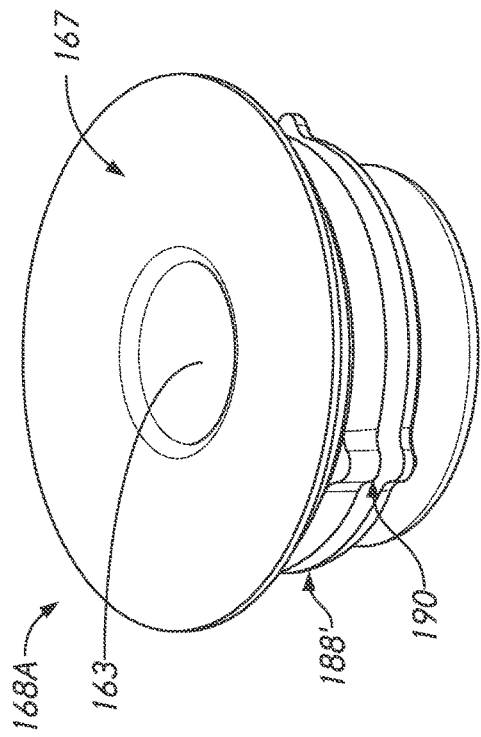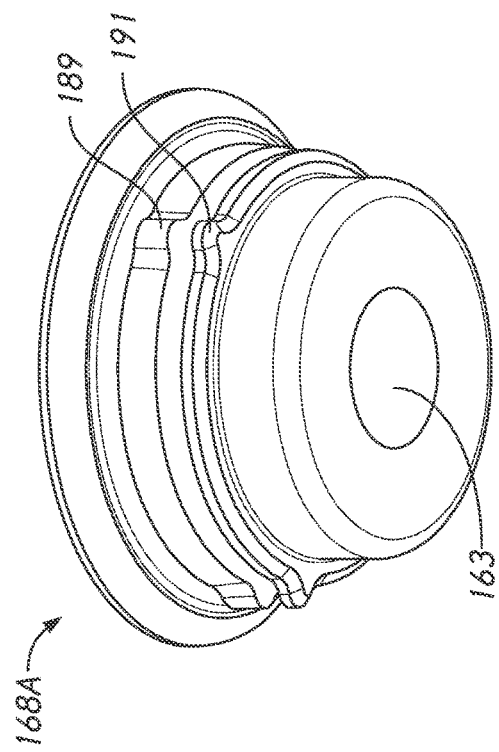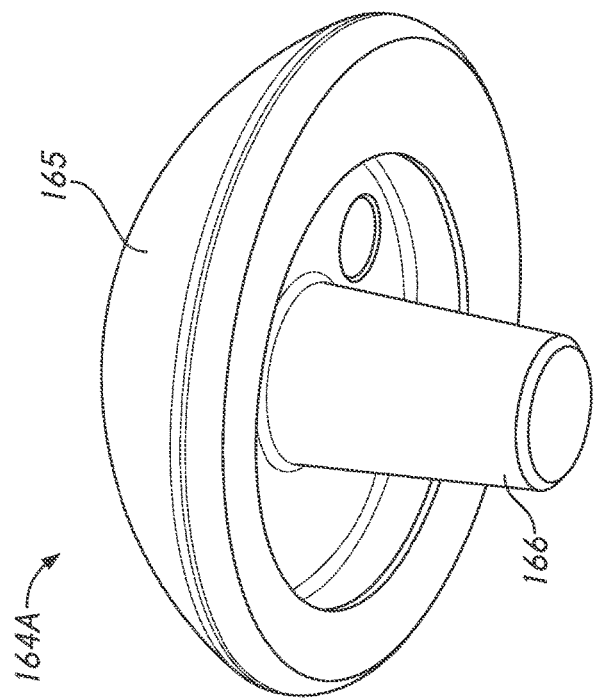
FIG. 5G
FIG. 5H
FIG. 5F

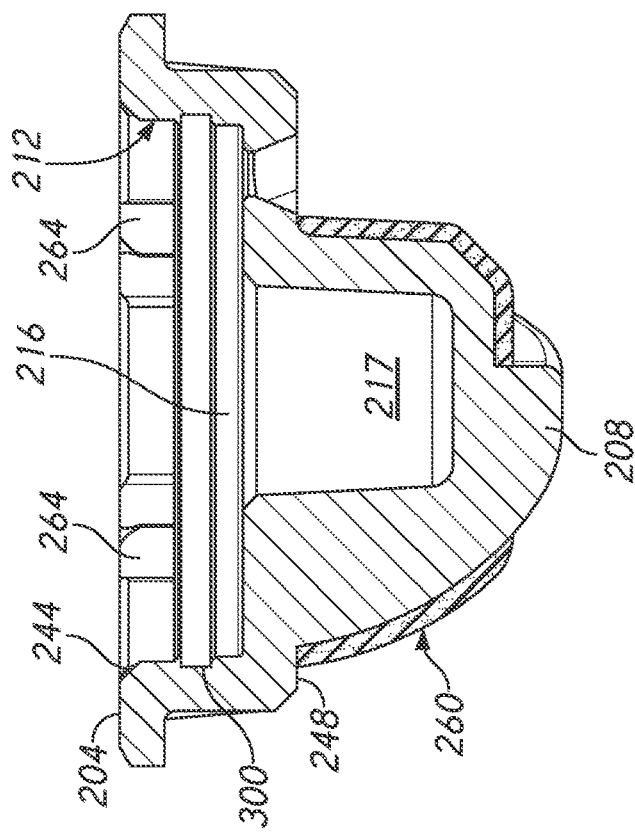
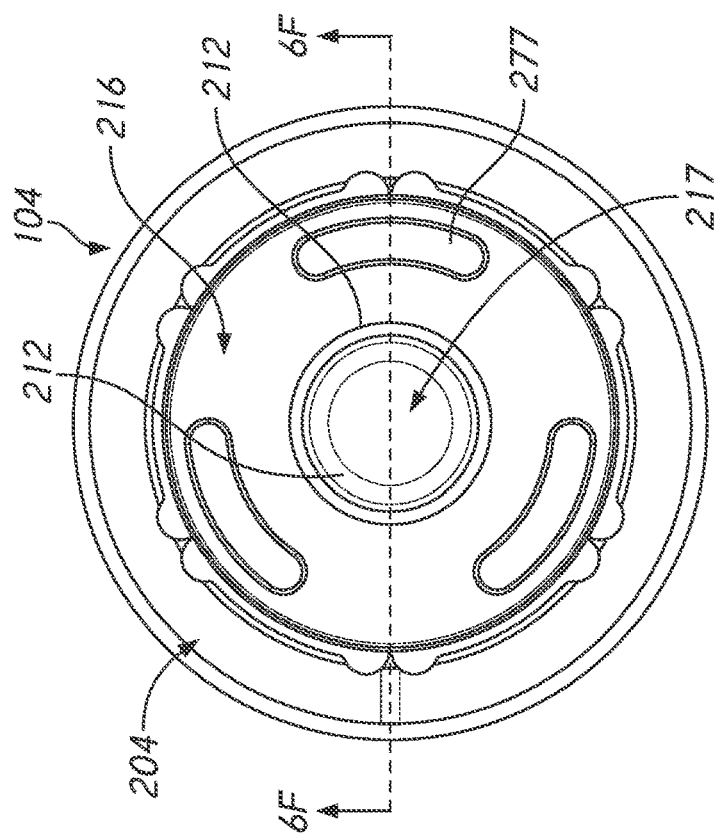
FIG. 6E
FIG. 6F

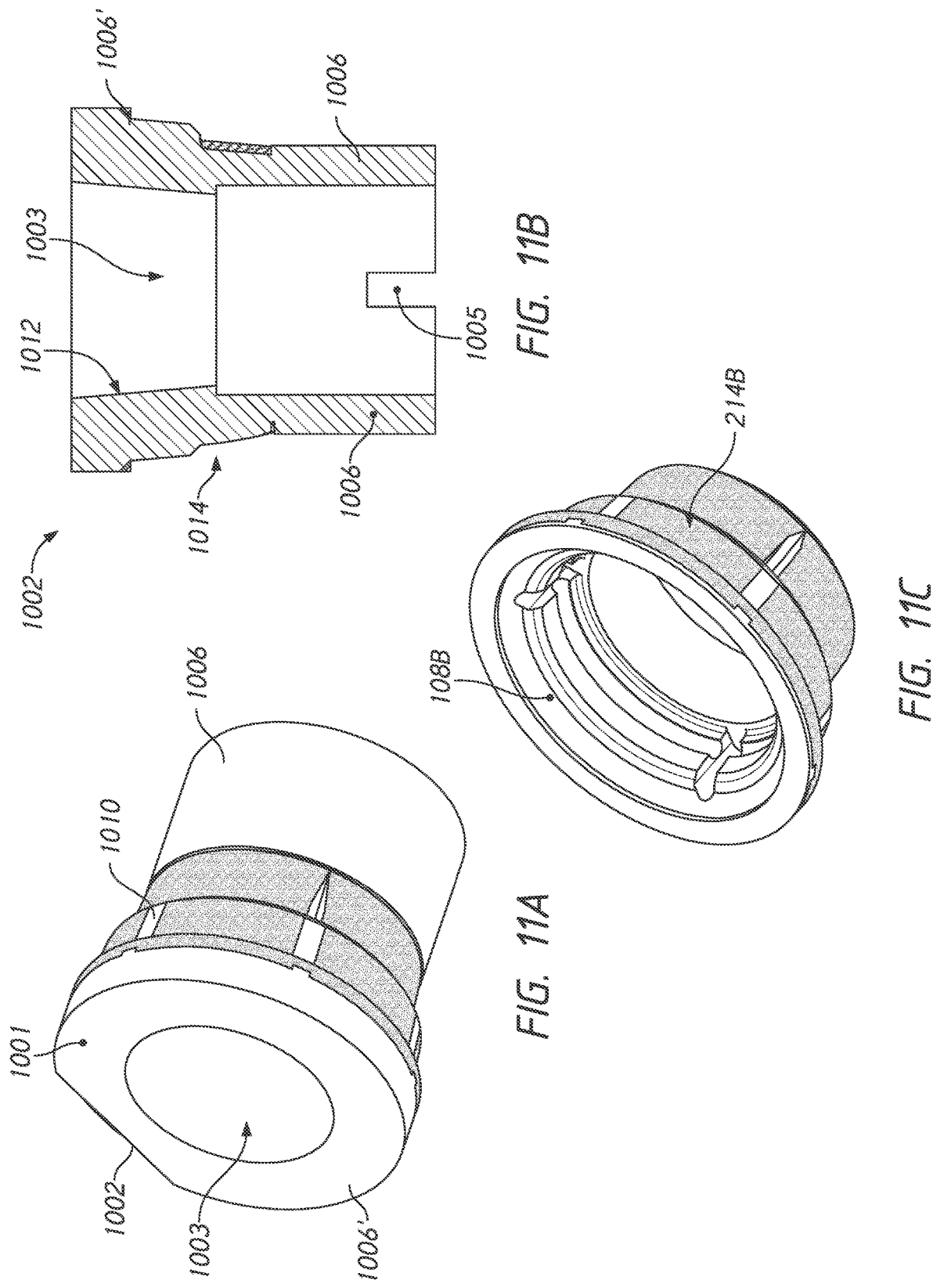

SHOULDER PROSTHESIS COMPONENTS AND ASSEMBLIES

CROSS-REFERENCE TO RELATED APPLICATIONS

This application is a continuation of co-pending U.S. patent application Ser. No. 17/250,964, filed on Apr. 2, 2021, which is a U.S. national phase application under 35 U.S.C. § 371 of International application No. PCT/US19/54005, filed on Oct. 1, 2019, which claims priority to U.S. Provisional Application No. 62/740,333, filed on Oct. 2, 2018, the entire contents of which are incorporated herein by reference.

FIELD

The present application relates to apparatuses and methods for reverse and anatomic shoulder prostheses.

BACKGROUND

Arthroplasty is the standard of care for the treatment of shoulder joint arthritis. A typical anatomical shoulder joint replacement attempts to mimic anatomic conditions. For example, a metallic humeral stem and a humeral head replacement are attached to the humerus of the arm and replace the humeral side of the arthritic shoulder joint. Such humeral head replacement can articulate with the native glenoid socket or with an opposing glenoid resurfacing device.

For more severe cases of shoulder arthritis, the standard treatment is a reverse reconstruction, which includes reversing the kinematics of the shoulder joint. A reverse shoulder prosthesis can be provided by securing a semi-spherical device (sometimes called a glenoid sphere) to the glenoid and implanting a humeral stem with a cavity capable of receiving the glenoid sphere.

As patient disease may progress after anatomic treatment, revision surgery may be necessary to perform a reverse reconstruction of the shoulder. In the known art, the change in the type of prosthesis is addressed either below the plane of resection or above the plane of resection. In prosthesis that are converted from anatomic to reverse by a modularity below the plane of resection, removal of anatomic devices that have integrated into the patient's bony anatomy proves to be difficult for the surgeon, and could potentially cause excessive patient bone loss. One advantage of such conversion is that the reverse insert could partially reside below the resection plane and therefore reduce the distance between the cavity and the lateral contour of the humerus. Such position has proven to be beneficial to a reversed kinematics. In contrary, in prosthesis that are converted from anatomic to reversed above the plane of resection thanks to an adaptor, reverse kinematic is altered as the position of the cavity is further push out of the humerus by the addition of the adaptor above the resection plane. Such construct are typically made of three (3) components that present an extra modularity in comparison to a two (2) component construct and could potentially cause disassembly or breakage of the construct. One possibility to limit the alteration of the kinematics and limit the modularity is to inverse the bearing surface material by having a harder cavity within the humerus and a softer semi-spherical device secured to the glenoid. But the proven clinical design and preferred embodiment is usually that the cavity is softer than the semi-spherical device.

SUMMARY

Improved humeral components, assemblies, and methods are needed to provide more flexibility in working with soft tissue around the shoulder joint. Such components may benefit from placement of at least a portion of the humeral anchor below a humerus resection plane. Such components may benefit from placement of at least a portion of the humeral anchor and also at least a locking portion of an articular assembly below a humerus resection plane.

In one embodiment, a humeral anchor is disclosed. The humeral anchor can include a first end and a second end. The humeral anchor can include an interior surface extending between the first end and the second end, the interior surface disposed about a recess disposed between the first end and the second end. The recess can be configured to secure a coupling of a shoulder articular body directly to the interior surface.

In some embodiments, a transverse surface can be configured to engage a humeral bone layer exposed by resection or other preparation when the humeral anchor is implanted to resist subsidence. The transverse surface can comprise a portion of a collar disposed at the first end of the humeral anchor. The transverse surface can comprise an anti-rotation feature disposed between the first end and the second end of the humeral anchor. The interior surface can comprise a tapered surface for engaging an articular assembly. The interior surface can be disposed about the interior surface comprises a slot for engaging an articular assembly. An exterior surface having a porous surface can be at least partially bounded by a non-porous edge, the non-porous edge being disposed between the porous surface and the second end. The interior surface can comprise a first taper disposed towards the first end and a second taper disposed towards the second end. An exterior surface having a first tapered portion can be disposed about the first end and a second tapered portion can be disposed about a portion of the humeral anchor between the first tapered portion and the second end of the humeral anchor, the second tapered portion being discontinuous from the first tapered portion. The first tapered portion can have a first angle away from an axis disposed from the first end to the second end and the second tapered portion can have a second angle away from the axis disposed from the first end to the second end, the second angle being greater than the first angle. The interior surface can comprise a groove configured to receive a locking ring of an articular body assembly. In some embodiments, the humeral anchor can include a plurality of struts disposed about an exterior surface of the humeral anchor between the first end and the second end. A porous surface can be disposed between at least two struts of the plurality of struts. A plurality of struts can be disposed about an exterior surface of the humeral anchor. The exterior surface can have a first portion disposed about the first end and a second portion between the first portion and the second end of the humeral anchor, the struts being disposed about the first portion. A first plurality of struts can be disposed about the first portion and at least one strut is disposed about the second portion. The first plurality of struts can have twice as many struts as the second plurality of struts. The struts can be disposed about the second portion. The struts can be configured to reduce, minimize or eliminate rotation of the humeral anchor.

In some embodiments, a kit can include a first humeral comprising a first humeral anchor exterior surface and a first collar disposed at the first end thereof. The kit can include a second humeral anchor comprising a second humeral anchor exterior surface and a second collar disposed at the first end thereof. The first humeral anchor and the second humeral anchor can have identical interior surfaces. The first collar and the second collar can have the same outer perimeter dimensions. The second humeral anchor exterior surface can be larger than the first humeral anchor exterior surface.

In some embodiments, the humeral anchor can have at least one fin configured to reduce, minimize or eliminate rotation of the humeral anchor when the humeral anchor is implanted in bone of a humerus. The fin can be disposed at the second end of the humeral anchor. In some embodiments, an array of fins can be disposed radially at the second end of the humeral anchor.

In some embodiments, a stemmed anchor can include the humeral anchor and a stem coupled with and extending from the second end of the humeral anchor. In some embodiments, a kit can include the humeral anchor configured as a stemless anchor and the stemmed anchor. The humeral anchor portion of the stemmed anchor and the stemless humeral anchor can be identical. The first end can comprise a planar surface and the stem can be disposed along a longitudinal axis, the longitudinal axis being disposed at an angle of 135 degrees to the planar surface. The first end can comprise a planar surface and the stem is can be disposed along a longitudinal axis, the longitudinal axis being disposed at an angle of 145 degrees to the planar surface. In some embodiments, an angle between a planar surface and a longitudinal axis of the stem is patient specific. In some embodiments, a ratio between a diameter of the first end of the humeral anchor and a distal diameter of the stem is patient specific. The distance between a longitudinal axis of the humeral anchor and a longitudinal axis of the stem can be patient specific.

In some embodiments, a humeral implant assembly is disclosed. The humeral implant assembly can comprise the humeral anchor and an articular assembly comprising an articular body and a locking component. The articular body can comprise at least one strut configured to engage at least one slot disposed in the interior surface of the humeral anchor. The at least one strut can comprise a first portion and a second portion, the locking component extending between the first and second portions of the strut. The locking component can comprise an undulating ring.

In some embodiments, a kit can comprise a first assembly having a first humeral anchor having a first interior surface with a first interior surface circumference adjacent to the first end thereof. The kit can include a second assembly having a second humeral anchor having a second interior surface with a second interior surface circumference adjacent to the first end thereof. The locking component of the first assembly and the locking component of the second assembly can be configured to provide uniform insertion force during advancement of articular assembly into respective humeral anchor.

In some embodiments, the recess is a first recess and the humeral anchor further comprises a second recess disposed between the first recess and the second end, wherein the second recess is configured to receive a coupler secured to or adapted to be secured to an anatomical articular body. The humeral anchor can include an exterior surface comprising a first cylindrical portion disposed about the first recess and a second cylindrical portion disposed about the second recess, and a plurality of rotation control features extending radially from the second cylindrical portion to the second end of the humeral anchor. The rotation control features can comprise fins extending radially outwardly from a central portion of the anchor. The second cylindrical portion can comprise an outer wall having a radius less than an inner radius of the first recess.

In some embodiments, a kit can include a humeral anchor comprising a stem and metaphysis portion having a metaphyseal profile and a stemless humeral anchor comprising an exterior surface. The exterior surface of the stemless humeral anchor can be configured to occupy less volume of a metaphysis of a patient than is the metaphyseal profile of the humeral anchor comprising the stem. The humeral anchor can comprise an exterior surface having a first cylindrical portion disposed around a first recess and a second portion disposed around a second recess.

In some embodiments, a humeral anchor insertion instrument can include an elongate shaft having a first end and a second end and a handle disposed at the first end of the elongate shaft. An expandable grip can be disposed at the second end of the elongate shaft. The handle can be configured to actuate the expandable grip to a first configuration to apply a radially outward force to an interior surface of a humeral anchor and to a second configuration to separate the expandable grip from the interior surface of the humeral anchor.

In some embodiments, the expandable grip can comprise an expansion disc having a peripheral surface configured to engage the interior surface of the humeral anchor and a slot configured to receive a wedge member to enlarge the peripheral surface in the first configuration. The expandable grip comprises a split collet in some embodiments.

In some embodiments, a method of manufacturing a joint anchor is disclosed. The method can include forming a blank component and at least one handle portion coupled to the blank component, the blank component having a shape configured to couple with a shoulder joint articular body. The method can include machining an exterior surface of the blank component to define exterior surface features of the joint anchor. The method can include removing the at least one handle portion.

In some embodiments, forming the blank component comprises using a three-dimensional (3D) printing technique to form the blank component.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 4E illustrates an exploded view that shows the stemless anchor of FIG. 4A configured to connect to an adaptor for coupling to a stemmed anchor;

FIG. 4H is a schematic side view of the reverse articular component shown in FIG. 4F;

FIG. 4I is a schematic side sectional view of the reverse articular component shown in FIG. 4F;

FIG. 4J is a magnified perspective view of a portion of the reverse articular component shown in FIG. 4F;

FIG. 5C is a schematic side sectional view of the anchor of FIG. 5A;

FIG. 5F is a schematic bottom perspective view of an articular body, according to some embodiments;

FIG. 5G is a schematic top perspective view of a coupler, according to some embodiments;

FIG. 5H is a schematic bottom perspective view of the coupler of FIG. 5G;

FIG. 6E is a top plan view of the humeral anchor of FIGS. 6A-6B;

FIG. 6F is a schematic side sectional view of the humeral anchor, taken along section 6F-6F;

FIG. 11A is a schematic perspective view of a blank die supporting a blank component prior to a machining process;

FIG. 11B is a schematic side sectional view of the blank die of FIG. 11A; and

FIG. 11C is a schematic perspective view of a finished stemless humeral anchor using the devices of FIGS. 11A-11B.

DETAILED DESCRIPTION

Figure 1A:
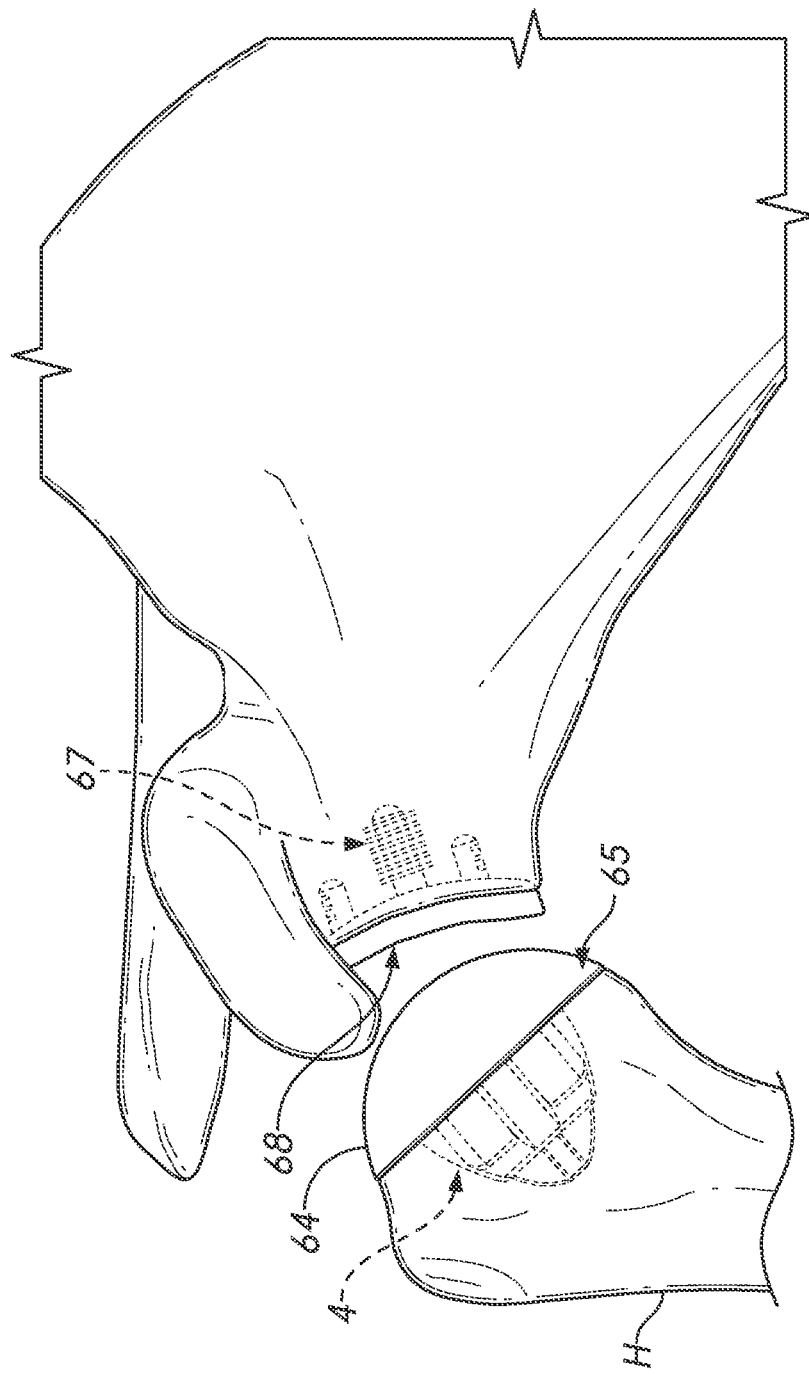
FIG. 1A shows an anatomic total shoulder arthroplasty system disposed in the humerus and the glenoid of a shoulder.
Figure 1B:
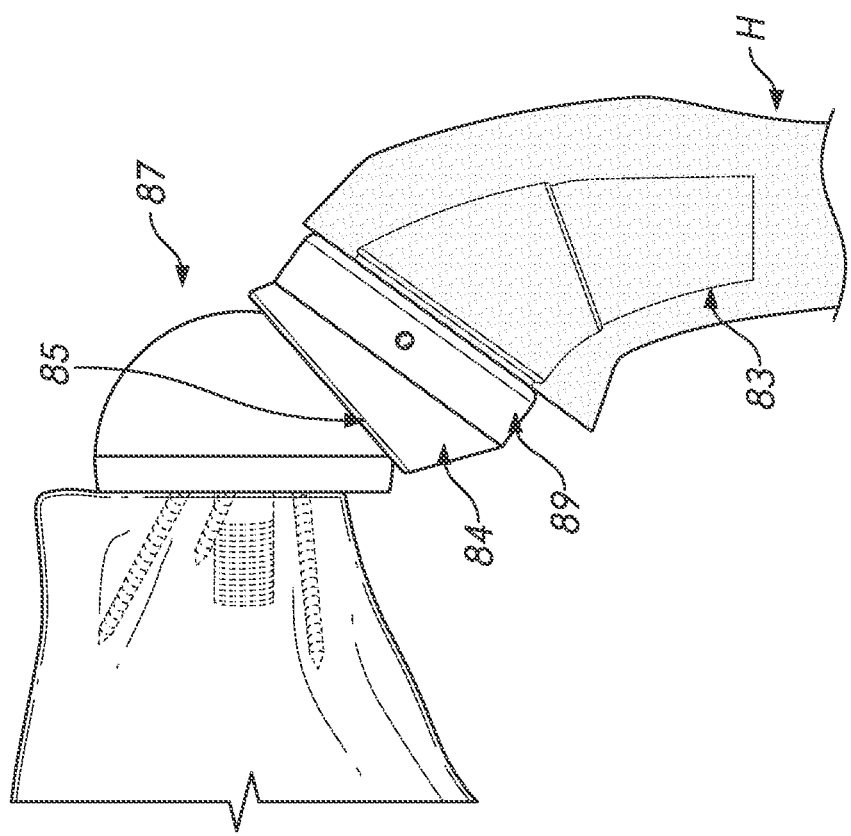
FIG. 1B shows a humeral implant assembly of the total shoulder system shown in FIG. 1A.

FIGS. 1A and 1B show two conventional approaches to total shoulder arthroplasty. FIG. 1A shows an anatomic approach in which the humeral head is replaced with an articular body 64 having an convex articular surface 65. The glenoid of the scapula can be modified with an implant 67 providing a concave surface 68 for articulation of the humeral articular body 64 The humeral articular body 64 is secured to the humerus H using a stemless anchor 4 that is dedicated for and only compatible with the anatomic articular body 64.

FIG. 1B shows a reverse approach in which the humerus H is fitted with an articular body 84 having a concave articular surface 85. The glenoid region of the scapula is fitted with a spherical articular body, commonly called a glenosphere 87. In this case, the concave articular surface 85 placed on the humerus articulates of the glenosphere 87, which is fixed relative to the scapula. The reverse articular body 84 is mounted to a tray 88 that is disposed between the reverse humeral articular body 84 and a stem anchor 83 that is surgically implanted in the humerus H. The humerus H is prepared by providing access to the medullary canal of the humerus H.

One can see that the anatomic and reverse approaches generally use different hardware to secure the articular components. So, switching from an anatomic to a reverse configuration requires extraction of the stemless anchor 4. The bone stock that remains after such an extraction may or may not be suitable for supporting the stem anchor 83. Also, the presence of the tray 88 requires more of the joint space. Thus, the reverse configuration may only be suitable for some patients with large joint space or following more invasive preparation of the humerus and/or the scapula.

I. Overview of Shoulder Prosthesis Assemblies

Various embodiments disclosed herein relate to shoulder prosthesis assemblies that can beneficially lead to improved patient outcomes, for example, by reducing the volume of bone removed from the patient's humerus, reducing surgery time, improving convertability between anatomical and reverse prostheses, providing adaptability with stemmed anchors, and improving reliability of the prosthesis. In some conventional shoulder arthroplasty techniques, a humeral stem anchor may be inserted into the patient's humerus and can be configured to engage with an articular body attached to the glenoid surface. Such a stemmed anchor may present long-term fixation issues, as well as undesirable radiologic signatures such as radiolucencies, spot welds, etc. To reduce fixation problems, radiologic signatures, and surgery times associated with traditional stemmed anchors, stemless anchors can be used.

Indeed, stemless shoulder arthroplasty has become much more attractive to surgeons for a number of reasons, including shorter surgery time, less blood loss, fewer periprosthetic fractures, easier anatomic reconstructions, etc. Stemless shoulder arthroplasty has been largely limited to use in anatomic reconstructions, such that reverse reconstructions can be challenging. Moreover, providing a stemless reverse reconstruction may not be as bone conserving as anatomic reconstructions. Further, it may be challenging to insert stemless anchors in the anatomy in a way that adequately or easily secures the stemless anchor to the humerus. For example, some stemless anchors may be twisted or threaded into the anatomy.

Beneficially, various embodiments disclosed herein disclose a reverse arthroplasty stemless device that can preserve as much bone volume as similar stemmed devices. Moreover, the reverse arthroplasty stemless devices disclosed herein can be converted to anatomical devices in some embodiments. In various embodiments, the stemless devices can be incorporated into one or more kits that include stemmed anchors, so that the clinician can select the appropriate prosthesis (e.g., stemmed or stemless) in the operating room after observing the patient's degree of humeral damage.

Figure 2A:
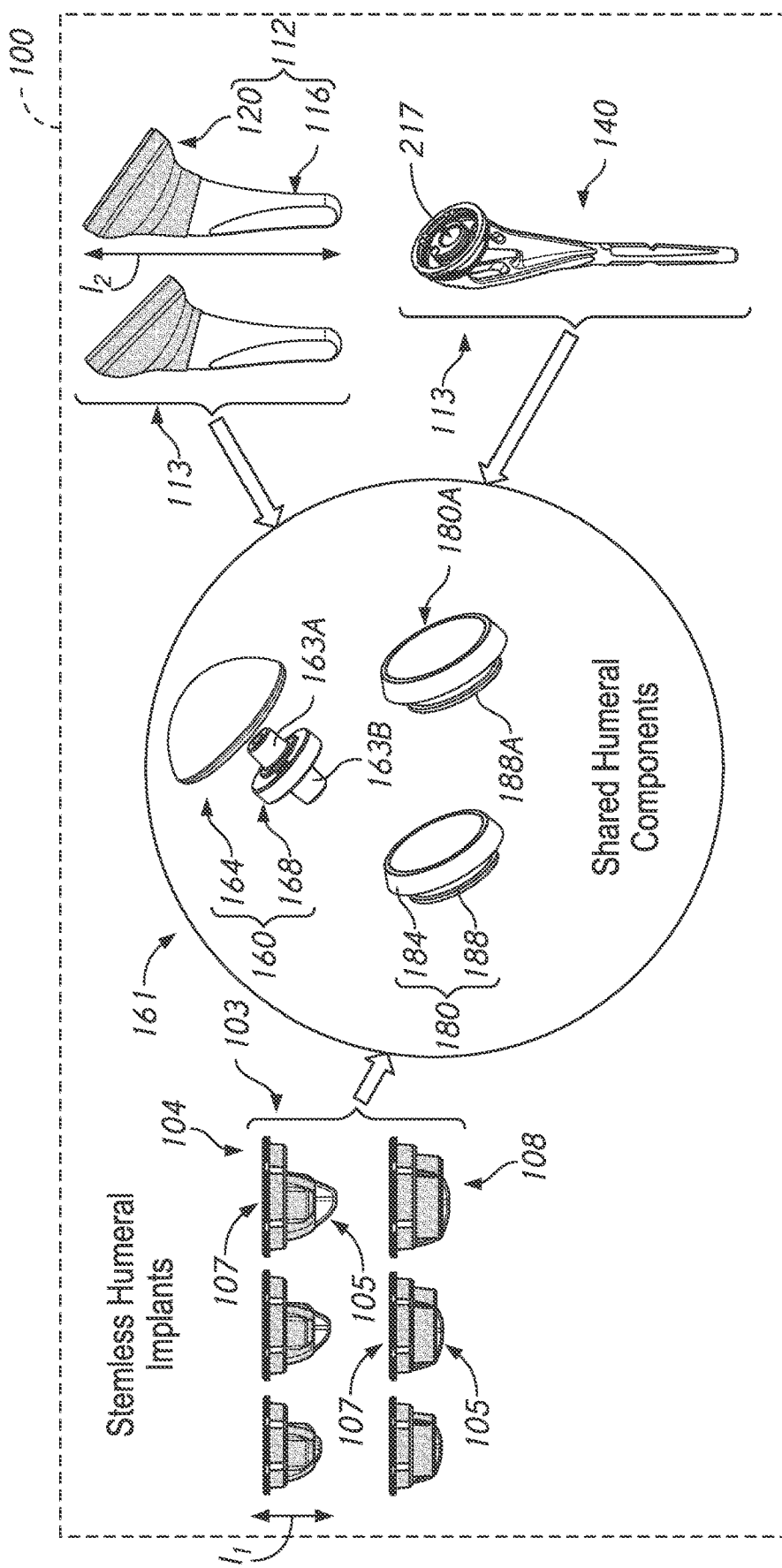
FIG. 2A is a schematic diagram of a total arthroplasty system comprising an arthroplasty kit that can be used to perform anatomic or reverse arthroplasty, or to convert from one of anatomic to reverse or reverse to anatomic arthroplasty, according to various embodiments.

FIG. 2A is a schematic diagram of a total arthroplasty system comprising an arthroplasty kit 100 that can be used to perform anatomic or reverse arthroplasty, or to convert from one of anatomic to reverse or reverse to anatomic arthroplasty, according to various embodiments. The kit 100 can comprise one or a plurality of stemless humeral anchors 103, one or a plurality of stemmed humeral anchors 113, and one or a plurality of articular components 161. For example, the kit 100 can include a plurality of bowl-shaped stemless humeral anchors 104 with finned distal portions. As explained herein, the stemless humeral anchors 104 can have a tapered profile in which a distal portion 105 of the anchor 104 tapers significantly compared with a proximal portion 107 of the anchor 104, such that the distal portion 105 is significantly laterally or radially narrower than the proximal portion 107. The relatively narrow distal portion 105 of the anchor 104 can beneficially preserve humeral bone volume by occupying less space within the humerus. The kit 100 may additionally, or alternatively, include a plurality of bowl-shaped stemless humeral anchors 108. The distal portion 105 of the bowl-shaped humeral anchors 108 may have a smaller taper as compared with the humeral anchors 104. The larger distal portion 105 of the humeral anchors 108 can serve a bone-filling function. A more voluminous distal portion 105 occupies more of the bone volume distal the humeral resection. This can be beneficial for example when the bone quality toward the center of the metaphysis would not sufficiently support the more tapered anchor 104 but the bone quality toward the cortical portion would sufficiently support the anchor 108.

As shown in FIG. 2A, the stemless anchors 103 can be provided in a plurality of sizes to accommodate patients of different sizes, different degrees of bone damage to the humerus, etc. In some embodiments, the lateral size of the stemless anchors 103 may vary so as to fit within different-sized resections of the humerus. In some embodiments, a length $l_1$ of the stemless anchors 103 may also vary so as to extend into the humerus by a depth that the clinician selects based on the particular patient being treated.

The kit 100 can also include one or a plurality of stemmed humeral anchors 113. The kit 100 can include one or more humeral stem anchors 112, each of which includes a proximal metaphysis portion 120 and an elongate diaphysis portion (e.g., stem portion) 116 extending therefrom. In some embodiments, the kit 100 can also include a trauma or fracture stem anchor 140, which can be used in patients that have experienced a fracture of the humerus H. The stemmed humeral anchors 113 may be used in patients in which stemless anchors 103 may not be adequately secured to the humerus, for example, in patients that have experienced severe bone loss. As with the stemless anchors 103, the kit 100 can include stemmed anchors 113 having a plurality of different sizes, e.g., different lateral sizes and/or different lengths $l_2$. For example, as shown in FIG. 2A, the stemmed humeral anchors 113 can have respective lengths $l_2$ that are longer than the lengths $l_1$ of the stemless anchors 103. In various embodiments, the lengths $l_2$ of the stemmed humeral anchors can be in a range of 55 mm to 125 mm. By contrast, the shorter lengths $l_1$ of the stemless humeral anchors 103 can be in a range of 16 mm to 28 mm. In various embodiments, stemmed humeral anchors 113, 140 can be configured to reach into the intramedullary canal of the humerus H for additional anchorage.

Beneficially, the kit 100 can comprise one or a plurality of shared humeral components that be used with either the stemless humeral implants 103 or the stemmed humeral implants 113, depending on which implant 103 or 113 would be more appropriate for a particular patient's humeral anatomy. For example, the shared humeral components of the kit 100 can comprise a plurality of inserts 161 that can be used in conjunction with either the stemless implants 103 or the stemmed implants 113.

For example, the kit 100 can include an anatomic articular component 160 configured to mechanically couple to both the stemless humeral implants 103 and the stemmed humeral implants 113. The clinician may select the anatomic articular component 160 for procedures in which an anatomic reconstruction is suitable. The anatomic articular component 160 can comprise a coupler 168 and an articular body 164 (anatomical) configured to mechanically engage the coupler 168. As shown in FIG. 2A, the articular body 164 for the anatomic articular component 160 can comprise a rounded, convex surface configured to engage a glenoid surface of the patient. As explained herein, the coupler 168 can serve to mechanically connect the anatomical articular body 164 (e.g., a rounded or essentially spherical surface) to either a stemmed humeral implant 103 or a stemmed humeral implant 113, depending on the patient's humeral bone structure. The articular body 164 and the coupler 168 can comprise a metal, such as cobalt, chrome, or titanium. In some embodiments, the articular body comprises a pyrocarbon layer on at least the articular surface. In various embodiments, the kit 100 can include anatomic articular components 160 having a plurality of sizes.

The kit 100 can also include a reverse articular component 180 configured to mechanically couple to both the stemless humeral implants 103 and the stemmed humeral implants 113. The clinician may select the reverse articular component 180 for procedures in which a reverse anatomic reconstruction is suitable. The reverse articular component 180 can comprise a reverse articular body 184 and a locking device 188 configured to secure the reverse articular component 180 to a stemless humeral implant 103 or a stemmed humeral implant 113, depending on the clinician's recommendation during the procedure. As shown, the reverse articular body 184 can comprise a rounded concave surface (e.g., essentially spherical) configured to engage with a glenosphere connected to the glenoid of the patient. In addition, in some embodiments, the kit 100 can include a wear resistant reverse articular component 180A, which may be generally similar to the reverse articular component 180 but may further be formed to include vitamin E to promote long-term compatibility with the patient's bone structure. The reverse components 180, 180A can comprise a polymer, including, for example, ultra high molecular weight polyethylene. In various embodiments, the kit 100 can include reverse articular components 180, 180A having a plurality of sizes.

During an arthroplasty procedure, the clinician may inspect the bone structure of the humerus and/or the scapula to determine whether the anatomy is suitable for a stemless or stemmed humeral anchor, and whether the anatomy is suitable for an anatomical or reverse anatomical reconstruction. Beneficially, the kit 100 shown in FIG. 2A can provide the clinician with a total arthroplasty system including components that are compatible with stemless or stemmed anchors, and with anatomical or reverse anatomical constructions. For example, during a procedure, the clinician may observe that the patient has sufficient humeral bone structure so that a stemless anchor 103 may be used to reduce the damage to the patient's anatomy. The clinician can select a bowl-shaped anchor 104 or 108, and can select the corresponding size appropriate for the patient. The clinician may also elect whether to proceed with an anatomical reconstruction or a reverse construction, and can accordingly select either the anatomical articular component 160 or the reverse articular component 180, 180A.

Similarly, if during a shoulder arthroplasty procedure, the clinician determines that the patient's bone structure is damaged or otherwise more suited to a stemmed anchor 113, then the clinician can select an appropriately sized stemmed anchor 113. The clinician can further select whether to proceed with an anatomical reconstruction or a reverse construction, and can accordingly select either the anatomical articular component 160 or the reverse articular component 180, 180A. Beneficially, the kit 100 of FIG. 2A includes interchangeable or interoperable components that can be used in stemmed or stemless anchors, and with anatomical or reverse anatomical reconstructions. Because the shared humeral inserts 161 (e.g., anatomical or reverse anatomical articular bodies) can be used with either the stemless or stemmed anchors 103, 113, the clinician can make, or change, reconstruction decisions during surgery. The kit 100 can accordingly enable the clinician to quickly determine the reconstruction procedure most suitable for a patient and can provide the clinician with the components to be used for that reconstruction procedure.

As explained above, for humeral fractures, the kit 100 can also include one or more trauma stems 140. As explained herein in connection with FIGS. 7F-7G, the coupler 168 can comprise a proximal extension 163A configured to connect to the articular body 164 and a distal extension 163B. The distal extension 163B for the fracture stem 140 can be received within a recess 217 of the fracture stem 140 for anatomical reconstructions. The disc or middle portion 162 disposed between the proximal extension 163A and the distal extension 163B can be eliminated since the recess 217 is elevated toward the resection plane. In a modified embodiment, the recess 217 is recessed from (e.g., extends distally from) a distal end of the recess 216, similar to what is shown in FIGS. 7F and 7G. In those embodiments, the disc or middle portion 162 provides a spacer function in use in the trauma stem 140. Additional details of trauma stems may be found throughout International Application No. PCT/US2015/065126, filed Dec. 15, 2015, the entire contents of which are hereby incorporated by reference herein in their entirety and for all purposes.

Figure 2C:
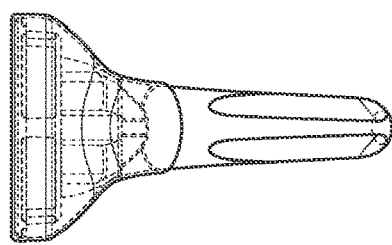
FIG. 2C is a schematic view showing a stemless humeral anchor overlaid with a stemmed humeral anchor.
Figure 2C:
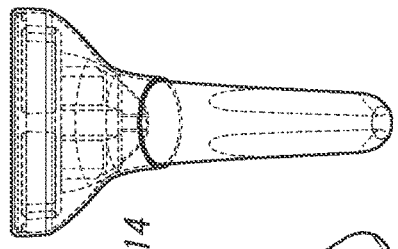
Figure 2C:
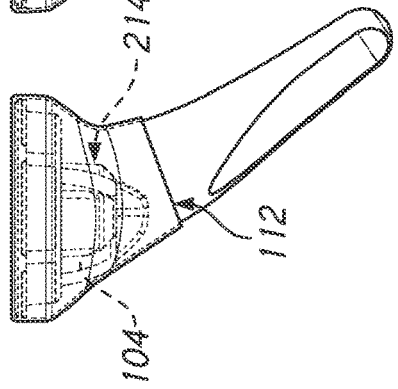
Figure 2B:
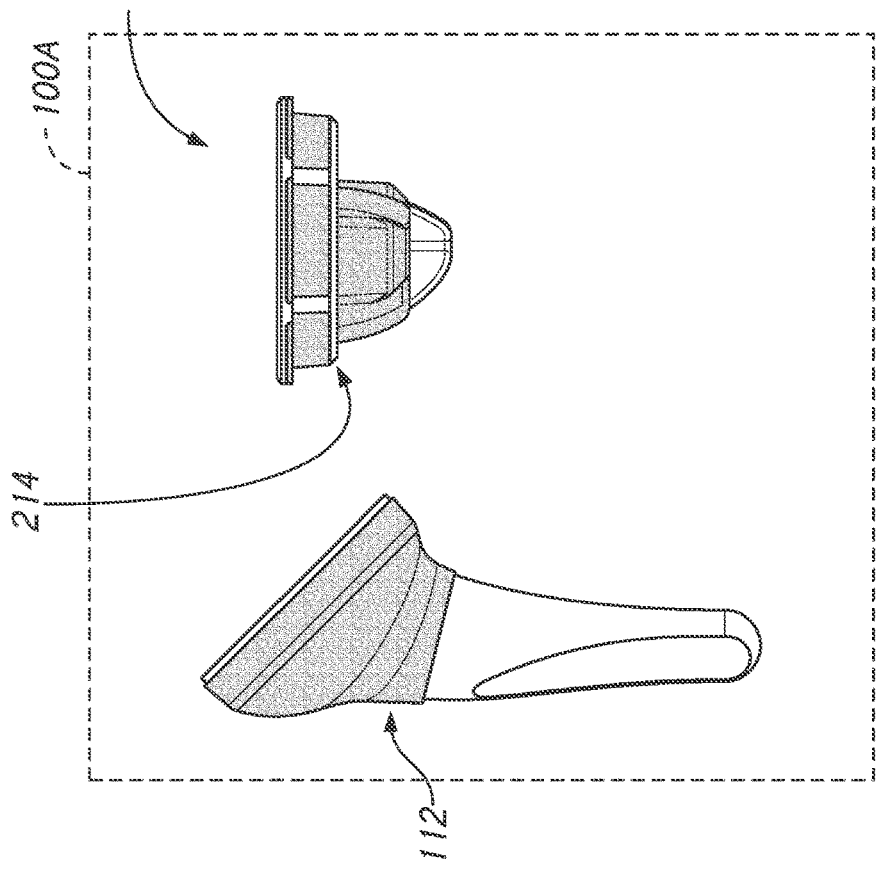
FIG. 2B is a schematic diagram of a total arthroplasty system comprising an arthroplasty kit that can be used to perform anatomic or reverse arthroplasty, or to convert from one of anatomic to reverse or reverse to anatomic arthroplasty, according to another embodiment.

FIG. 2B is a schematic diagram of a total arthroplasty system comprising an arthroplasty kit 100A that can be used to perform anatomic or reverse arthroplasty, or to convert from one of anatomic to reverse or reverse to anatomic arthroplasty, according to another embodiment. FIG. 2C is a schematic view showing a stemless humeral anchor 104 visually overlaid with a humeral stem anchor 112 (not physically disposed within the stem anchor 112). Unless otherwise noted, the components of the kit 100A can be generally similar to like-numbered components of FIG. 2A, except reference numerals in FIGS. 2B and 2C have been appended with the letter "A." As shown in FIG. 100A, the kit 100A can comprise a humeral stem anchor 112 and a stemless humeral anchor 104A. As shown in the overlay of FIG. 2C, an exterior surface 214A of the stemless anchor 104A can occupy or define less volume than the metaphysis portion 120 of the stemmed anchor 112.

Accordingly, during a procedure, the stemless anchor 104A may be inserted into the metaphyseal portion of the humerus. If the clinician determines that the bone structure is damaged such that the stemless anchor 104A is not adequately secured to the humerus, then the clinician can remove the stemless anchor 104A and insert the stemmed anchor 112A into the humerus. The clinician can enlarge the opening into the humerus to accommodate the wider metaphysis portion 120 of the stemmed anchor 112A. Beneficially, because the exterior surface 214A of the stemless anchor 104A occupies a relatively small volume (e.g., less volume of the metaphyseal profile of the humerus than the metaphysis portion 120 occupies), the clinician can have the ability to enlarge the resection without compromising the patient's humeral bone structure. It should be appreciated that, although the metaphysis portion 120 of the stem anchor 112A is wider than the finned portion of the stemless anchor 104A, the proximal end (e.g., the collar, which is described below) may have substantially the same diameter or width, such that the proximal ends may fit within the same size resection.

II. Examples of Humeral Anchors

Figure 3:
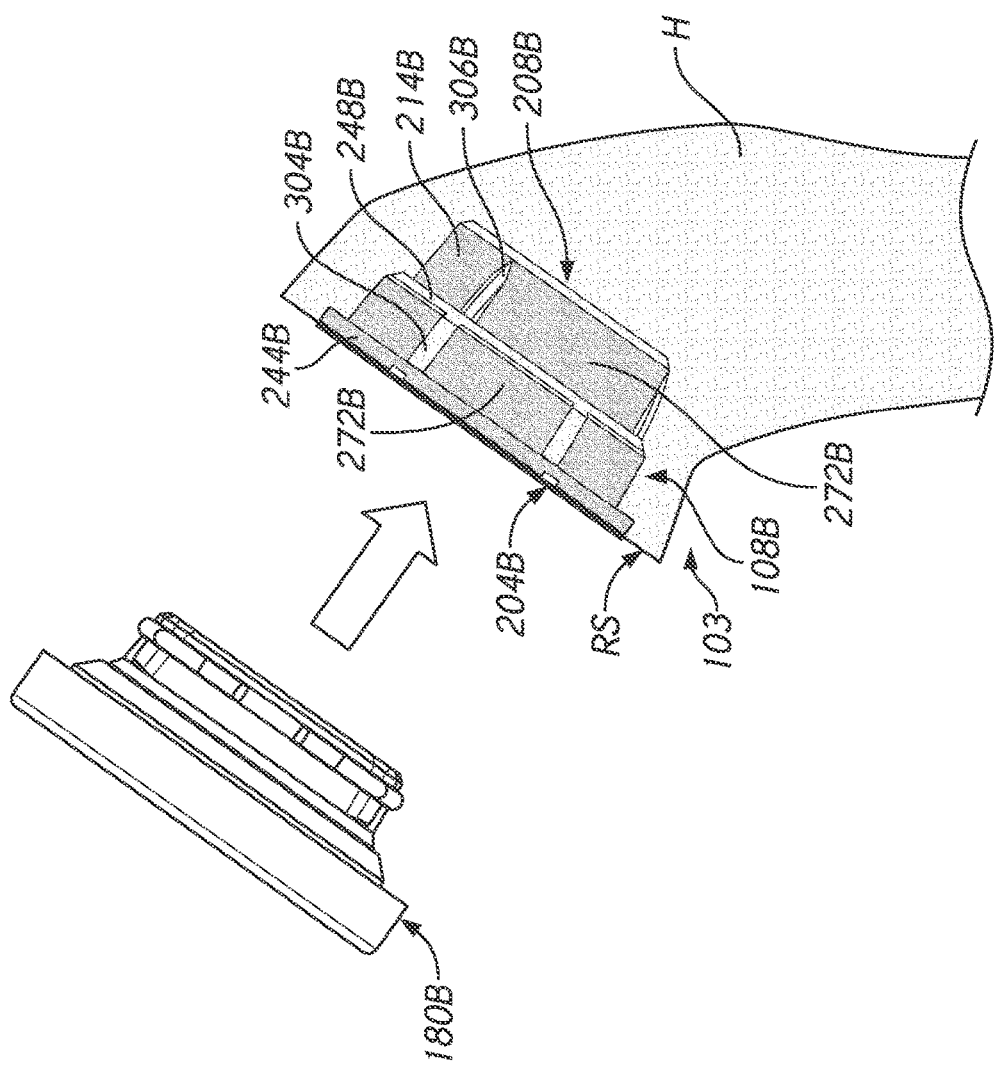
FIG. 3 shows an exploded view of one embodiment of a stemless reverse humeral implant assembly.
Figure 4A:
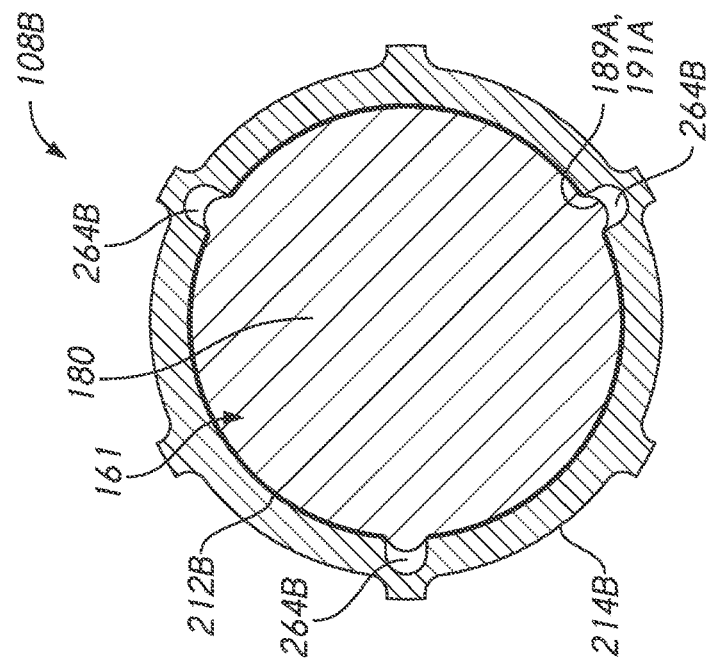
FIG. 4A is a cross-sectional view of the stemless humeral assembly of FIG. 3, the section taken at the plane 4A-4A.
Figure 4:
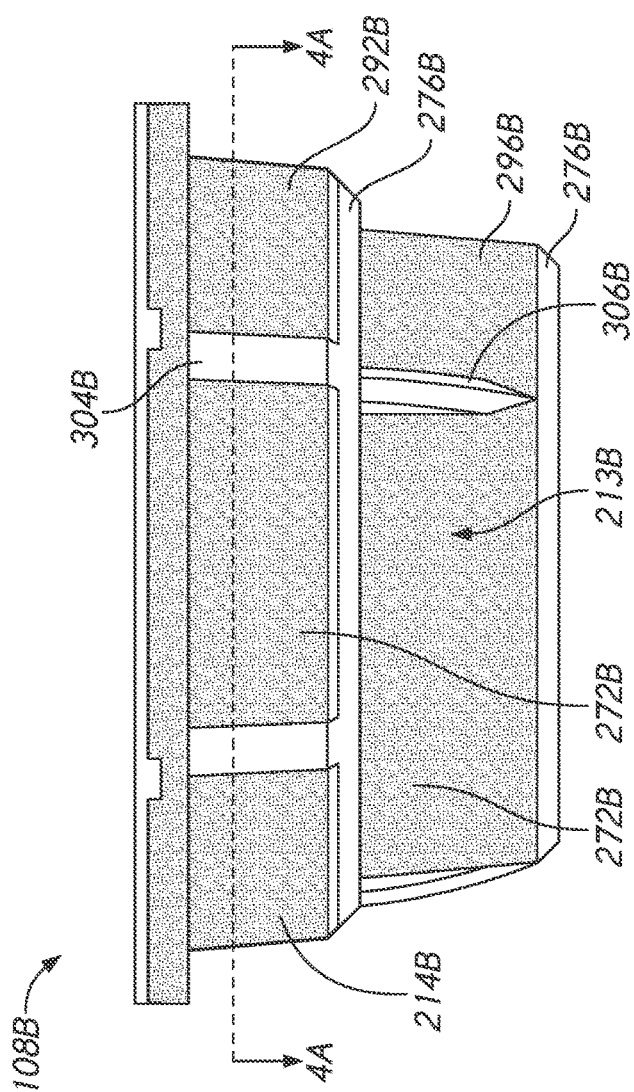
FIG. 4 is a side view of the stemless humeral assembly of FIG. 3.

FIGS. 3-4E illustrate stemless anchor 103 comprising a stemless bowl-shaped humeral anchor 108B, according to one embodiment. The bowl-shaped humeral anchor 108B can have a distal portion in which at least a portion of the exterior surface has a curved (e.g., convex) profile. The distal portion of bowl-shaped humeral anchors may be wider than corresponding distal portions of finned humeral anchors. Unless otherwise noted, reference numerals in FIGS. 3-4E illustrate components similar to those shown in FIGS. 1A-2C, except the reference numerals are appended with the letter "B." FIG. 3 is a schematic side view of the stemless humeral anchor 108B shown secured within the humerus H, with the humerus H illustrated as semi-transparent for ease of illustration. It should be appreciated that, although FIG. 3 shows the stemless anchor 108B, any of the other stemless anchors 103 described herein may be similarly inserted into the humerus H as shown in FIG. 3. As explained herein, in the illustrated embodiment, the anchor 108B may be inserted into the humerus H by non-rotational, direct insertion into the humerus H. In other reconstruction systems, humeral anchors may be inserted into the humerus H using a rotational motion, for example, to thread, screw, or drill the anchor into the humerus H. In such systems, the need to rotate the anchor may complicate the surgical process, such that the clinician must either manually rotate the anchor into position, or use other instruments to rotate the anchor into the humerus H. Accordingly, the disclosed embodiments may beneficially enable direct non-rotational insertion into the humerus H to simplify the replacement procedure.

Furthermore, as shown in FIG. 3, and as explained below, the stemless anchor 108B can include a collar 244B at a first or proximal end 204B of the anchor 108B. As shown in FIG. 3, the collar 244B may be provided generally flush with the resection surface RS. In other embodiments, the collar 244B may be provided slightly above the resection surface RS. In still other embodiments, the collar 244B may be provided slightly below the resection surface RS. An insert 161 (which is illustrated as a reverse articular component 180 in FIG. 3) can be inserted into a recess 216B of the stemless anchor 108B. As explained above, the reverse articular component 180 can be configured to engage with a glenoid sphere. In the illustrated embodiment, at least portions of the recess 216B (see below) and portions of the insert 161 can be disposed below the resection surface RS. Providing portions of the insert 161 (e.g., portions of the articular body 184, such as portions configured for engaging the recess 216B or even a portion of the concave surface) below the resection surface RS can beneficially improve the surgical reconstruction since the prosthesis may more closely match the natural anatomy of the humerus H.

Figure 4C:
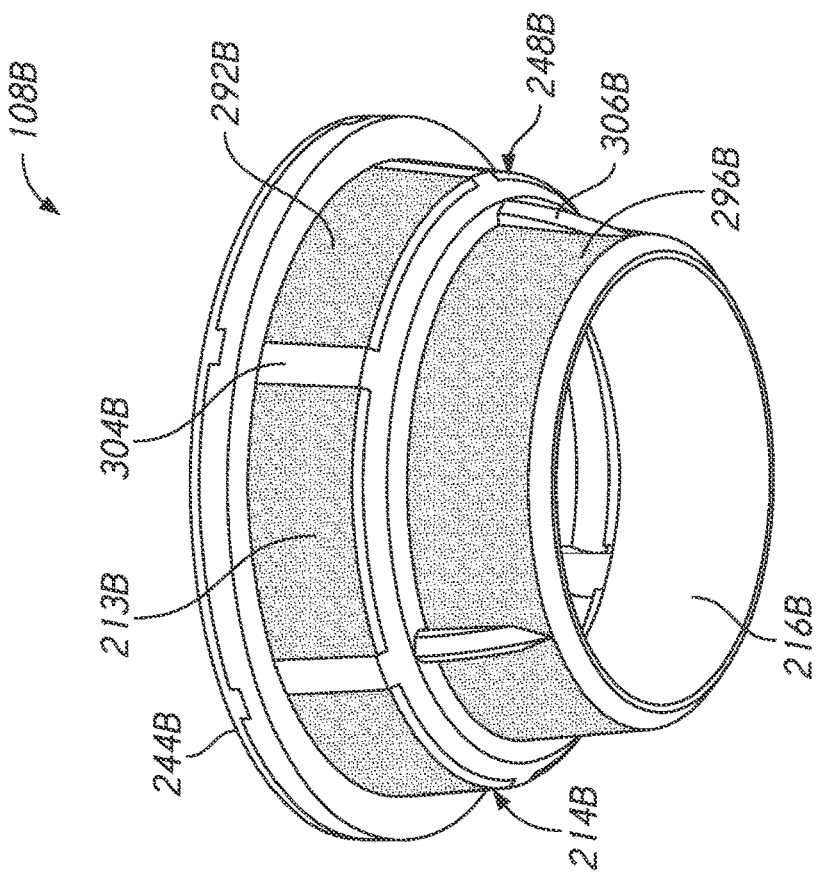
FIG. 4C is a schematic bottom perspective view of the assembly of FIG. 4A.
Figure 4B:
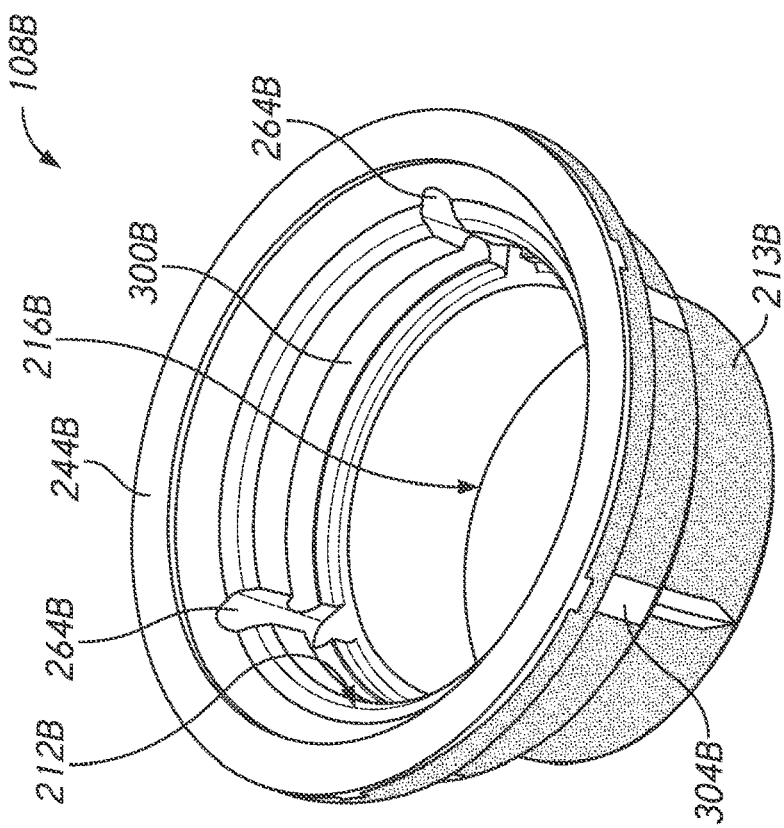
FIG. 4B is a schematic top perspective view of the assembly of FIG. 4A.
Figure 4D:
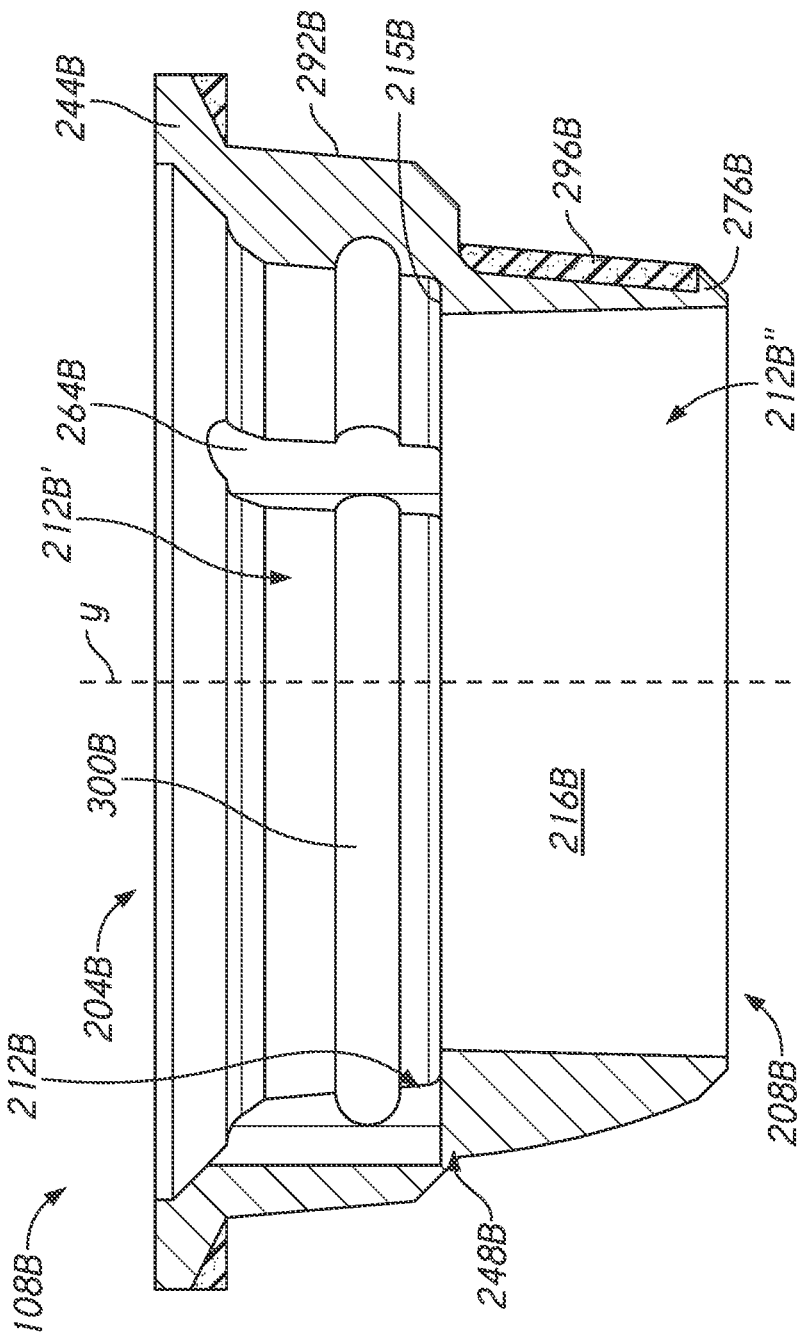
FIG. 4D is a schematic side sectional view of the assembly of FIG. 4A.

FIG. 4 is a schematic side view of the stemless humeral anchor 108B shown in FIG. 3. FIG. 4A is a sectional view of the anchor 108B shown with the insert 161 disposed within the anchor 108B of FIG. 4, taken along section 4A-4A. FIG. 4B is a schematic top perspective view of the anchor 108B of FIG. 4A. FIG. 4C is a schematic bottom perspective view of the anchor 108B of FIG. 4A. FIG. 4D is a schematic side sectional view of the anchor 108B of FIG. 4A.

The anchor 108B of FIGS. 3-4D can have a first end 204B and a second end 208B spaced from the first end 204B. The first end 204B can be a proximal end. The second end 208B can be a distal end. The anchor 108B can comprise a monolithic body. The anchor 108B can comprise a wall 213B having an exterior surface 214B facing outwardly from a central portion of the anchor 108B and an interior surface 212B facing inwardly toward the central portion of the anchor 108B. The interior surface 212B and the exterior surface 214B can extend between the first and second ends 204B, 208B of the anchor 108B. The inner surface 212B can be disposed about a recess 216B disposed between the first and second ends 204B, 208B. The recess 216B can be configured to secure a shoulder articular body or component (such as the reverse articular component 180) to the interior surface 212B. As explained above, a collar 244B can be provided at or near the first end 204B. The collar 244B can comprise a transverse surface configured to engage a humeral bone layer exposed by resection (e.g., at or near the resection surface RS) or other preparation when the humeral anchor 108B is implanted to resist subsidence.

As shown in FIG. 4D, the interior surface 212B may comprise one or more tapered surfaces for engaging an articular assembly, such as any of the inserts 161 shown in FIG. 2A. In the embodiment of FIG. 4D, for example, the interior surface 212B can comprise a first tapered surface 212B' disposed towards the first end 204B and a second tapered surface 212B" disposed towards the second end 208B. As illustrated in FIG. 4D, the first tapered surface 212B' can extend generally between the first end 204B and a shoulder 215B disposed laterally inward from the wall 213B. In various embodiments, the first tapered surface 212B' can be angled or tapered to receive an insert 161 comprising a shoulder articular body, e.g., the anatomical articular body 160 or the reverse articular body 180. In FIG. 4D, the first tapered surface 212B' can be angled such that the recess 216B is wider at the first end 204B than at locations towards the second end 208B (e.g., than at the shoulder 215B). The second tapered surface 212B" can be angled or tapered to engage with an adaptor 460 (see FIG. 4E) for coupling the anchor 108B to a stemmed anchor 113. In FIG. 4D, the second tapered surface 212B" can extend from the shoulder 215B to the second end 208B. In some embodiments, the recess 216B can be wider (or can be approximately the same width) at the second end 208B than at the shoulder 215B. In other embodiments, the recess 216B can be wider at or near the shoulder 215B than at the second end 208B.

As shown in FIGS. 4B and 4D, the interior surface 212B can comprise one or a plurality of slots 264B sized and configured to engage an insert 161 (such as the articular components 160, 180). As explained below, for example, the slots 264B can engage or receive corresponding ridges 189A, 191A of the insert 161 (see, for example, FIG. 4J). As explained herein, the slots 264B can limit rotation of the insert 161 relative to the anchor 108B. The slots 264B can also guide the advancement of the insert 161 into an upper portion of the recess 216B. The slots 264B can be disposed vertically along the interior surface 264B and can be circumferentially spaced from one another. In the embodiment of FIGS. 4B and 4D, the slots 264B can extend from a location proximate the first end 204B towards the shoulder 215B. Further, the interior surface 212B can comprise a groove 300B extending circumferentially about the recess 216B. The groove 300B can be sized and configured to receive a locking ring of an articular body assembly (e.g., any of the inserts 161 described herein).

As shown in FIGS. 4, 4C, and 4D, the exterior surface 214B can comprise a first tapered portion 292B disposed about the first end 204B and a second tapered portion 296B disposed about a portion of the humeral anchor 108B between the first tapered portion 292B and the second end 208B of the anchor 108B. The first tapered portion 292B can have a first angle disposed away from a longitudinal axis y extending through the first end 204B to the second end 208B. The second tapered portion 296B can have a second angle disposed away from the axis y. In some embodiments, the second angle can be greater than the first angle. In the illustrated embodiment, the first and second tapered portions 292B, 296B can be discontinuous from one another. For example, as shown in FIGS. 4C and 4D, a lateral projection 248B can provide at least a portion of the discontinuity between the tapered portions 292B, 296B. Further, the lateral projection 248B can assist in reducing subsidence. Also, providing a multiple stage (e.g., two-stage) taper using the tapered portions 292B, 296B can ease the insertion of the anchor 108B into the humerus H. For example because the second tapered portion 296B has a lower profile than the first tapered portion 292B, the second tapered portion can be fit into a smaller space in the resected humerus. Such placement can be achieved with less reaming than were the second tapered portion 296B along the same taper as the first tapered portion 292B.

In addition, the stemless humeral anchor 108B can comprise a porous surface 272B disposed on the exterior surface 214B. The porous surface 272B can be configured to foster the growth of bone into the porous surfaces 272B to improve integration of the anchor 108B into the anatomy. Further, the porous surfaces 272B can be bounded by one or more non-porous edges 276B that can protect the porous surfaces 272B. In FIG. 4A, for example, an upper non-porous edge 276B can separate the porous surfaces 272B that are disposed on the tapered portions 292B, 296B, respectively. As shown the upper non-porous edge 276B can be disposed between the porous surface 272B disposed on the tapered portion 292B and the second end 208B. A lower non-porous edge 276B can be disposed near the second end 208B. Beneficially, the non-porous edges 276B can protect the porous surfaces 272B during insertion of the anchor 108B into the bone. The portion of the anchor 108B underlying the non-porous surface 276B also can provide one or both of enhanced strength against load directed transverse thereto.

The anchor 108B can also include a plurality of struts 304B disposed about or along the exterior surface 212. For example, as shown in FIG. 4C, the struts 304B can be disposed vertically or along or generally aligned to the longitudinal axis y and can be disposed on the first tapered portion 292B of the anchor 108B. The struts 304B can have an external surface that is tapered as in the first tapered portion 292B. As shown in FIG. 4C, the struts 304B can extend from the first end 204B towards the second end 208B between the ends 204B, 208B (e.g., from the collar 244B to the lateral projection 248B). The struts 304B can be circumferentially spaced from one another with the porous surface 272B being disposed between adjacent struts 304B. There can be several porous surfaces 272B arrayed about the periphery of the first tapered portion 282B, with struts 304B disposed therebetween. The struts 304B can beneficially assist in reducing, minimizing, or eliminating rotation of the humeral anchor 108B. In some embodiments, the struts 304B may be configured to improve the strength of the anchor 108B.

In addition, as shown in FIGS. 4 and 4C, the anchor 108B can include one or a plurality of fins 306B disposed along the exterior surface 212. As shown in FIG. 4C, the fins 306B can be circumferentially spaced from one another with the porous surface 272B intervening between adjacent fins 306B. As shown, the fins 306B can extend from the lateral projection 248B towards the second end 208B. The fins 306B can be angled so as to be thicker near the lateral projection 248B and thinner nearer the second end 208B. The fins 306B can beneficially assist in reducing rotation of the anchor 108B.

FIG. 4E illustrates an exploded view that shows the stemless anchor 108B configured to connect to an adaptor 460 for coupling to a stemmed anchor 113, 140. The adaptor 460 can comprise a first opening 466 at a first end and a second opening 468 at a second end. The second end 208B of the anchor 108B can be disposed around the outer periphery of the adaptor 460 to couple with the adaptor 460. The second opening 468 can be disposed about a joining member 448 (such as a projection or male joining member) of the stemmed anchor 113 to mechanically couple the stemless anchor 108B to the stemmed anchor 113. Accordingly, in various embodiments, the stemless anchor 108B can be used in both stemless and stemmed reconstructions. Additional embodiments of a stem adaptor and kits including one or more stems, adaptors, and related components may be found throughout International Patent Application No. PCT/US2017/028470, filed on Apr. 19, 2017, the entire contents of which are hereby incorporated by reference herein in their entirety and for all purposes. Furthermore, in various embodiments, the coupler 168 (and hence the articular body 164) may couple to the stemmed anchor to provide an anatomical reconstruction for the fracture stem. Additional details of using a fracture stem with components similar to the coupler 168 may be found throughout International Patent Application No. PCT/US2015/065126, the entire contents of which are hereby incorporated by reference herein in their entirety and for all purposes.

Figure 4G:
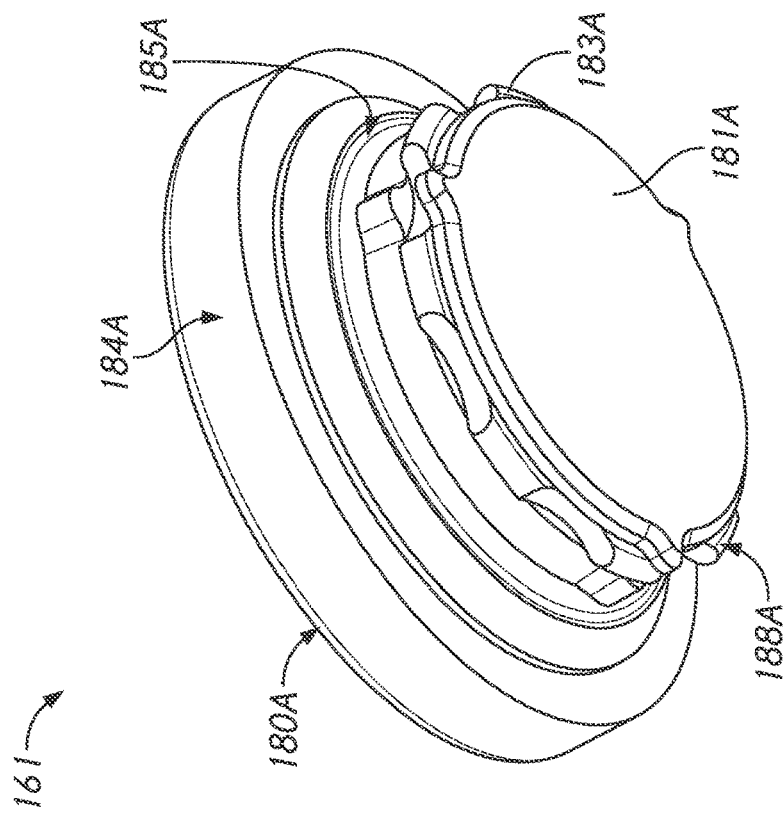
FIG. 4G is a bottom perspective view of the reverse articular component shown in FIG. 4F.
Figure 4F:
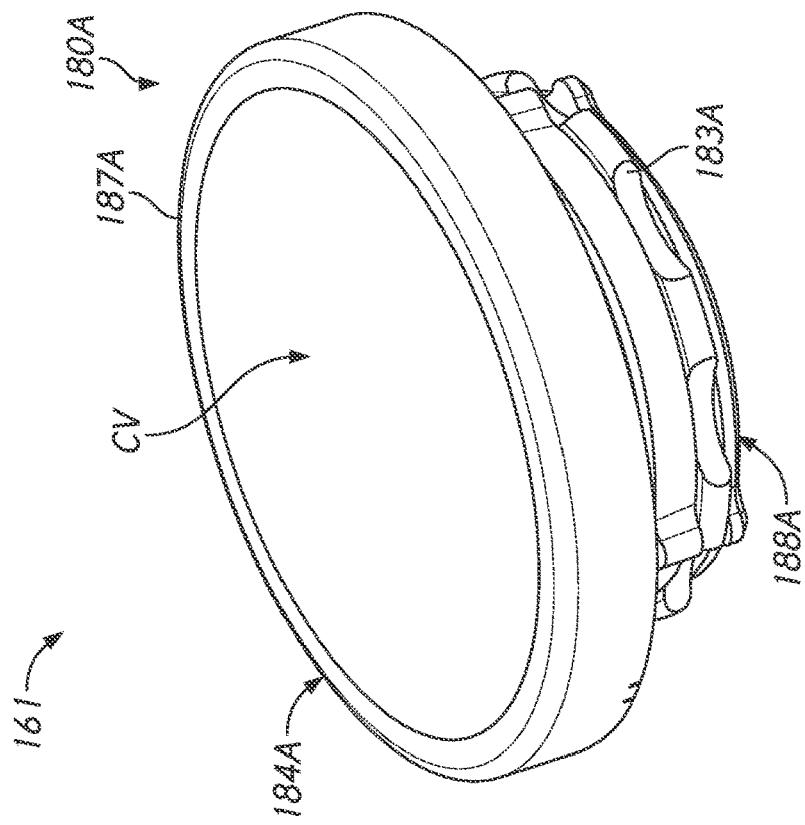
FIG. 4F is a top perspective view of the reverse articular component.

FIGS. 4F-4K illustrate an embodiment of an insert 161 comprising a reverse articular component 180A configured to be used in a reverse shoulder prosthesis by coupling to a glenoid sphere or glenosphere. For example, FIG. 4F is a top perspective view of the reverse articular component 180A. FIG. 4G is a bottom perspective view of the reverse articular component 180A shown in FIG. 4F. FIG. 4H is a schematic side view of the reverse articular component 180A shown in FIG. 4F. FIG. 4I is a schematic side sectional view of the reverse articular component 180A shown in FIG. 4F. FIG. 4J is a magnified perspective view of a portion of the reverse articular component 180A shown in FIG. 4F. Unless otherwise noted, the components of FIGS. 4F-4K may be the same as or generally similar to like numbered components of FIG. 2A, but with the reference numerals appended with the letter "A." As explained above in connection with FIG. 2A, the reverse articular component 180A can comprise a reverse articular body 184A coupled to or formed with a locking device 188A configured to secure the articular component 180A to either a stemless anchor 103 or a stemmed anchor 113.

The reverse articular body 184A can comprise a concave surface CV extending distally from a raised rim 187A. The concave surface CV can comprise a curved surface, which may be generally spherical and shaped to cooperate with a glenoid sphere coupled to a glenoid surface of the patient. When the insert 161 is secured within the humerus, at least a portion of the articular body 184A can be disposed below the resection surface RS. For example, in some embodiments, a connection portion and in some cases, a portion of the concave surface CV can be disposed below the resection surface RS. As an example, at least a distalmost portion of the concave surface CV can be disposed below the resection surface RS. A pedestal portion 181A can extend distally from the upper portion of the articular body 184A. The pedestal portion 181A can be narrower than (or have a smaller diameter than) the raised rim 187A. Furthermore, as shown in FIGS. 4H and 4I, a sloped surface 185A can extend between the pedestal portion 181A and a lower portion of the raised rim 187A. The sloped surface 185A can engage with the interior surface of the stemless or stemmed humeral anchors 103, 113 so as to be slidably inserted into a recess of a humeral anchor.

The locking device 188A can be provided on the pedestal portion 181A and can comprise a snap ring 183A disposed within an outer annular groove 190A of the pedestal portion 181A. As shown in FIG. 4J, the pedestal portion 181A can comprise an upper ridge 189A spaced apart from a lower ridge 191A with the outer groove 190A disposed between the ridges 189A, 191A. Returning to FIG. 4A, the ridges 189A, 191A can engage and be received within the corresponding slots 264B to limit or prevent rotation of the insert 161 relative to the humeral anchor in which it is received. As shown, the ridges 189A, 191A can be disposed vertically (e.g., extending along the axis y) and can be circumferentially spaced from one another.

Figure 4L:
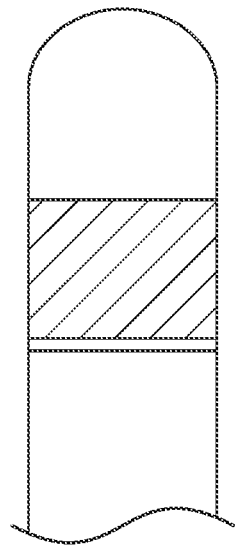
FIG. 4L is a schematic side sectional view of a portion of the snap ring taken along section 4L-4L.
Figure 4K:
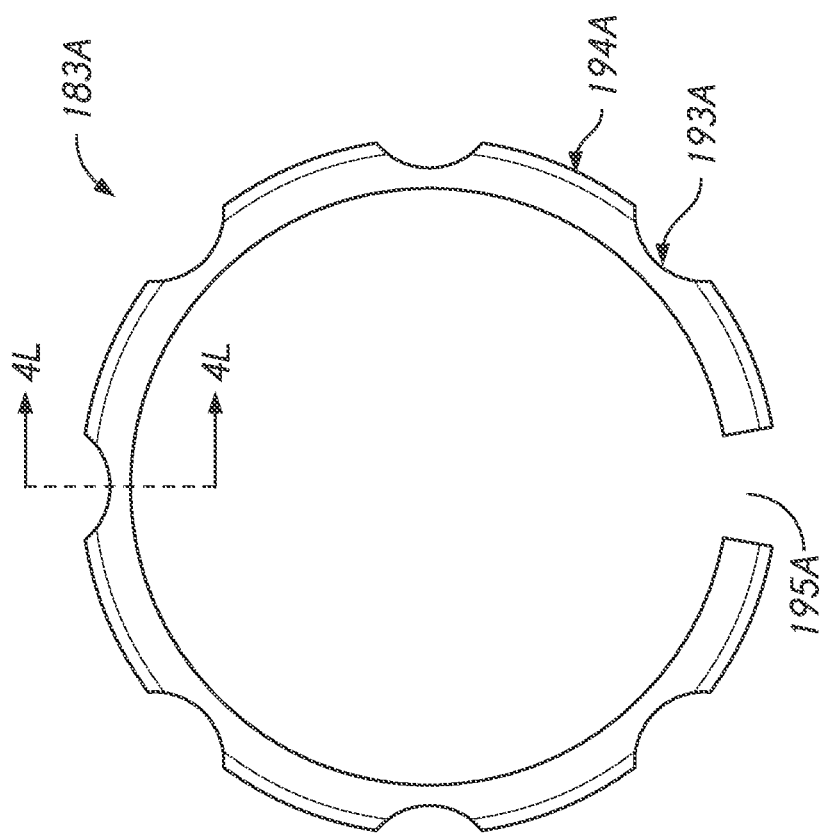
FIG. 4K is a schematic top plan view of a snap ring shown in FIGS. 4F-4J.

FIG. 4K is a schematic top plan view of the snap ring 183A shown in FIGS. 4F-4J. FIG. 4L is a schematic side sectional view of a portion of the snap ring 183A taken along section 4L-4L. As shown in FIG. 4K, the snap ring 183A can comprise a partially annular undulating ring. For example, the ring 183A can comprise thicker portions 194A alternately disposed between laterally thinner portions 193A. As shown, the thinner portions 193A can comprise concave outer surfaces, and the thicker portions 194A can comprise convex outer surfaces, such that an inflection point or discontinuity is disposed between the portions 193A, 194A. Further, a gap 195A can be disposed between opposing ends of the ring 183A to define the partially annular, undulating structure. As shown in FIG. 4L, a thickness t of the ring 183A may be generally constant across its path length in some embodiments.

Beneficially, the undulating shape of the snap ring 183A can be configured to ensure a relatively constant insertion force upon insertion of the reverse articular body 184A into the anchor 108B across a range of sizes. For example, a first humeral anchor 108B can have a recess 216B of a first size. A first snap ring 183A can be sized to engage the 300B of the first humeral anchor 108B. A second humeral anchor 108B can have a recess 216B of a second size larger than the first size. A second snap ring 183A can be sized to engage the 300B of the second humeral anchor 108B. In a typical annular snap-ring, the larger size snap ring would be more flexible and would be insertable under a lower force. The smaller snap ring would be more rigid and would requires a higher insertion force. Similarly, the larger snap ring would be subject to dislodgement under a lower load than the smaller snap ring. The undulating design provides a more uniform insertion force for an insert 161 with a smaller snap ring and for an insert 161 with a larger snap ring. Similarly, the undulating snap ring provides a more consistent dislodgement force for different sizes. This more uniform performance provides more consistency and familiarity among a kit of inserts 161.

Figure 5B:
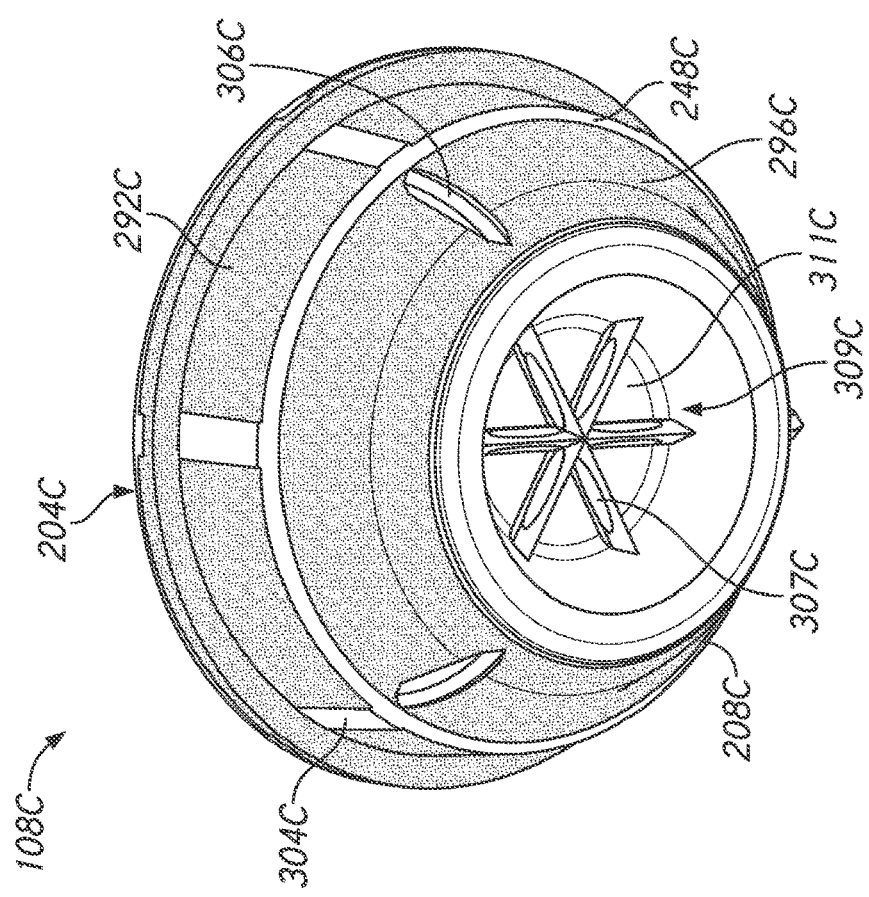
FIG. 5B is a schematic bottom perspective view of the anchor of FIG. 5A.
Figure 5A:
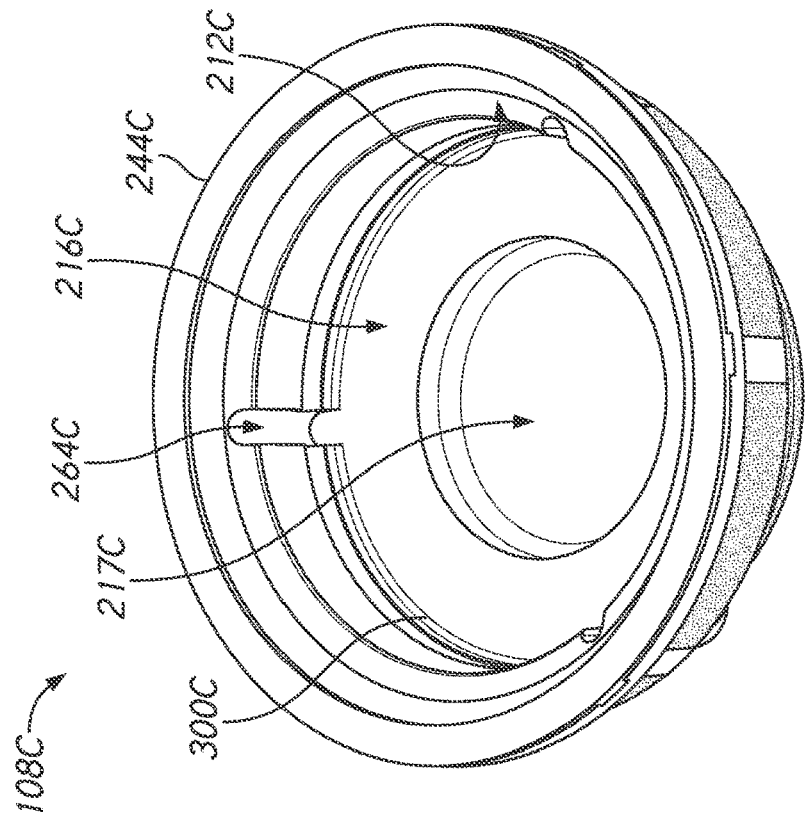
FIG. 5A is a schematic top perspective view of a bowl-shaped stemless humeral anchor, according to another embodiment.

Turning to FIGS. 5A-5C, another embodiment of a bowl-shaped stemless humeral anchor 108C is illustrated. FIG. 5A is a schematic top perspective view of the bowl-shaped stemless humeral anchor 108C. FIG. 5B is a schematic bottom perspective view of the anchor 108C of FIG. 5A. FIG. 5C is a schematic side sectional view of the anchor 108C of FIG. 5A. Unless otherwise noted, the components of FIGS. 5A-5C may be the same as or generally similar to like numbered components of FIGS. 1A-4E, with the reference numerals appended with the letter "C." For example, as with FIGS. 4-4E, the anchor 108C can comprise a bowl-shaped anchor. As with FIGS. 4-4E, the anchor 108C can comprise a monolithic body. Unlike the embodiment of FIGS. 4-4E, however, the anchor 108C includes a second end portion 208C that is enclosed. For example, as shown in FIG. 5B, a lower wall 311 can be provided at the second end portion 208C to enclose the anchor 108C such that bone is not disposed within the anchor 108C. In FIGS. 4-4E, the second end 208B comprises an opening. The opening in the second end 208B can be enclosed with a separate component. As shown in FIG. 5B, a plurality of second fins 307C can be provided proximal the second end 208B and disposed within a cavity 309C at the second end 208C. As shown, the fins 307C can be disposed radially outward (for example, in spoke-like fashion) from a central portion and can extend to an inner wall of the cavity 309C. The second fins 307C can provide further anti-rotation capabilities for the anchor 108C. Furthermore, the cavity 309C can provide space between adjacent fins 307C so as to enable bone ingrowth between the fins 307C. As compared with the anchor 108B of FIGS. 4-4E, in FIGS. 5A-5C, the second tapered portion 296C can be tapered at a higher angle as compared with the portion 296B, which can reduce the volume of bone to be removed. In various embodiments, for example, the tapered portion 296C can have a taper at an angle in a range of 1 to 15 degrees, or in a range of 2 to 10 degrees, e.g., about 5 degrees. This can simplify the procedure and also can preserve bone stock for subsequent procedures.

Moreover, as shown in FIG. 5C, the shoulder 215C can extend farther inwardly than the shoulder 215B, so as to define a second cavity 217C disposed below or distal the cavity 216C (also called a first cavity). As explained in more detail herein, the second cavity 217C can be sized and shaped to receive a portion of coupler 168A configured to enable the anchor 108C to convert from a reverse reconstruction to an anatomical reconstruction. Although not illustrated, a reverse articular component similar to the component 180A may be engaged with the interior surface 212C of the anchor 108C in a manner similar to that described above in connection with FIGS. 4-4K.

Figure 5E:
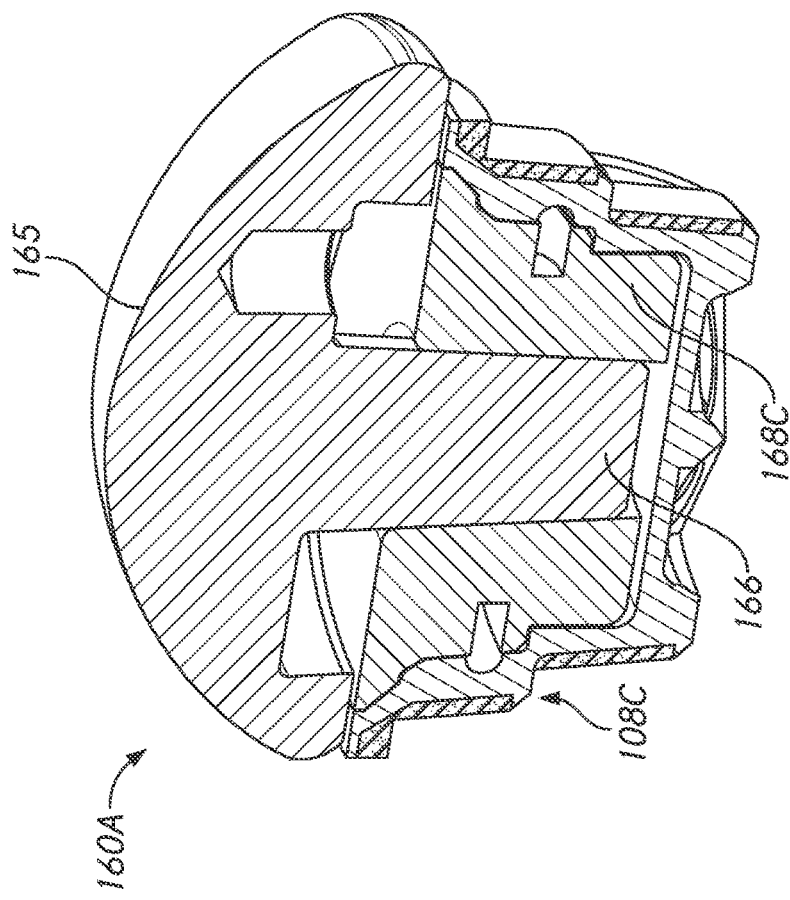
FIG. 5E is a schematic perspective sectional view of the component of FIG. 5D.
Figure 5D:
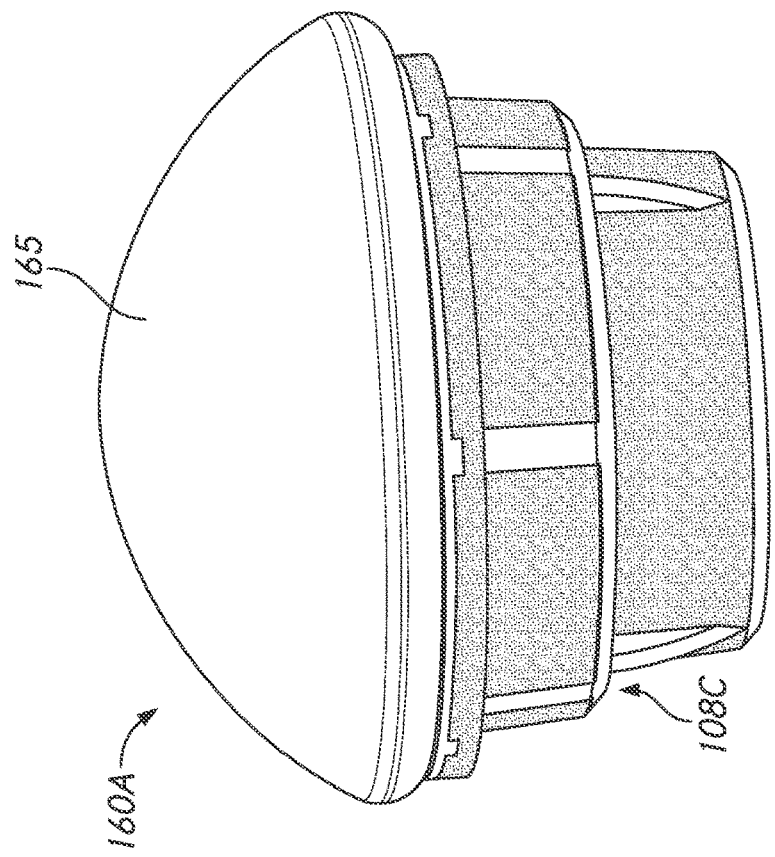
FIG. 5D is a schematic side view of the anatomical articular component connected to the stemless anchor of FIGS. 5A-5C.

FIGS. 5D-5H illustrate an embodiment in which the stemless anchor 108C can be configured for use with an anatomical articular component 160A. In particular, FIG. 5D is a schematic side view of the anatomical articular component 160A connected to the stemless anchor 108C of FIGS. 5A-5C. FIG. 5E is a schematic perspective sectional view of the component 160A of FIG. 5D. FIG. 5F is a schematic bottom perspective view of an articular body 164A, according to some embodiments. FIG. 5G is a schematic top perspective view of a coupler 168A, according to some embodiments. FIG. 5H is a schematic bottom perspective view of the coupler 168A of FIG. 5G. Unless otherwise noted, components related to the articular component 160A may be the same as or generally similar to like-numbered components of FIG. 2A, but appended with the letter "A."

As explained above, the anchor 108C can be used in conjunction with a reverse anatomical articular component 180A, in a manner similar to that explained above. Beneficially, the anchor 108C may also be used in conjunction with an anatomical component 160A for use in an anatomical shoulder reconstruction. For example, the anatomical articular component 160A can include an articular body 164A and a coupler 168A, which may be generally similar to the articular body 164 and coupler 168 of FIG. 2A unless otherwise noted. As shown in FIGS. 5E and 5F, the articular body 164A can comprise a spherical head portion 165 having a convex, generally spherical surface profile. The articular body 164A can further include an elongate member 166 extending from the spherical head portion 165.

Turning to FIGS. 5G and 5H, the coupler 168A can comprise a proximal surface 167, a distal surface 169, and a hole 163 extending from the proximal surface 167 towards the distal surface 169. In the illustrated embodiment, the hole 163 comprises a through hole but in other embodiments the hole 163 can comprise a blind hole. As shown in FIG. 5E, the elongate member 166 of the articular body 164A can be inserted into the hole 163 to connect and align the articular body 164A with the coupler 168A. Moreover, as shown in FIGS. 5G-5H, in some embodiments, a locking device 188' can be used to connect the coupler 168A to corresponding interior surfaces 212C of the anchor 108C. For example, a locking ring (not shown) may be disposed in an outer groove 190 to secure the coupler 168A to the anchor 108C. Upper and lower ridges 189, 191 can be used to engage with the corresponding slots of the anchor 108C, and can limit relative rotation between the coupler 168A and the anchor 108C.

Figure 5J:
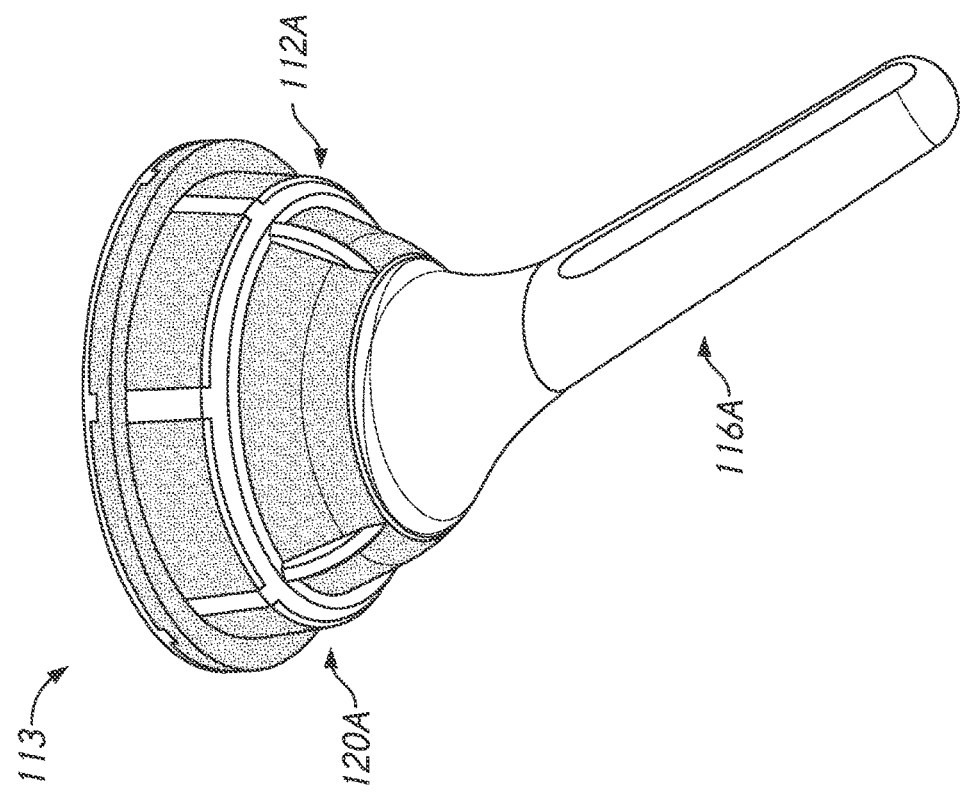
FIG. 5J is a rear perspective view of the stemmed humeral anchor of FIG. 5I.
Figure 5I:
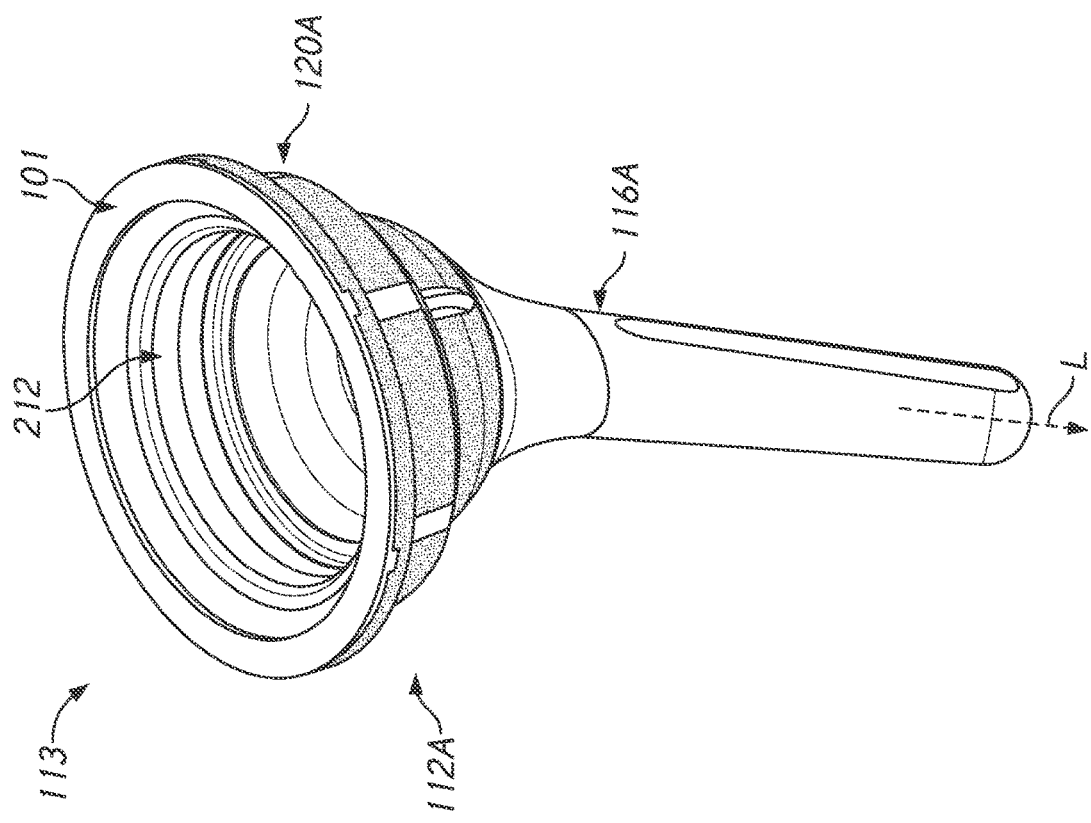
FIG. 5I is a front perspective view of a stemmed humeral anchor, according to one embodiment.

Turning to FIGS. 5I-5J, one embodiment of a stemmed humeral anchor 112A is illustrated. FIG. 5I is a front perspective view of the stemmed humeral anchor 112A, according to one embodiment. FIG. 5J is a rear perspective view of the stemmed humeral anchor 112A of FIG. 5I. The components of the stemmed humeral anchor 112A can be the same as or generally similar to the anchor 112 shown in FIG. 2A, with the components appended with the letter "A." For example, as with FIG. 2A, the anchor 112A can comprise a diaphysis portion 116A (or stem) and a metaphysis portion 120A integrally and monolithically formed with the diaphysis portion 116A. Beneficially the metaphysis portion 120A of the anchor 112A can have interior and exterior surfaces that are generally similar to the anchor 108C described and illustrated above. Thus, because the interior and exterior surfaces of the metaphysis portion 120A may be similar to the surfaces of the anchor 108C, the inserts 161 shown in FIG. 2A can be inserted to provide a full arthroplasty system for both reverse and anatomical shoulder replacement procedures, and for both stemless and stemmed reconstructions. For example, both the anatomic articular component 160 and the reverse articular component 180 of FIG. 2A can be inserted into the diaphysis portion 120A.

In various embodiments, the diaphysis portion 116A or stem can be disposed along a longitudinal axis disposed at an angle L to a planar surface 101 of an end of the metaphysis portion 120A. This angle L is sometimes referred to as inclination angle. The kit 100 of FIG. 2A can comprise stemmed anchors 112A having a plurality of sizes, and a plurality different angles L. For example, in some embodiments, the stemmed anchors 112A can be disposed at an angle L in a range of 120 degrees to 150 degrees to the planar surface. For example, the kit 100 can comprise at least one anchor 112A having an angle L in a range of 130 degrees to 140 degrees, e.g., about 135 degrees, and at least another anchor 112A having an angle L in a range of 140 degrees to 150 degrees, e.g., about 145 degrees. In some embodiments, the anchor 112A to be selected by the clinician can be patient-specific.

Figure 5K:
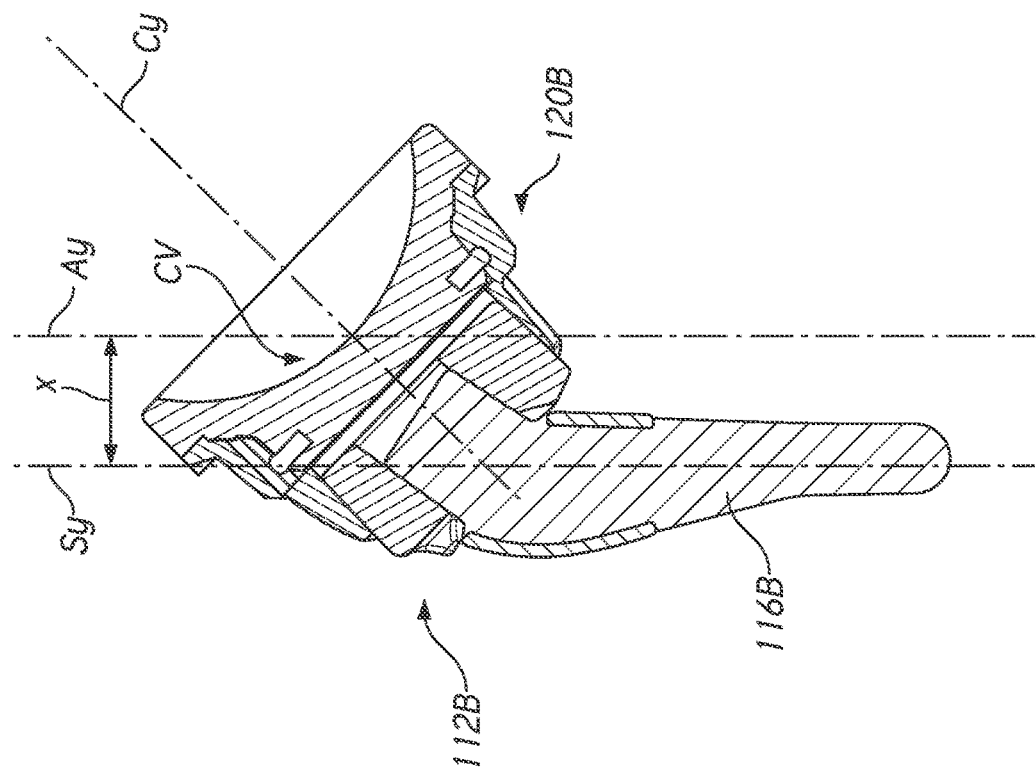
FIG. 5K is a schematic side view of a stemmed anchor having a diaphysis portion and a metaphysis portion integrally and monolithically formed with the diaphysis portion.

FIG. 5K is a schematic side view of a stemmed anchor 112B having a diaphysis portion 116B (or stem) and a metaphysis portion 120B integrally and monolithically formed with the diaphysis portion 116B. The stemmed anchor 112B can be similar to the stemmed anchor provided by assembling the components shown in FIG. 4E. As shown in FIG. 5K, the metaphysis portion 120B can be configured to interact or support any of the inserts 161 and anchors disclosed herein. In various embodiments, depending on the size of the patient or the extent of bone injury, it may be desirable to provide pre-determined humeral offsets between the humerus H and various portions of the anchor, in order to accommodate different sizes for the implant.

As shown in FIG. 5K, for example, the stem or diaphysis portion 116B can comprise a longitudinal stem axis $S_y$ extending along a longitudinal axis of the diaphysis portion 116B. The metaphysis portion 120B can comprise interior surfaces similar to those described above in connection with the stemless anchors described above. The diaphysis portion 116B can comprise a concave surface CV and an axis $A_y$ passing through a central point on the concave surface CV. The diaphysis portion 116B may have a central axis $C_y$ passing perpendicular to the concave surface CV. A distance between the axes $A_y$ and $S_y$ can be based on the anatomy of the patient. Thus, in various embodiments, the clinician can select a size of the anchors based at least in part on a distance between an axis of the stem ($S_u$) and an axis ($A_y$) that intersects the central axis $C_y$ of the anchor. In various embodiments, the clinician can design the stemmed anchor 112B to provide a desired distance between an axis of the stem ($S_u$) and an axis ($A_y$) that intersects the central axis $C_y$ of the anchor. In some embodiments, the clinician can select an anchor based at least in part on a distance between an axis of the stem ($S_u$) and the central lower point of the concave surface (CV) of the device or based on an axis extending through a geometric center of the metaphysis portion 120B and perpendicular to a proximal plane thereof.

FIGS. 6A-6F illustrate another embodiment of a stemless humeral anchor 104 configured for use in both anatomical and reverse anatomical shoulder arthroplasty procedures. The stemless humeral anchor 104 can comprise the same humeral anchor 104 as that shown in FIGS. 2A-2B. Further, unless otherwise noted, other components of FIGS. 6A-6F may be the same as or generally (e.g., functionally) similar to like-numbered components of FIGS. 3-5J, but without any letters appending the reference numerals. As explained above in connection with FIG. 2A, the anchor 104 of FIGS. 6A-6F can comprise a bowl-shaped stemless anchor with a finned distal portion which can beneficially be used in stemless procedures for reducing or minimizing bone less, as the diameter or width of the distal portion 105 may be less than the diameter or width of the proximal portion 107.

Figure 6B:
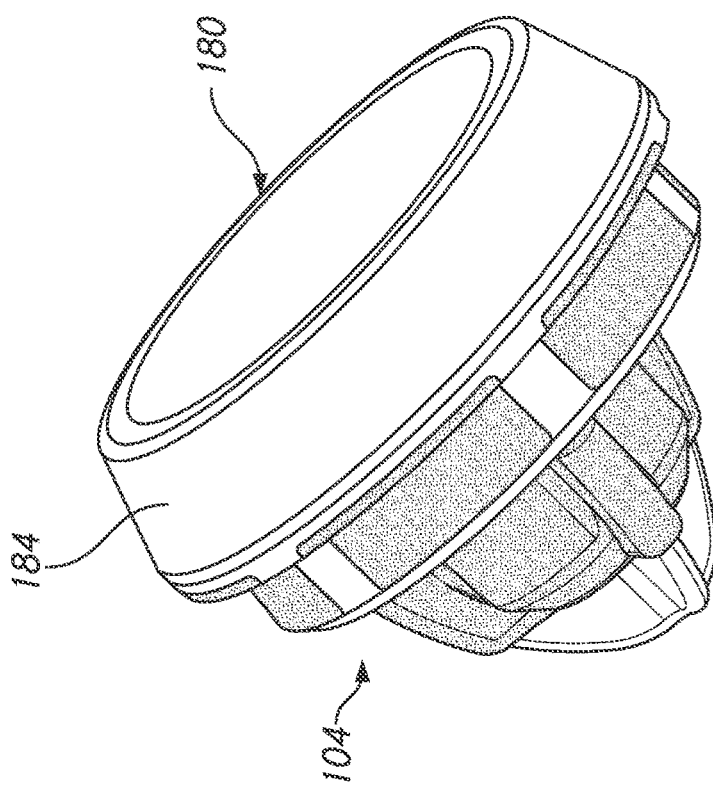
FIG. 6B is a schematic perspective view of a prosthesis comprising the humeral anchor of FIG. 6A connected to a reverse articular component.
Figure 6A:
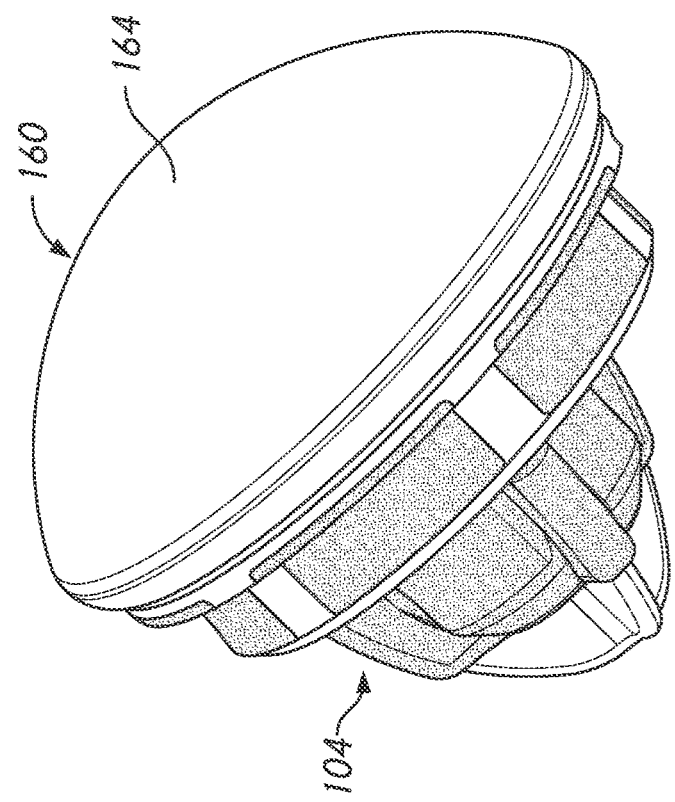
FIG. 6A is a schematic perspective view of a prosthesis comprising the humeral anchor of FIG. 2A connected to an anatomical articular component.

FIG. 6A is a schematic perspective view of a prosthesis comprising the humeral anchor 104 connected to an anatomical articular component 160 comprising an anatomical body 164 with a convex surface. As explained above, the articular component 160 of FIG. 6A can be used in an anatomical shoulder replacement procedure. In such procedures, the anatomical body 164 can engage with a concave surface coupled to the glenoid surface of the patient.

By contrast, FIG. 6B is a schematic perspective view of a prosthesis comprising the humeral anchor 104 connected to a reverse articular component 180 comprising a reverse articular body 184 having a concave surface. As explained above, the reverse articular component 180 of FIG. 6B can be used in a reverse anatomical shoulder replacement procedure. In such procedures, the reverse articular body 184 can engage with a convex surface coupled to the glenoid surface of the patient. Accordingly, the anchor 104 can be used in both anatomical and reverse anatomical procedures.

Figures 6C, 6D:
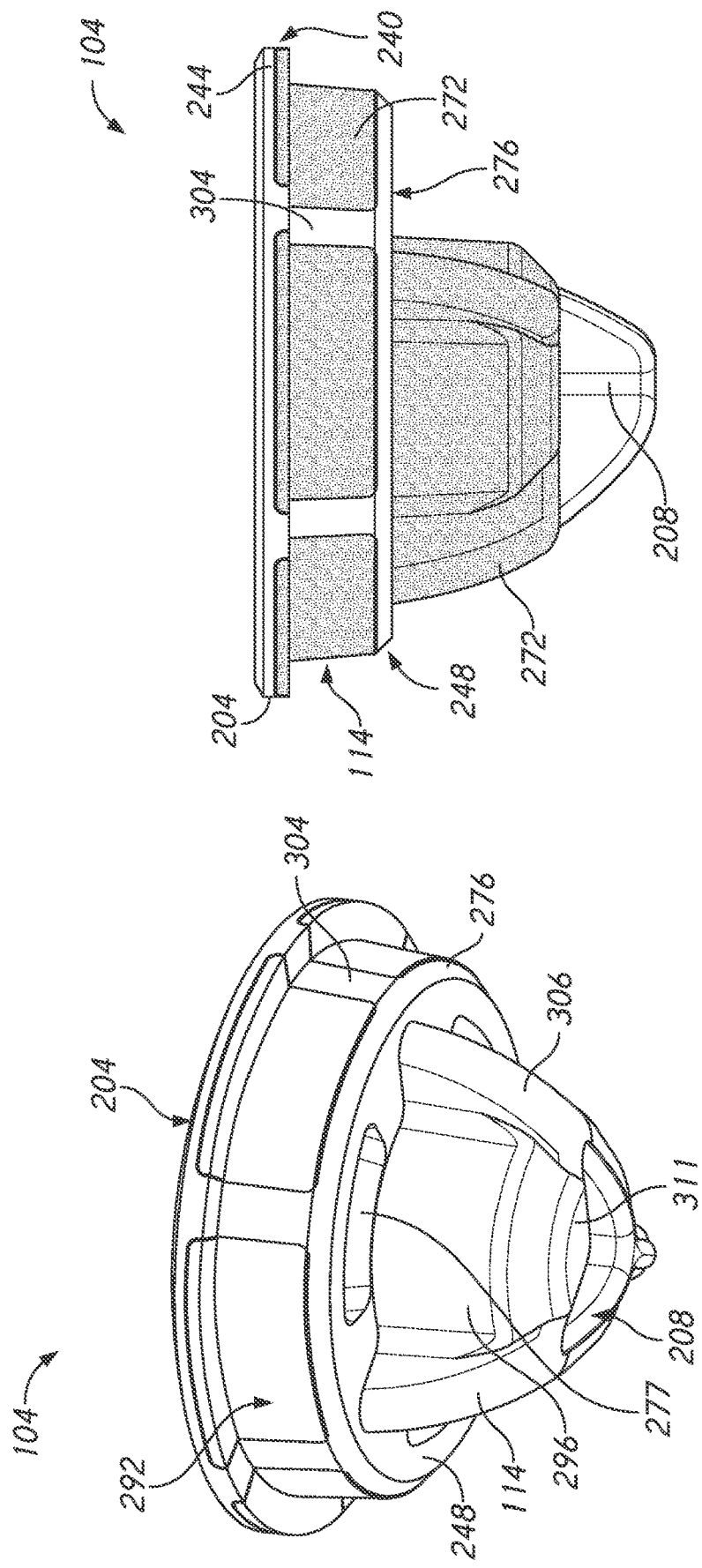
FIG. 6C is a schematic perspective view of the humeral anchor of FIGS. 6A-6B having a first size.
FIG. 6D is a schematic perspective view of the humeral anchor having a second size different than the first size.

FIG. 6C is a schematic perspective view of the humeral anchor 104 of FIGS. 6A-6B having a first size. FIG. 6D is a schematic perspective view of the humeral anchor 104 having a second size different than (e.g., smaller than) the first size. FIG. 6E is a top plan view of the humeral anchor 104 of FIGS. 6A-6B. FIG. 6F is a schematic side sectional view of the humeral anchor 104, taken along section 6F-6F. The kit 100 can comprise a plurality of the anchors 104 in a corresponding plurality of different sizes. The anchor 104 shown in FIGS. 6C-6D can comprise an exterior surface 114 having a plurality of struts 304, a porous surface 272, one or more non-porous edges 276, and a collar 244, which may function in a generally similar manner to like-numbered components of FIGS. 3-4E. Similarly, the anchor 104 can comprise a first portion 292 and a second portion 296 at the exterior surface 114. In some embodiments, the first and second portions 292, 296 may not be tapered (e.g., may be generally cylindrical) or may be only slightly tapered. The first and second portions 292, 296 can be configured to engage with humeral bone layers upon insertion into the anatomy.

Unlike the embodiment of FIGS. 3-4E, however, the anchor 104 may comprise a finned anchor, as opposed to a bowl-shaped anchor 108. As shown in FIGS. 6C-6D, for example, the lateral projection 248 can position the second portion 296 to be laterally inset from the first portion 292. One or a plurality of fins 306 can extend radially outwardly from the second portion 296. As shown the fins 306 can be thicker near the lateral projection 248 that at or near the second end 208. The fins 306 can serve as anti-rotation features for the anchor 104. Further, the anchor 104 can comprise one or more apertures 277. The apertures 277 can be used to remove the anchor 104 in the event of problems. For example, if the anchor 104 is to be removed, a tool can be inserted through the aperture(s) 277 to cut soft tissue disposed distal the aperture(s) 277 to assist in freeing the anchor 104 from the humerus H.

Turning to FIGS. 6E and 6F, the lateral projection 248 may serve to define a second distal recess 217 that is below or distal to the first recess 116. As shown in FIG. 6F, for example, the first recess 216 may be wider and larger than the second recess 217. As explained above, in some embodiments, the first recess 216 may be defined by generally cylindrical or only slightly tapered walls. Similarly, the second recess 217 may be defined by generally cylindrical or only slightly tapered walls. As explained herein, in some embodiments, the second recess 217 can be sized and shaped to receive a portion of the coupler 160 to convert the reverse anatomical reconstruction device of FIG. 6B to the anatomical reconstruction device of FIG. 6A. A tapered surface 260 disposed on the exterior surface 114 can taper the diameter of the anchor 104 such that the diameter or width is smaller at the second end 208 than at the first end 204.

FIGS. 7A-7E illustrate another embodiment of a stemless humeral anchor 108 configured for use in both anatomical and reverse anatomical shoulder arthroplasty procedures. The stemless humeral anchor 108 can comprise the same humeral anchor 108 as that shown in FIG. 2A. Further, unless otherwise noted, other components of FIGS. 7A-7E may be the same as or generally (e.g., functionally) similar to like-numbered components of FIGS. 3-6F, but without any letters appending the reference numerals. As explained above in connection with FIG. 2A, the anchor 108 of FIGS. 7A-7E can comprise a bowl-shaped anchor in which the larger distal portion 105 of the humeral anchor 108 can serve a bone-filling function, as explained above.

Figure 7A:
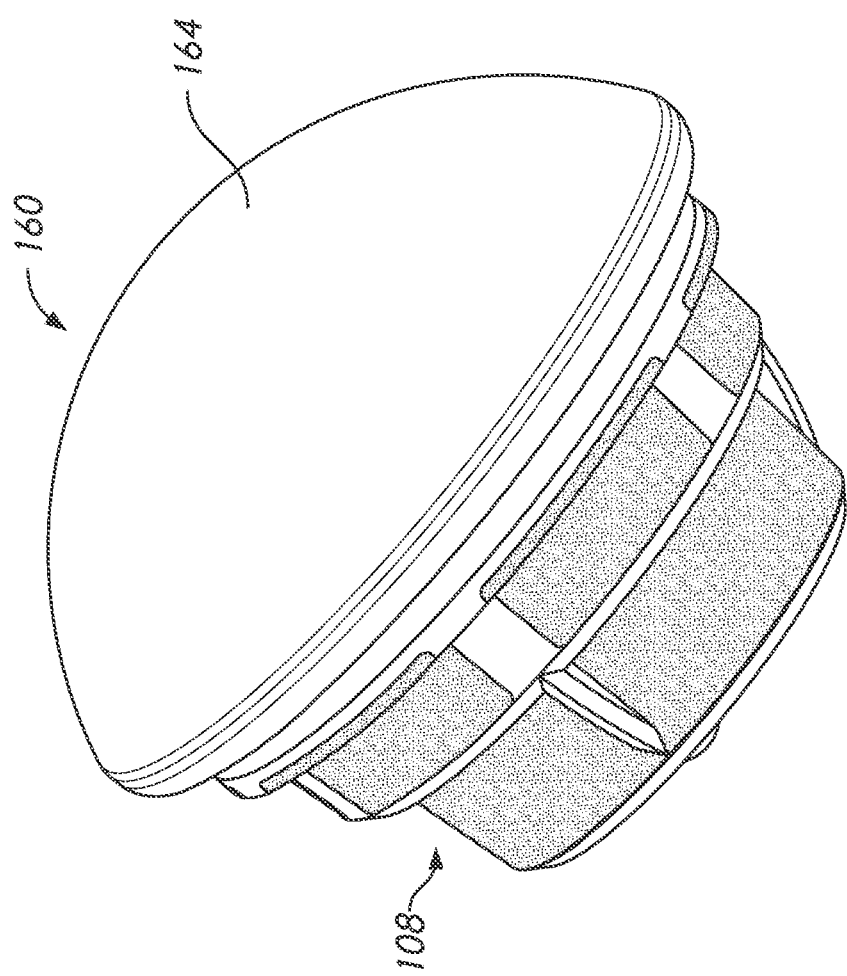
FIG. 7A is a schematic perspective view of a prosthesis comprising the bowl-shaped humeral anchor of FIG. 2A connected to an anatomical articular component.
Figure 7C:
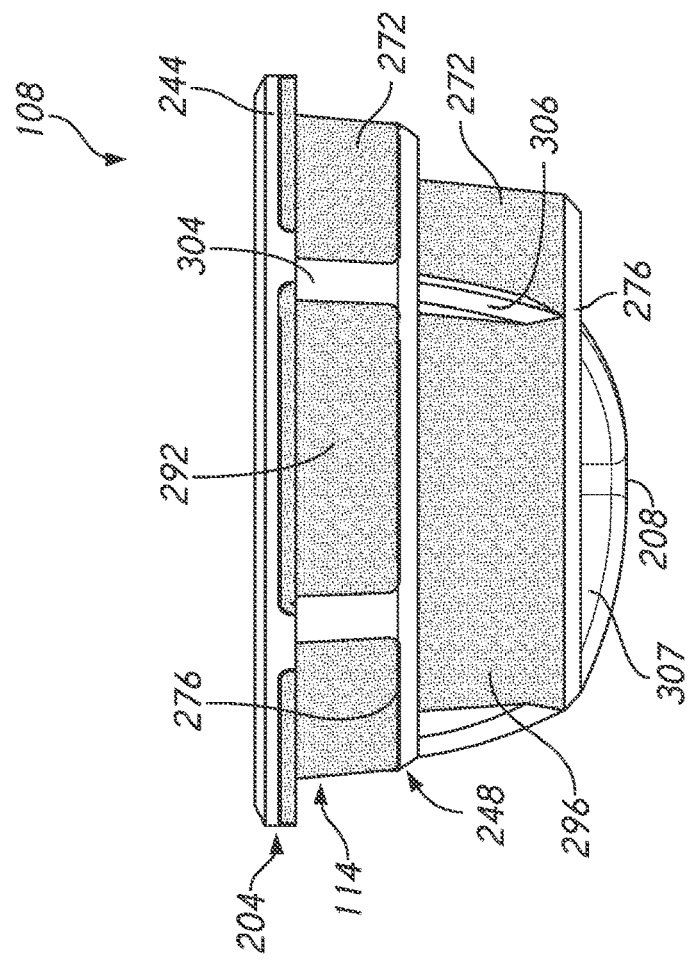
FIG. 7C is a schematic side view of the humeral anchor of FIGS. 7A-7B.

FIG. 7A is a schematic perspective view of a prosthesis comprising the humeral anchor 108 connected to an anatomical articular component 160 comprising an anatomical body 164 with a convex surface. As explained above, the articular component 160 of FIG. 7A can be used in an anatomical shoulder replacement procedure. In such procedures, the anatomical body 164 can engage with a concave surface coupled to the glenoid surface of the patient.

Figure 7B:
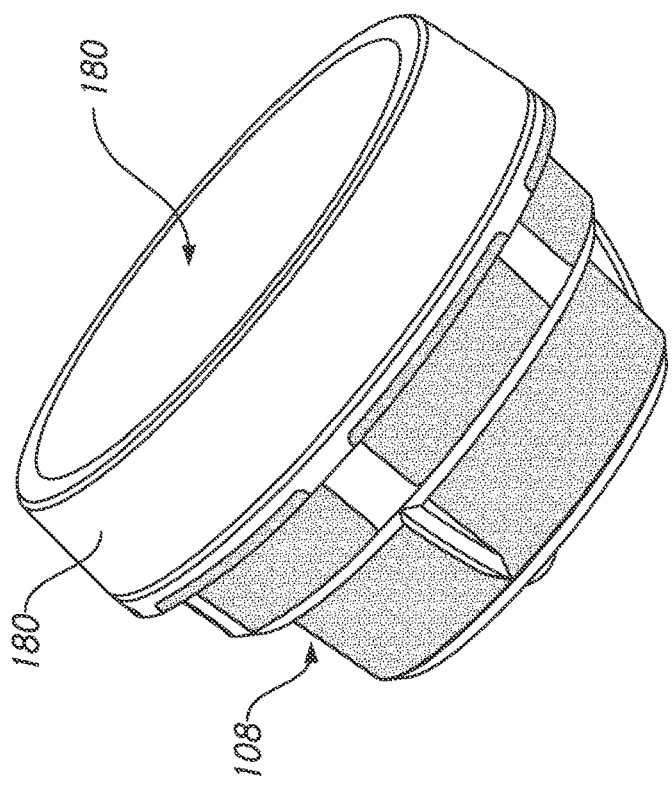
FIG. 7B is a schematic perspective view of a prosthesis comprising the bowl-shaped humeral anchor of FIG. 7A connected to a reverse articular component.

By contrast, FIG. 7B is a schematic perspective view of a prosthesis comprising the humeral anchor 108 connected to a reverse articular component 180 comprising a reverse articular body 184 having a concave surface. As explained above, the reverse articular component 180 of FIG. 6B can be used in a reverse anatomical shoulder replacement procedure. In such procedures, the reverse articular body 184 can engage with a convex surface coupled to the glenoid surface of the patient. Accordingly, the anchor 108 can be used in both anatomical and reverse anatomical procedures.

Figure 7E:
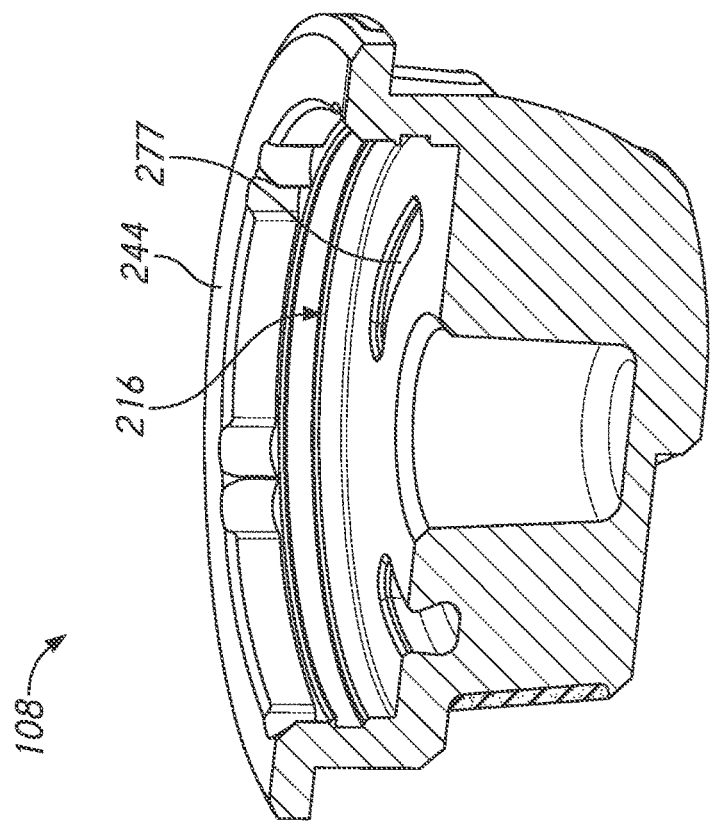
FIG. 7E is a schematic perspective side sectional view of the humeral anchor of FIG. 7C.
Figure 7D:
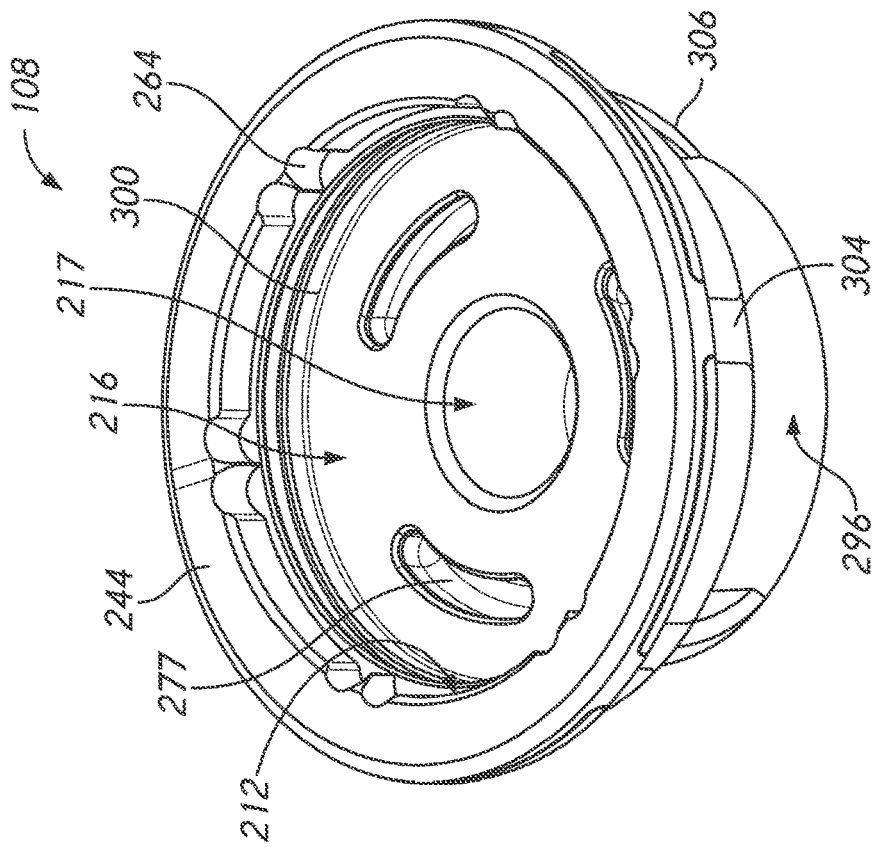
FIG. 7D is a schematic top perspective view of the humeral anchor of FIG. 7C.
Figure 7G:
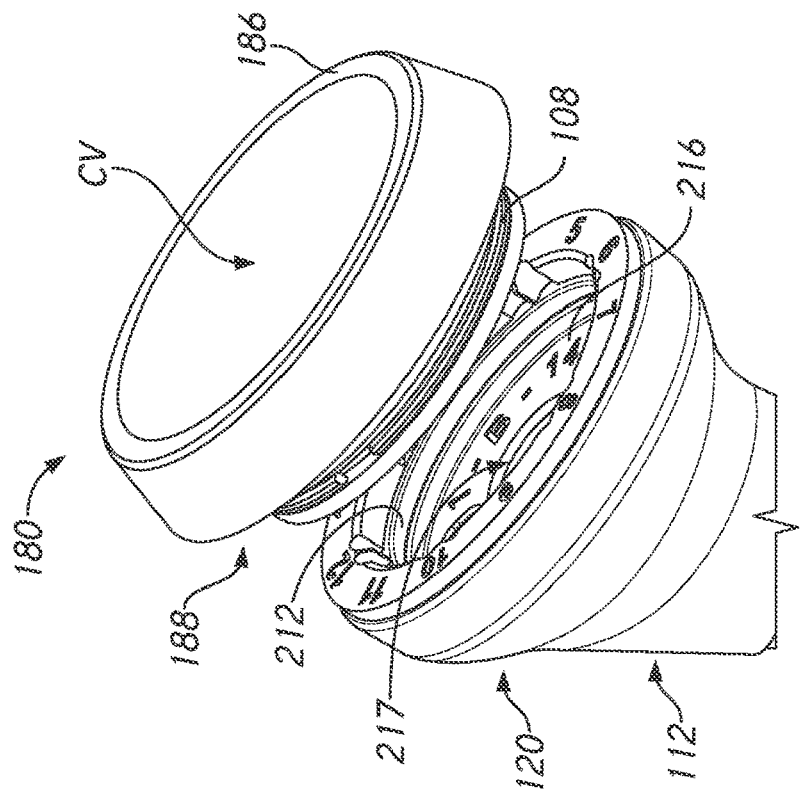
FIG. 7G is a rear perspective view of the stemmed humeral anchor of FIG. 7F.
Figure 7F:
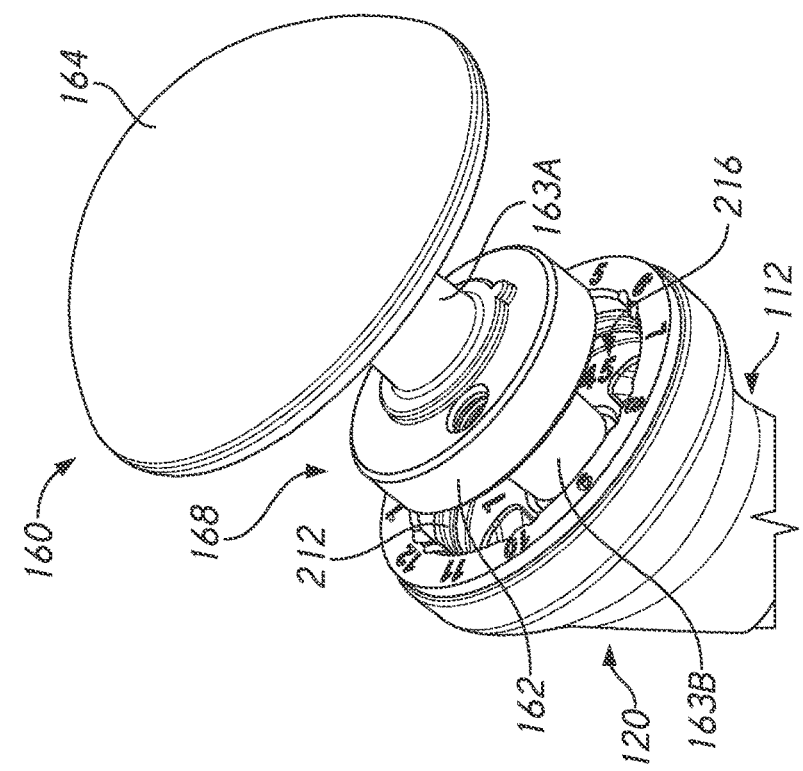
FIG. 7F is a front perspective view of a stemmed humeral anchor, according to one embodiment.

FIG. 7C is a schematic side view of the humeral anchor 108 of FIGS. 7A-7B. FIG. 7D is a schematic top perspective view of the humeral anchor 108 of FIG. 7C. FIG. 7E is a schematic perspective side sectional view of the humeral anchor 108 of FIG. 7C. As with the embodiment of FIGS. 3-6F, the embodiment of FIGS. 7A-7E can include an exterior surface 114 that includes a plurality of struts 304, a porous surface 272, one or more non-porous edges 276, and a collar 244, which may function in a generally similar manner to like-numbered components of FIGS. 3-4E. Similarly, the anchor 108 can comprise a first portion 292 and a second portion 296 at the exterior surface 114. In some embodiments, the first and second portions 292, 296 may not be tapered (e.g., may be generally cylindrical) or may be only slightly tapered. The first and second portions 292, 296 can be configured to engage with humeral bone layers upon insertion into the anatomy as explained herein.

Furthermore, a plurality of fins 306 can be disposed along the second portion 296. The fins 306 can be spaced circumferentially from one another. In addition, a plurality of second fins 307 can be disposed at the second end 208. The fins 306, 307 can serve to secure the anchor 108 to the bone tissue and to prevent rotation of the anchor 108. As shown in FIG. 7C, the second end 208 of the anchor 108 may be closed in some embodiments. Furthermore, in FIG. 7D, the interior surface 212 can comprise the apertures 277 the groove 300, and the slots 264, as explained above. In addition, as with the embodiment of FIGS. 6A-6F, the anchor 108 can comprise a first recess 216 and a second recess 217 distal or below the first recess 216. As explained above, the first recess 216 can be sized and shaped to receive an insert 161. The second recess 217 can be sized and shaped to receive a portion of a coupler 168 for converting the reverse anatomical device of FIG. 7B to the anatomical device of FIG. 7A. The portions 292, 296 may taper inwardly, such that the second end 208 is narrower than the first end 204. As compared with the anchor 104, however, the second end 208 of the anchor 108 may be larger than the second end 208 of the anchor 104.

Turning to FIGS. 7F-7G, one embodiment of a stemmed humeral anchor 112 is illustrated. The stemmed humeral anchor 112 of FIGS. 7F-7G may be the same as the stemmed humeral anchor 112 of FIG. 2A. FIG. 7F is a front perspective view of the stemmed humeral anchor 112, according to one embodiment. FIG. 7G is a rear perspective view of the stemmed humeral anchor 112 of FIG. 7F. The components of the stemmed humeral anchor 112A can be the same as or generally similar to the anchor 112 shown in FIG. 2A, with the components appended with the letter "A." As with FIG. 2A, the metaphysis portion 120 of the anchor 112 can have interior and exterior surfaces 112, 114 that are generally similar to the anchor 108 described and illustrated above, which can enable both stemmed and stemless solutions for the kit 100. Thus, because the interior and exterior surfaces 112, 114 of the metaphysis portion 120A may be similar to the surfaces of the anchor 108C, the inserts 161 shown in FIG. 2A can be inserted to provide a full arthroplasty system for both reverse and anatomical shoulder replacement procedures, and for both stemless and stemmed reconstructions. For example, both the anatomic articular component 160 and the reverse articular component 180 of FIG. 2A can be inserted into the diaphysis portion 120.

With respect to the anatomical stemmed device of FIG. 7F, the coupler 168 can comprise a bi-surface (e.g., a bi-cone) adaptor having a middle portion 162 and opposing portions or extensions 163A, 163B extending from opposite sides of the middle portion 162. The proximal extension 163A can be configured to connect to the articular body 164. The distal extension 163B can be configured to be inserted into the second recess 217 of the metaphysis portion 120A. The middle portion 162 can be received within the first recess 216. Further details of the coupler 168 and other variations of couplers including couplers with expandable disc portions for engaging the surface of the stemmed anchor 112 about the first recess 216 are set forth in U.S. Provisional Patent Application No. 62/740,342, filed on Oct. 2, 2018, entitled "MODULAR HUMERAL HEAD," which is incorporated by reference herein in its entirety.

As shown in FIG. 7G, for the reverse anatomical component 180, the locking device 188, which may comprise a snap ring 183 in some embodiments, can be received within the groove 30 to secure at least a portion of the component 180 within the first recess 216. Although the reverse and anatomical components 160, 180 of FIGS. 7F and 7G are illustrated with respect to the stemmed anchor 112, it should be appreciated that, as explained above, the same reverse and anatomical components 160, 180 can be used with the stemless anchors 104, 108.

III. Shoulder Arthroplasty Methods and Instrumentation

The stemless humeral anchors 104, 108, 108B, 108C described herein are configured to be able to receive a portion of an articular component 160, 180 below a humeral resection surface RS. As well, the anchors described herein are configured to allow a surgeon to reverse the articular surfaces of the shoulder while accommodating soft tissue of a wide variety of patients. As discussed elsewhere herein, the humeral anchors 104, 108 108B, 108C enable a surgeon to adapt a patient or a surgical plan from a stemless anchor to a stemmed anchor. The stemmed anchor can be adapted to occupy the same or a larger volume of the cancellous bone beneath the resection surface RS. Although the methods below are discussed in connection with the humerus H, the anchors and the couplers described herein can be deployed in other orthopedic applications such as in implanting a glenosphere in a glenoid, a femoral articular body on an end of a femur (e.g., for hip or knee procedures) or for implanting a tibial articular body at an end of a tibia for a joint procedure.

Figure 8A:
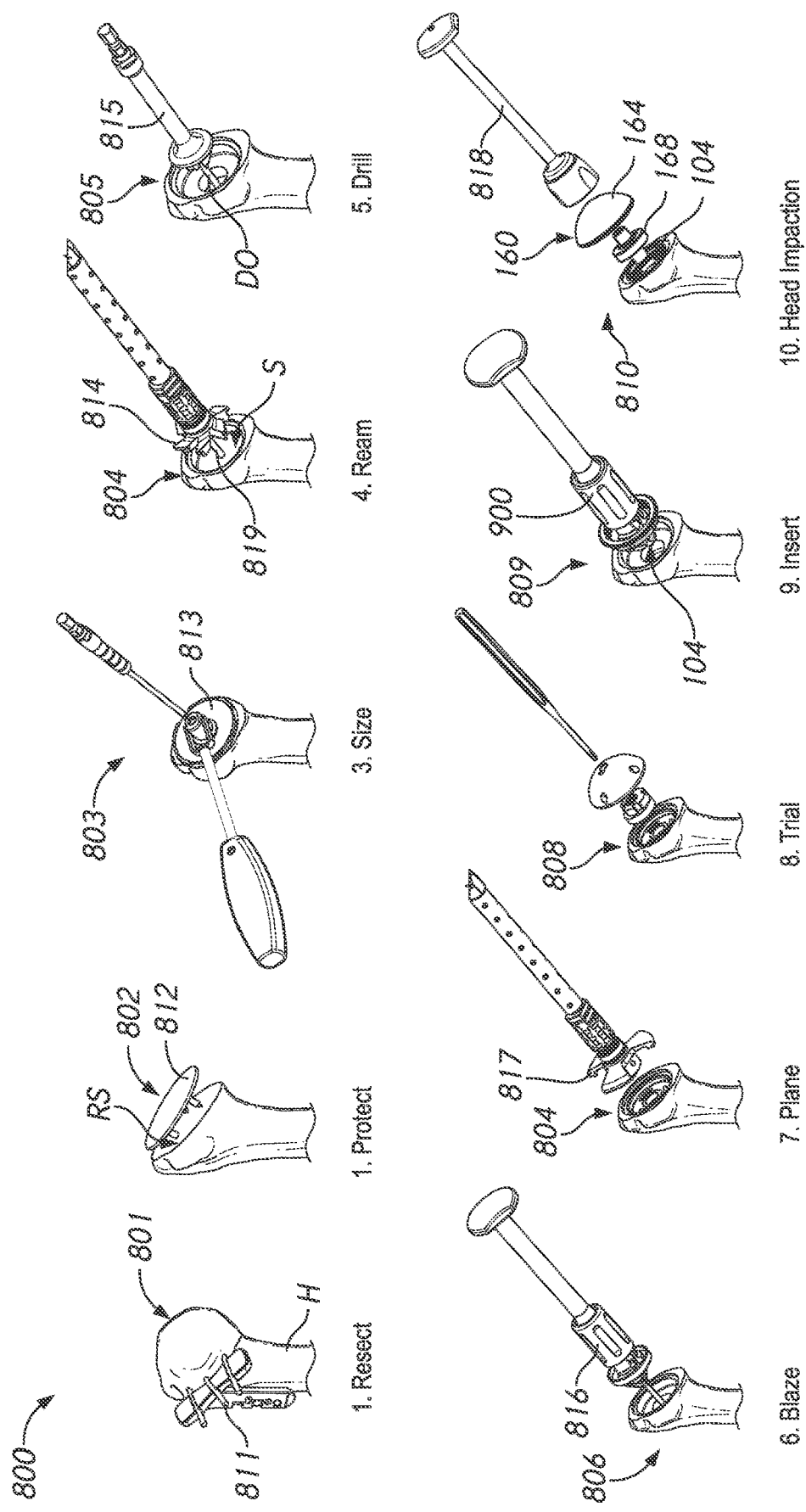
FIG. 8A illustrates a method for performing a shoulder arthroplasty using a stemless anchor described herein in conjunction with an anatomical articular component.

FIG. 8A illustrates a method 800 for performing a shoulder arthroplasty using the bowl-shaped stemless anchor 104 with finned distal portion described herein in conjunction with the anatomical articular component 160 described herein. The method 800 can include a step 801 of resecting a humerus H at a superior or proximal end thereof. The resection can be performed with a surgical guide 811 to create a generally planar surface through the humerus H. The guide 811 can be a generic guide that is supported on a side surface of the humerus H with rigid pins or bone screws. The guide 811 can be a patient specific guide, e.g., any of the patient specific guides disclosed in International Patent Application No. PCT/US2018/041531, which is hereby incorporated by reference herein in its entirety. In a step 802, the resected surface RS can be protected with a plate member 812. The surgeon may be provided with one or more sizing disks 813 to determine a size of the metaphysis in a step 803. The sizing disks 813 can be configured to facilitate visualization of the space between the implant to be implanted and the cortical boundary of the bone.

The sizing disk 813 can also have features that aid in referencing the diaphysis of the humerus H, e.g., one or more apertures for guide pins that assure that the reamed surface (see step 804) in the metaphysis is properly positioned. This is particularly useful if the stemmed anchor 112 is used. Further details of sizing disks 813 and related components to prepare the metaphysis with reference to the diaphysis are discussed in U.S. Provisional Patent Application No. 62/740,257, filed on Oct. 2, 2018, entitled "METAPHYSEAL REFERENCING TECHNIQUE AND INSTRUMENT," which is hereby incorporated by reference herein in its entirety.

In a step 804, the method 800 can include selecting an appropriately sized reamer 814 for the resected humerus H. As illustrated in FIG. 8A, the reamer 814 is configured to produce a generally concave recessed surface S in the resected humerus H. For example, in some embodiments, the size of the reamer 814 can be selected to correspond to the width of the anchor 104 at or near the first end 204, such that the surface S can accommodate the widest portion of the anchor 104.

The reamer 814 is guided over a guidewire 819. The guidewire 819 can be placed by any suitable technique. As noted above, the sizing disk 813 can be used to assure that the guidewire 819 is in the correct position. The resection guide 811 can include or be coupled with a guide device for controlling placement of the guidewire 819. This is discussed in International Patent Application No. PCT/US2018/041531, which is incorporated by reference herein.

The method 800 can proceed to a step 805 in which a distal opening DO is drilled using an appropriate drilling tool 815. The distal opening DO can be sized and shaped to receive the second end 208 of the anchor 104, which may be smaller than the first end 204. In a step 806, the distal opening DO can be further prepared, e.g., blazed with an appropriate blazing tool 816. In one form, blazing involves forming radial channels that are configured to receive the fins 306 that extent outwardly from the anchor 104. The blazing can be performed only below the first recess 216 to form channels disposed below the first recess 216 in order to accommodate the fine 306. In a step 807, the exposed surface(s) of the humerus H can be planarized with a planarizing tool 817. After reaming, an appropriately-sized anchor 104 can be selected for insertion into the prepared resected surface RS of the humerus H. Moving to a step 808, components of the anchor or articular body can be inserted into the resected opening(s) of the humerus H in a trial step.

If the sizing in the trial step is suitable or after the proper size has been determined, in a step 809, the proper size anchor 104 can be inserted into the humerus H using a humeral anchor insertion instrument 900 (see also FIGS. 9A-10D). As explained herein, the anchor 104 can be pushed directly into the humerus H with a non-rotational motion of the anchor 104, e.g., such that the anchor does not rotate relative to the humerus H as it is being inserted. This has several benefits. The bone below the resection surface RS is not milled or is only minimally disrupted by the process of inserting the anchor 104. This is consistent with preserving bone stock for future procedures.

In a step 810, the anatomical articular component 160 can be impacted onto the anchor 104. An impactor 818 can be configured to engage the coupler 168 and the articular body 160 with the inserted anchor 104. The coupler can be any suitable coupler. As discussed herein, as the inserted anchor 104 has a receiving portion that is below the resected surface RS of the resected humerus, the impactor 818 can impact the components of the such that the articular body 164 is flush against the resected surface RS of the resected humerus. Further details of the coupler 168 and variations thereof are discussed in U.S. Provisional Patent Application No. 62/740,342, filed on Oct. 2, 2018, entitled "MODULAR HUMERAL HEAD," which is incorporated by reference herein in its entirety.

Figure 8B:
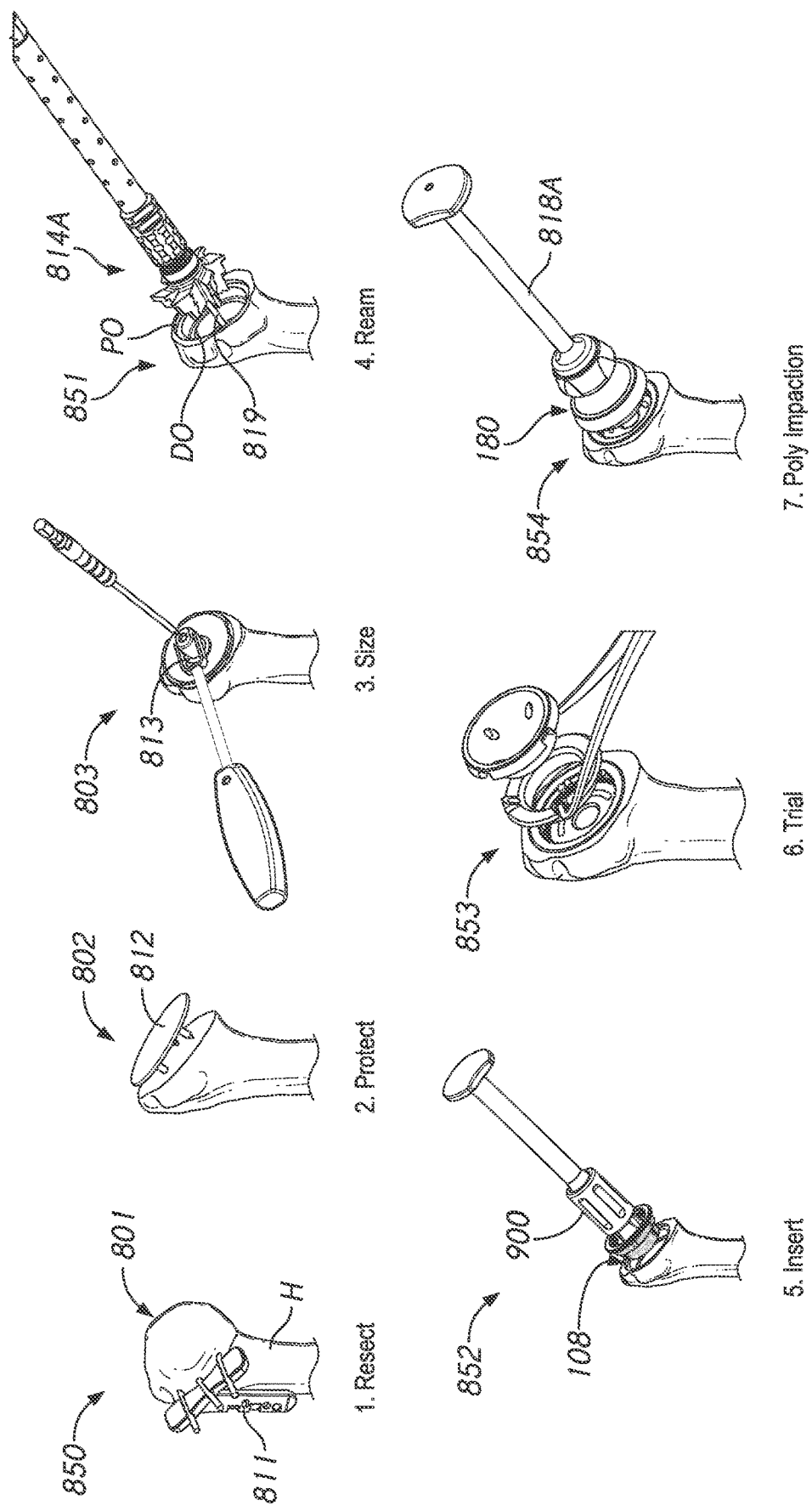
FIG. 8B illustrates a method for performing a shoulder arthroplasty using a bowl-shaped stemless anchor in conjunction with a reverse anatomical articular component, according to another embodiment.

FIG. 8B illustrates a method 850 for performing a shoulder arthroplasty using the bowl-shaped stemless anchor 108 described herein in conjunction with the reverse anatomical articular component 180 described herein. Steps 801, 802, and 803 may be the same as or generally similar to like-numbered steps in FIG. 8A. In step 851, however, the reamer 814A may be selected to create a distal opening DO so as to accommodate the bowl-shaped structure of the second end 208 of the anchor 108.

Figure 8D:
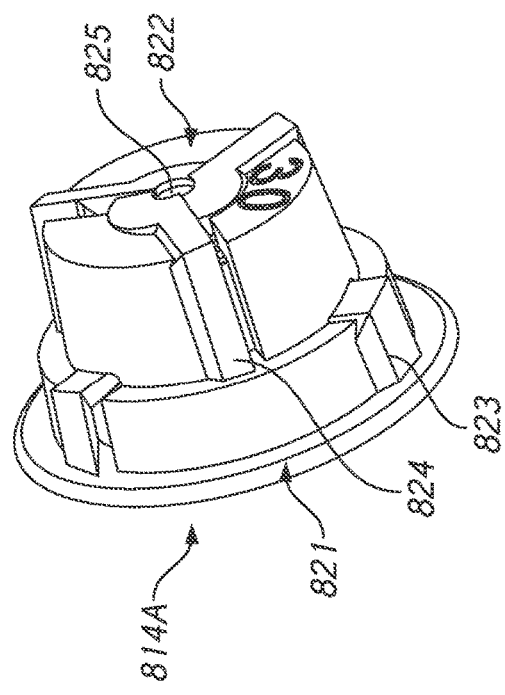
FIG. 8D is a schematic perspective front view of the reamer of FIG. 8C.
Figure 8E:
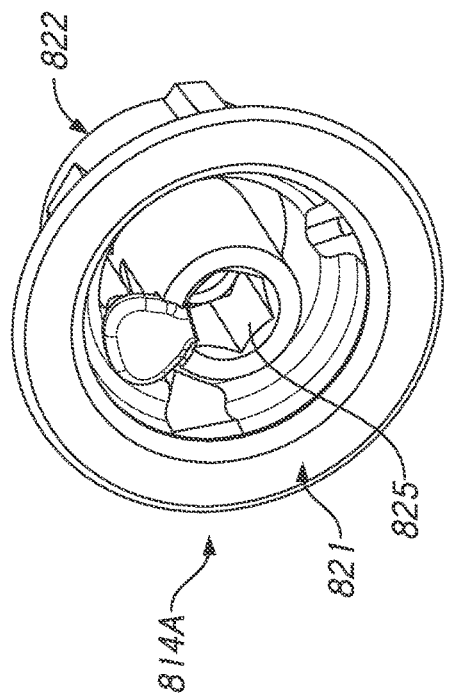
FIG. 8E is a schematic perspective rear view of the reamer of FIG. 8C.
Figure 8C:
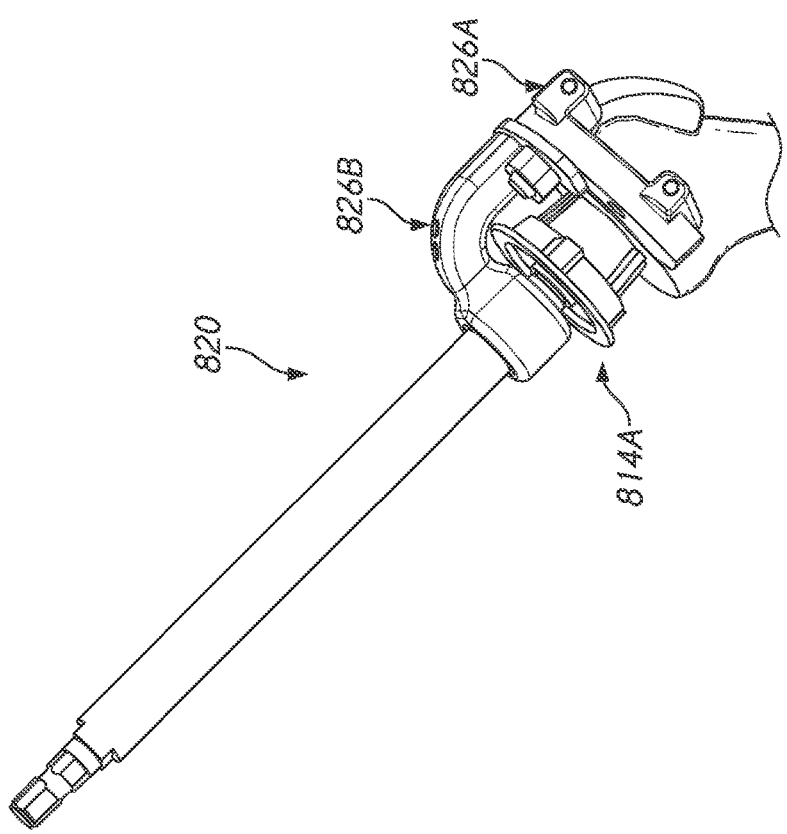
FIG. 8C is a schematic perspective view of a two-stage reamer guided by a patient specific humeral guide, according to some embodiments.

A convenient reaming step can be employed in which the reamer 814A is a two stage reamer. FIG. 8C is a schematic perspective view of the two-stage reamer 814A attached to a shaft 820, which the clinician can manipulate to engage the humerus H with the reamer 814A, according to some embodiments. The reamer 814A can be guided by a humeral guide 826, as shown. The guide 826 can include a portion 826A configured to be pinned to a side surface of the humerus H and a removable portion 826B configured to guide the reamer shaft 820 along an outside surface of the shaft thereof. The guide 826 can be patient specific in one or more aspects. Further details of embodiments of the guide 826 are set forth in International Patent Application No. PCT/US2018/041531, which is hereby incorporated by reference herein for all purposes. The guide 826 can be patient specific. FIG. 8D is a schematic perspective front view of the reamer 814A. FIG. 8E is a schematic perspective rear view of the reamer 814A. The two stage reamer 814A can include a proximal body 821 and a distal body 822 formed with or coupled to the proximal body 821. A first plurality of cutting elements 824 can extend radially outward from the distal body 822. A second plurality of cutting elements 823 can extend radially outward from the proximal body 821. A guidewire lumen 825 can be provided through the reamer 814A, and can be sized and shaped to receive the guidewire 219 described above.

As shown in FIGS. 8D-8E, a lateral dimension (e.g., width, diameter, etc.) of the proximal body 821 can be larger than a lateral dimension of the distal body 822. For example, as shown in FIGS. 8D-8E, the proximal body 821 can be wider than the distal body 822. The two-stage reamer can be used to define two differently sized openings in the humerus H, for example, to accommodate the varying diameter of the anchor 108. For example, in some embodiments, the distal body 822 can be configured to create the distal opening DO which receives the finned second portion 296 of the anchor 108. The larger proximal body 821 can be configured to create a larger proximal opening PO which receives the first portion 292 of the anchor 108.

In step 852, the humeral anchor insertion instrument 900 (which may be the same as or different from the instrument 900 shown in FIG. 8A) may be used to insert an appropriately-sized anchor 108 into the resection surface RS of the humerus H. As in FIG. 8A, in a step 853 sizers can be used to test the fit of the anchor 108 into the humerus H. In a step 854, an impactor 818A can be used to press the reverse articular component 180 onto the anchor 108.

Figure 9A:
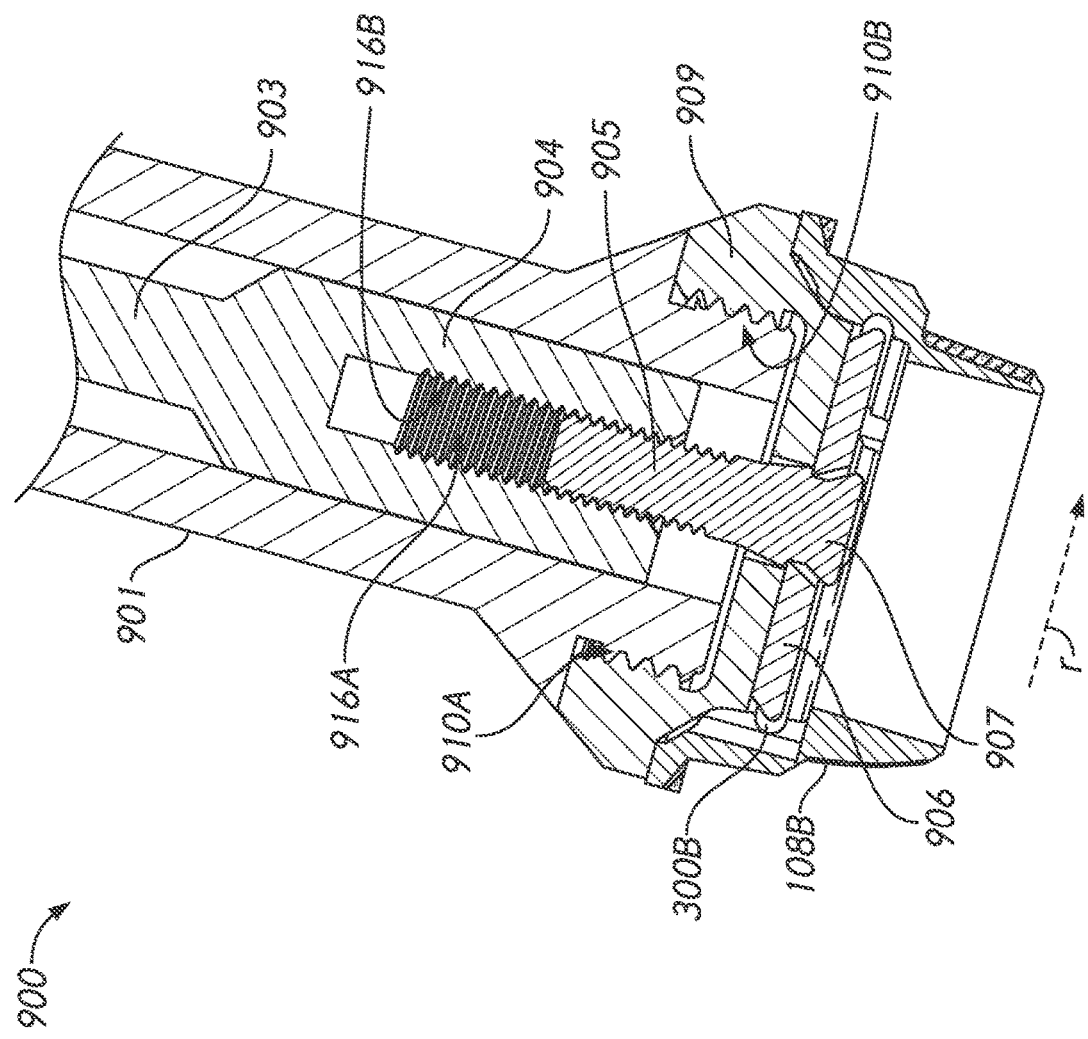
FIG. 9A is schematic cross-sectional view of a portion of a humeral anchor insertion instrument, according to one embodiment.
Figure 9C:
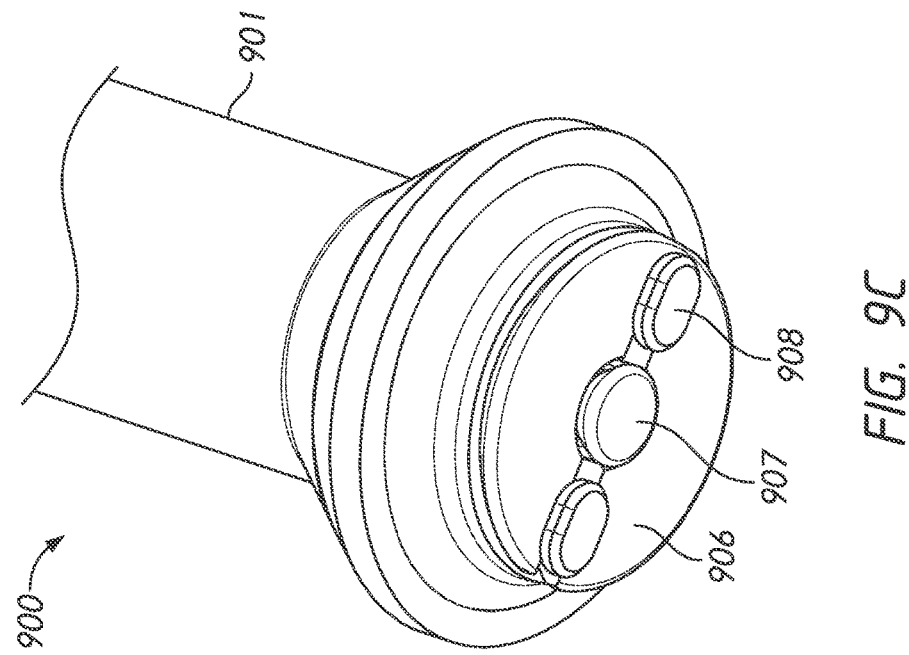
FIG. 9C is an enlarged, schematic perspective view of a distal portion of the instrument of FIG. 9B.
Figure 9B:
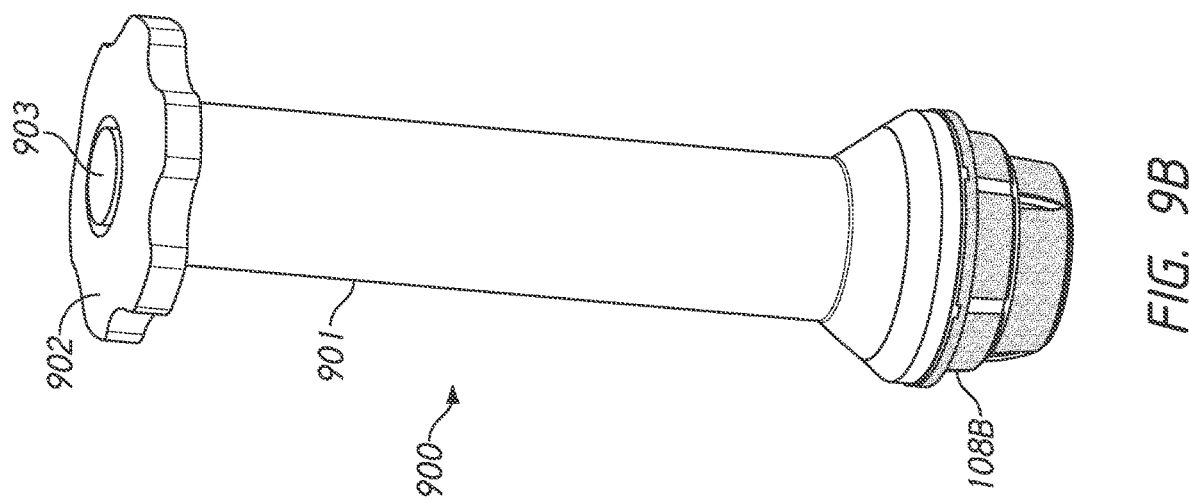
FIG. 9B is a schematic perspective view of the instrument of FIG. 9A.
Figure 9E:
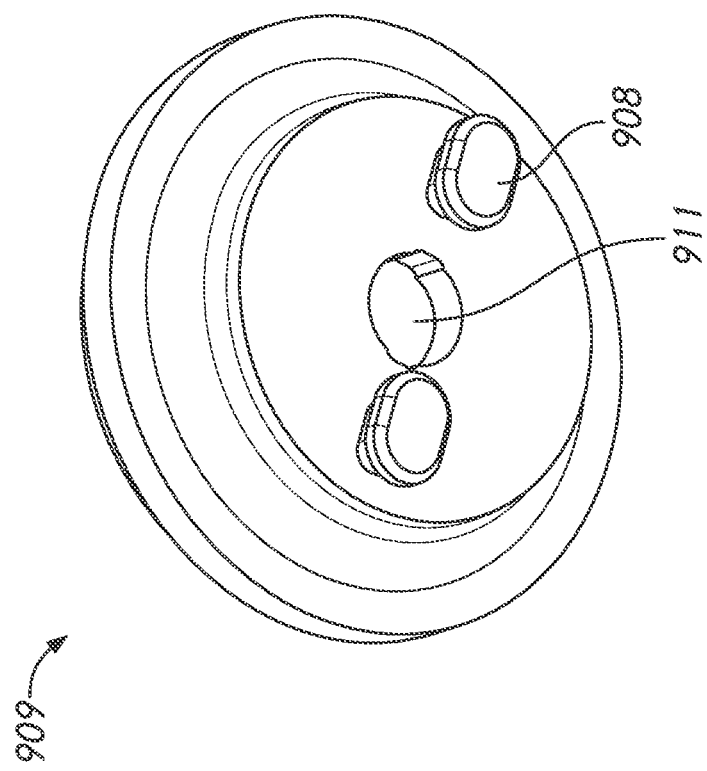
FIG. 9E is a bottom perspective view of the faceplate of FIG. 9D.
Figure 9D:
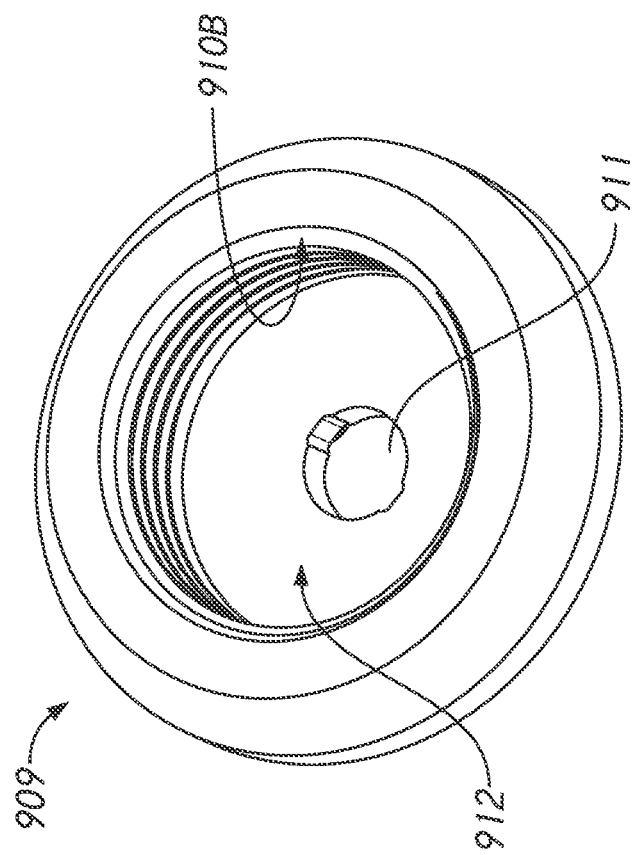
FIG. 9D is a schematic top perspective view of a faceplate for engaging a top, proximal or medial side of the humeral anchor.
Figure 9G:
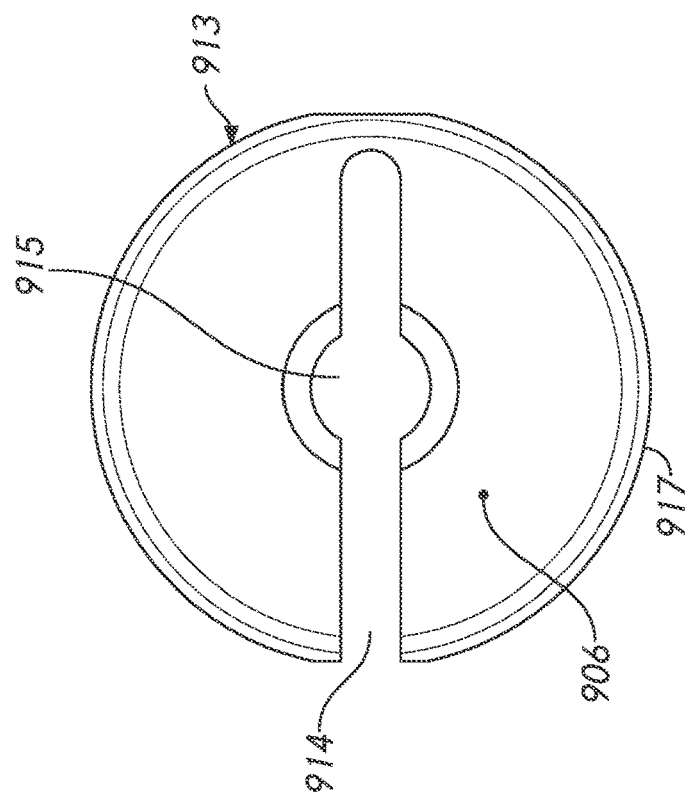
FIG. 9G is a top plan view of an expansion disc 906 of the instrument shown in FIGS. 9A-9C.
Figure 9F:
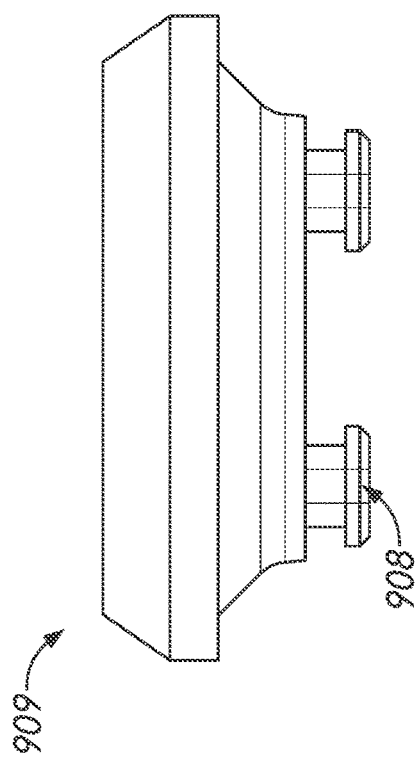
FIG. 9F is a schematic side view of the faceplate.

FIGS. 9A-9G illustrate an embodiment of a humeral anchor insertion instrument 900 comprising an expansion disc 906. The instrument 900 can be configured to reduce or eliminate torque applied to the humeral anchor upon release of the instrument from the anchor. FIG. 9A is schematic cross-sectional view of a portion of the humeral anchor insertion instrument 900, according to one embodiment. FIG. 9B is a schematic perspective view of the instrument 900 of FIG. 9A. FIG. 9C is an enlarged, schematic perspective view of a distal portion of the instrument 900 of FIG. 9B. FIG. 9D is a schematic top perspective view of a faceplate 909 for engaging a top, proximal or medial side of the anchor 108C. FIG. 9E is a bottom perspective view of the faceplate 909 of FIG. 9D. FIG. 9F is a schematic side view of the faceplate 909. FIG. 9G is a top plan view of an expansion disc 906 of the instrument 900.

As explained in connection with FIGS. 8A-8B, the stemless humeral anchors described herein can be inserted into the humerus H with an insertion motion that does not rotate the humeral anchor. It can be important to provide a secure grip on the humeral anchor during insertion, while ensuring that the anchor can be easily released after insertion without the need for applying excessive torque or other forces. Accordingly, the embodiment of FIGS. 9A-9G provide improved instrumentation for inserting humeral anchors into the anatomy and for removing the instrumentation from the anchor after insertion. In the illustrated embodiment, the bowl-shaped anchor 108B is shown in an example insertion configuration, but it should be appreciated that the instrument 900 can be used in conjunction with any of the humeral anchors disclosed herein.

Turning to FIGS. 9A-9C, the instrument 900 can comprise a handle 901 that the clinician can grip during insertion and/or release. A rod 903 can be disposed within a lumen of the handle 901 and can be translate and rotate relative to the handle 901. The rod 903 can be coupled to or formed with a grip 902. The clinician can rotate the grip 902 to impart rotation to the rod 903. As shown in FIG. 9A, a distal portion of the rod 903 can comprise a tubular threaded portion 904 having internal threads 916B. The handle 901 can have a distal portion with external threads 910A configured to threadably engage with corresponding internal threads 910B of the faceplate 909 to mechanically connect the faceplate 909 and the handle 901.

As shown in FIGS. 9D-9F, the faceplate 909 can comprise a central aperture 911 and a cavity 912 sized and shaped to receive the outer dimensions of the handle 901. A bolt 905 can extend through the central aperture 911 of the faceplate 909 and into the threaded portion 904 of the rod 903. Outer threads 916A of the bolt 905 can threadably engage with inner threads 916B of the threaded portion 904 of the rod 903. As shown in FIG. 9A, the distal end of the handle 901 can bear against the upper surface of the faceplate 909.

As shown in FIGS. 9A and 9G, the instrument 900 can further comprise an expansion disc 906 configured to expand radially outward and contract radially inward along a radial direction r. The expansion disc 906 can comprise a central opening 915, a slot 914 that passes through the central opening 915 and defines an outer gap in the disc 906, and a thinned torsional spring section 913. As shown in FIG. 9A, the bolt 905 can further pass through the central opening 915 of the expansion disc 906. A head 907 of the bolt 905 can bear against the distal or back surface of the expansion disc 906. Furthermore, the faceplate 909 can comprise one or a plurality of lugs 908 extending distally from the faceplate 909. The lugs 908 can comprise a thinned portion extending from the faceplate and a wider head at the distal end of the lugs 908. The lugs 908 can extend through the slot 914 of the expansion disc 906 with the wider head engaging the back side of the expansion disc 906.

The expansion disc 906 can be configured to engage the interior surface 212B of the humeral anchor 108B to apply a radially outward gripping force when expanded in a first configuration of the instrument 900 and to disengage from and to not apply a radially outward force on the interior surface 212B of the humeral anchor 108B when in a relaxed or contracted state in a second configuration of the instrument 900. For example, when the anchor 108B is to be inserted into the humerus H, the clinician can rotate the grip 902 to impart rotation to the rod 903. Rotation of the rod 903 can in turn threadably engage with the bolt 905 to draw the head 907 of the bolt 905 proximally. Proximal movement of the bolt 905 can cause the head 907 to bear against the opening 915 to enlargen the slot 914. The thinned torsional hinge portion 913 can enable a reduced torque to cause expansion. An outermost edge 917 of the expansion disc 906 can engage with the groove 300B of the anchor 108B when the expansion disc 906 is suitably expanded in a radially outward direction.

The clinician can insert the anchor 108B with a non-rotational insertion motion of the anchor. Once the anchor 108B is secured to the humerus H, the clinician can release the anchor 108B to remove the instrument by rotating the grip 902 in an opposite direction from what was used during insertion. Such a rotational motion can unthread the bolt 905 from the threaded portion 904 of the rod 903 to cause the bolt 905 to move distally. Distal movement of the bolt 905 can cause the expansion disc 906 to relax and the outermost edge 917 to move radially inward from the groove 300B. Once the outermost edge 917 is outside the groove 300B, the instrument 900 can be removed proximally.

Figure 10A:
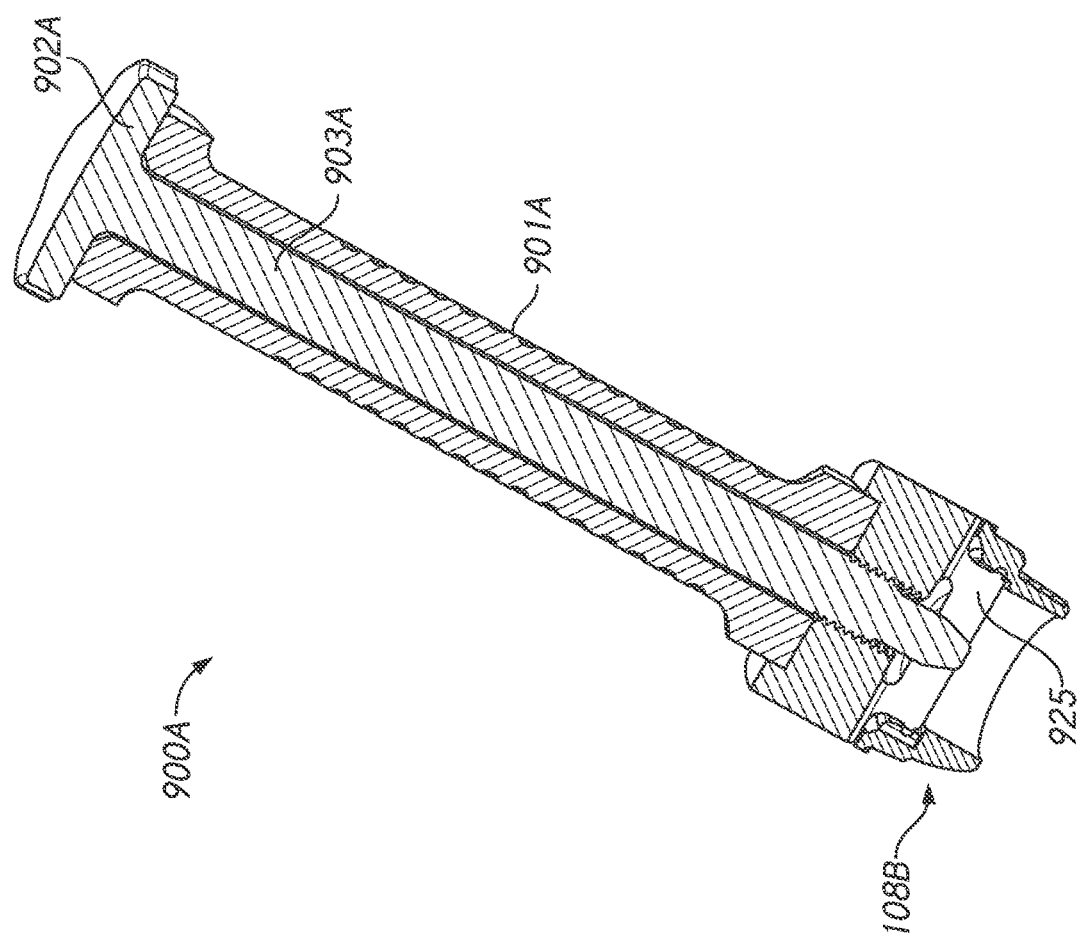
FIG. 10A is a schematic perspective side sectional view of a humeral anchor insertion instrument, according to another embodiment.
Figure 10B:
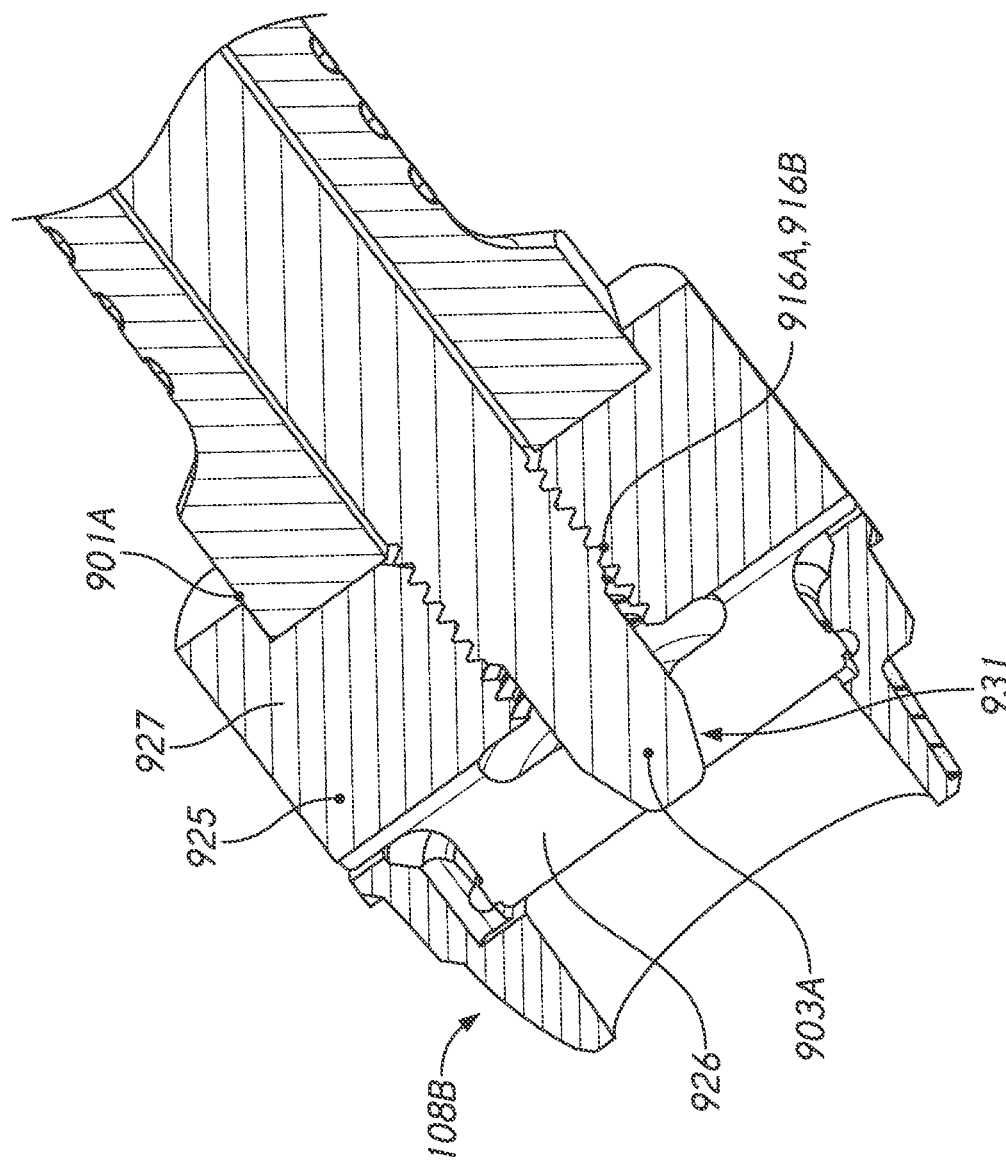
FIG. 10B is an enlarged schematic side sectional view of a distal portion of the instrument of FIG. 10A.
Figure 10D:
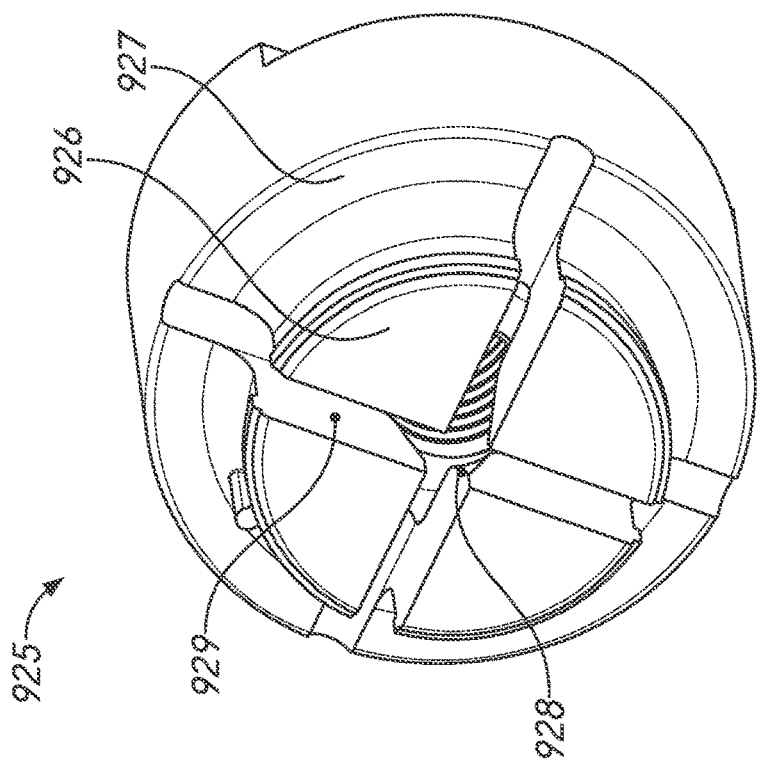
FIG. 10D is a bottom perspective view of the collet of FIG. 10C.
Figure 10C:
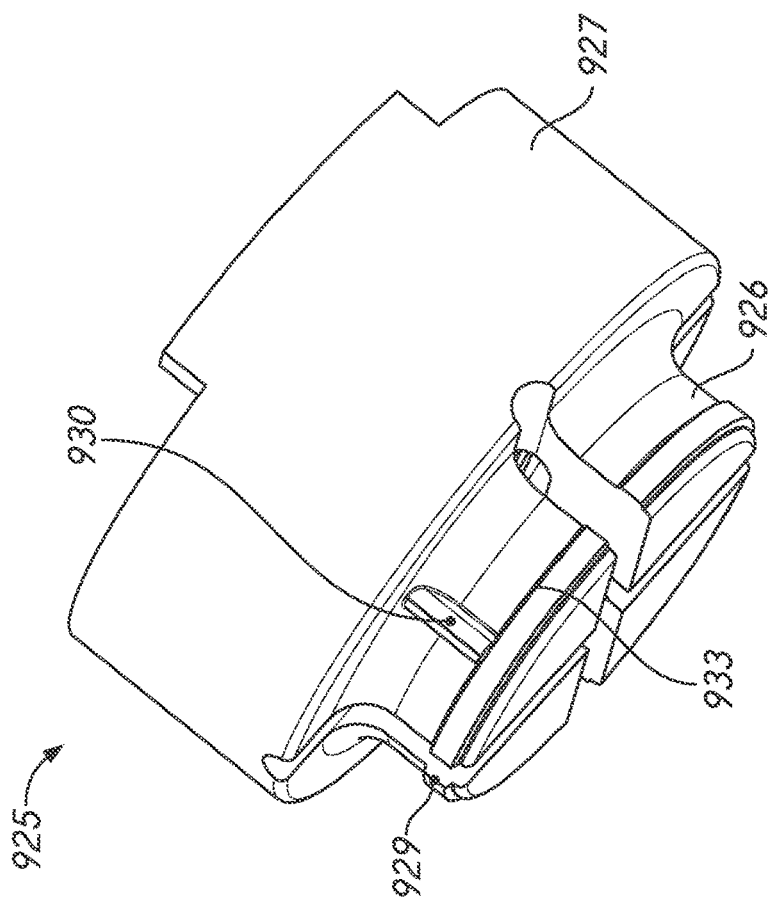
FIG. 10C is a side perspective view of a collet of the instrument of FIG. 10A.

FIGS. 10A-10D illustrate another embodiment of a humeral anchor insertion instrument 900A configured to reduce or eliminate torque applied to the humeral anchor 108B upon release of the instrument 900A from the anchor 108B. Although FIGS. 10A-10D are illustrated in conjunction with the anchor 108B, any of the humeral anchors disclosed herein can be used with the instrument 900A. FIG. 10A is a schematic perspective side sectional view of the instrument 900A. FIG. 10B is an enlarged schematic side sectional view of a distal portion of the instrument 900A. FIG. 10C is a side perspective view of a collet 925 of the instrument 900A. FIG. 10D is a bottom perspective view of the collet 925 of FIG. 10C. Unless otherwise noted, reference numerals in FIGS. 10A-10D may represent components that are the same as or similar to like-numbered components of FIGS. 9A-9G, with the reference numerals appended with the letter "A."

For example, as with the embodiment of FIGS. 9A-9G, the instrument 900A can comprise a handle 901, a rod 903A disposed in the handle 901, and a grip 902A configured to impart rotation to the rod 903A. As shown in FIG. 10B, however, a distal portion of the rod 903A can comprise outer threads 916A configured to engage inner threads 916B of the collet 925. As shown in FIGS. 10B-10D, the collet 925 can comprise a wider proximal portion 927 and a narrower distal portion 926 formed with or coupled to the proximal portion 927. The collet 925 can comprise an opening 928 sized and shaped to receive the distal portion of the rod 903A. Further, one or more slots 929 can extend in a cross-wise pattern through the distal portion 926 and can intersect with the hole 928. Further, one or more anti-rotation recesses 930 can engage with corresponding features on the anchor 108B to limit rotation.

The collet 925 can be configured to engage an interior surface 212B of the humeral anchor 108B to apply a radially outward gripping force when expanded in a first configuration of the instrument 900A and to disengage from and to not apply a radially outward force on the interior surface 212 of the humeral anchor 108B when in a relaxed or contracted state in a second configuration of the instrument 900A. For example, as explained above, it can be important to securely engage the anchor 108B during insertion of the anchor 108B into the humerus H and to provide an easy release of the instrument 900A from the anchor 108B after insertion. During insertion, the clinician can rotate the grip 902A in a first direction to threadably engage the rod 903A with the threaded portion of the collet 925. Distal motion of a tapered surface 931 of the distal end of the rod 903A can engage the opening 928 and slots 929 to cause the collet 925 to expand radially outward. Radial outward expansion of the collet 925 can cause an outermost edge 933 of the distal portion 926 of the collet 925 to be disposed within the groove 300B. The clinician can insert the anchor 300B into the humerus H with a non-rotatable insertion motion.

After inserting the anchor 108B into the humerus H, the clinician can release the instrument 900A from the anchor 108B by rotating the grip 902 in a second direction opposite the first used during insertion. Proximal movement of the rod 903A can retract the tapered surface 931 through the opening 928, causing the collet 925 to relax and contract radially. Once the outermost edge 933 is removed from the groove 300B, the clinician can remove the instrument 900A with proximal movement.

IV. Manufacturing Methods for Humeral Anchors

FIGS. 11A-11C illustrate various components for improving the throughput and quality of manufacturing for the stemless humeral anchors disclosed herein.

The humeral anchors described herein can be manufactured in any suitable way. For example, various additive manufacturing techniques, such as three-dimensional (3D) printing, can be very effective at manufacturing complex three-dimensional shapes, including shapes with cavities, grooves, rounded or angled surfaces, etc. However, the throughput of additive manufacturing techniques is generally quite low. Accordingly, it can be desirable to utilize high quality, high throughput manufacturing techniques for the humeral anchors disclosed herein. Also, 3D printing may not yield a final article with suitable final dimensions, surface finish or other mechanical properties. As such, other manufacturing processes may be combined with 3D printing to obtain a final, finished article. It should be appreciated that FIGS. 11A-11C are illustrated in connection with the manufacture of an anchor 108B, but the techniques and devices disclosed in FIGS. 11A-11B can be used for any of the stemless humeral anchors disclosed herein.

FIG. 11A is a schematic perspective view of a blank die 1001 supporting a blank component 1010 prior to a machining process. FIG. 11B is a schematic side sectional view of the blank die 1001 of FIG. 11A. FIG. 11C is a schematic perspective view of a finished stemless humeral anchor 108B. The die 1001 shown in FIGS. 11A-11B can have an external surface 1014 sized and shaped to have the general contours and tapered surfaces corresponding to complementary interior surfaces 212B of the anchor 108B. For example, the external surface 1014 can include an upper tapered portion and a lower tapered portion that may correspond to the inner tapers of the anchor 108B as described herein. To accommodate accurate and repeatable manufacturing, the blank die 1001 can be formed using an additive manufacturing technique, such as 3D printing.

In one variation the blank die 1001 and the blank component 1010 are both produced in the same additive manufacturing process from an initial layer, e.g., at an outer or proximal end (to the left in FIG. 11A), by adding layers toward the distal end (to the right in FIG. 11A). As the layers are formed on top of the prior layer the die 1001 and the blank component 1010 are formed together.

The blank die 1001 can have a notch 1002 at an outer portion of the blank die 1001 so that a manufacturing system (e.g., a computer numerical control, or CNC, machine) can automatically detect the orientation of the blank die 1001 and the blank component 1010 provided over the external surface 1014 of the blank die 1001. The notch 1002 also provides an engagement or gripping portion for securing the blank die 1001 in a machining apparatus. The blank die 1001 can comprise a central channel 1003 formed along a length of the die 1001 and defined by an inner wall 1012 of the blank die 1001. The notch 1002 can be formed in a first handle portion 1006 at the outer end. A second handle portion 1006' can be provided at the inner or distal end to improve manipulation of the die 1001 during machining. An anti-rotation feature 1005 can be provided at an inner or distal portion of the handle portion 1006' to limit rotation of the die during machining. The anti-rotation feature 1005 and the notch 1002 can enable the blank die 1001 to be securely held during manufacturing.

A CNC machine or other automated manufacturing system can be activated to pattern or connect components onto the exterior surface 214B of the anchor 108B. The use of the blank die 1001 can cause the blank component 1010 to conform to the general geometry of the anchor 108B to enable the anchor to finished without significant additional processing of the exterior surface. FIG. 11C illustrates the final anchor 108B produced using the machining techniques disclosed herein.

In one technique, the blank die 1001 is formed using additive manufacturing. The blank die 1001 is formed such that the external surface 1014 approximates the final exterior surface of the anchor 1008B. In certain techniques, the external surface 1014 is finished, e.g., using turning, milling or lathing. The notch 1002 and the anti-rotation feature 1005 facilitate securing the blank die 1001 in a machining apparatus, e.g. a turning, milling, lathing process, or other similar process. The first and second handle portions 1006, 1006' can be removed after the external surface 1014 has been prepared. The central channel 1003 can be formed to have generally the same shape and size as the internal surface of the anchor 108B. FIG. 11B shows that the central channel 1003 may not have the groove 300B or slots 264B discussed above. These and other features of the interior surface 212B can be formed in a subsequent machining process.

As discussed above, the anchor 108C has a solid wall 311 enclosing a distal end of the cavity 217C. The anchor 108C (and the anchor 108) advantageously are enclosed at the solid wall 311 such that bone matter will be excluded from the interior of the anchor 108C as it is inserted into the humerus bone. The die blank 1001 and the blank component 1010 can comprise a pre-formed article for the anchor 108C (and the anchor 108) by forming a solid transverse wall at or near to the junction of the surface 1014 and the handle 1006'. When the handle 1006' is removed, the solid wall 311 can be provided at the inner or distal end of the blank component 1010. The solid wall 311 can be perforated in some cases while generally enclosing the distal end of the cavity of the anchor 108C (or the anchor 108). For stemless anchors (such as the anchors 108, 108C, 104) that include the solid wall 311 to enclose the anchors, the transverse wall at the junction of the surface 1014 and the handle 1006' can be used to define the solid wall 311, and the anchor can be built up layer-by-layer as described above. Once the exterior surfaces 214 of the anchor are formed, finishing processes can be used but the porous regions and struts and other non-porous regions are formed by in 3D printing process. For stemmed designs, the blank die 1001 can include an elongate stem-shaped profile and, as with the stemless anchors, the stem can be formed along the elongate stem-shaped profile of the die 1001. Still other methods of forming the stemmed anchor may be suitable.

These methods are applicable to the stemless anchors described herein. The approaches apply most directly to the components described herein that are at least partially rotationally symmetric.

Terminology

Although certain embodiments have been described herein, the implants and methods described herein can interchangeably use any articular component, as the context may dictate.

As used herein, the relative terms "proximal" and "distal" shall be defined from the perspective of the implant. Thus, proximal refers to the direction of the articular component and distal refers to the direction of an anchor component, such as a stem of a humeral anchor or a thread or porous surface or other anchoring structure of a stemless anchor when the implant is assembled.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or"

is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "coupling a glenoid guide with the glenoid rim" include "instructing coupling of a glenoid guide with a glenoid rim."

What is claimed is:

1. A stemmed anchor assembly, comprising:
   a humeral anchor that comprises:
      a first end including a collar;
      a second end;
      an interior surface extending between the first end and the second end, the interior surface defining a recess that extends through an entirety of the humeral anchor between the first end and the second end;
      an exterior surface including a first tapered portion extending from the collar to a lateral projection and a second tapered portion extending from the lateral projection to the second end, the lateral projection defining a discontinuity between the first tapered portion and the second tapered portion; and
      a slot extending along the interior surface between the collar and the lateral projection and configured to engage a corresponding ridge of a coupling of a shoulder articular body;
      wherein the recess is configured to secure the coupling of the shoulder articular body directly to the interior surface, and
      the slot has a length that extends between the collar and the lateral projection and a width that extends circumferentially along the interior surface, the length being longer than the width;
   a stem; and
   an adaptor configured for coupling the second end of the humeral anchor to the stem.

2. The stemmed anchor assembly of claim 1, wherein the first end comprises a planar surface and the stem is disposed along a longitudinal axis, the longitudinal axis being disposed at an angle of 135 degrees to the planar surface.

3. The stemmed anchor assembly of claim 1, wherein the first end comprises a planar surface and the stem is disposed along a longitudinal axis, the longitudinal axis being disposed at an angle of 145 degrees to the planar surface.

4. The stemmed anchor assembly of claim 1, wherein an angle between a planar surface and a longitudinal axis of the stem is patient specific.

5. The stemmed anchor assembly of claim 1, wherein a ratio between a diameter of the first end of the humeral anchor and a distal diameter of the stem is patient specific.

6. The stemmed anchor assembly of claim 1, wherein the distance between a longitudinal axis of the humeral anchor and a longitudinal axis of the stem is patient specific.

7. The stemmed anchor assembly of claim 1, wherein the collar of the humeral anchor includes a transverse surface configured to engage a humeral bone layer exposed by resection or other preparation when the humeral anchor is implanted to resist subsidence.

8. The stemmed anchor assembly of claim 1, wherein the interior surface of the humeral anchor comprises a tapered surface for engaging the shoulder articular body.

9. A humeral implant assembly, comprising:
a humeral anchor that comprises:
a first end including a collar;
a second end;
an interior surface extending between the first end and the second end, the interior surface defining a recess that extends through an entirety of the humeral anchor between the first end and the second end;
an exterior surface including a first tapered portion extending from the collar to a lateral projection and a second tapered portion extending from the lateral projection to the second end, the lateral projection defining a discontinuity between the first tapered portion and the second tapered portion; and
at least one slot extending along the interior surface between the collar and the lateral projection; and
a shoulder articular body comprising a locking component, wherein the at least one slot is configured to engage a corresponding ridge of the shoulder articular body;
wherein the recess is configured to secure the locking component of the shoulder articular body directly to the interior surface from the first end of the humeral anchor, and
the at least one slot has a length that extends between the collar and the lateral projection and a width that extends circumferentially along the interior surface, the length being longer than the width.

10. The humeral implant assembly of claim 9, wherein the locking component comprises an undulating ring.

11. The humeral implant assembly of claim 9, wherein the collar of the humeral anchor includes a transverse surface configured to engage a humeral bone layer exposed by resection or other preparation when the humeral anchor is implanted to resist subsidence.

12. The humeral implant assembly of claim 9, wherein the interior surface of the humeral anchor comprises a tapered surface for engaging the shoulder articular body.

13. A Kit, comprising:
a first humeral anchor that comprises:
a first end including a collar;
a second end;
an interior surface extending between the first end and the second end, the interior surface defining a recess that extends through an entirety of the first humeral anchor between the first end and the second end;
an exterior surface including a first tapered portion extending from the collar to a lateral projection and a second tapered portion extending from the lateral projection to the second end, the lateral projection defining a discontinuity between the first tapered portion and the second tapered portion; and
a slot extending along the interior surface between the collar and the lateral projection and configured to engage a corresponding ridge of a coupling of a shoulder articular body;
wherein the recess is configured to secure the coupling of the shoulder articular body directly to the interior surface, and the slot has a length that extends between the collar and the lateral projection and a width that extends circumferentially along the interior surface, the length being longer than the width; and
a second humeral anchor comprising an anchor portion and a stem, wherein the anchor portion comprises:
a first end including a second collar and a second end;
a second interior surface extending between the first end of the anchor portion and the second end of the anchor portion, the second interior surface defining a second recess that extends through an entirety of the anchor portion between the first end of the anchor portion and the second end of the anchor portion;
a second exterior surface including a first tapered portion extending from the second collar to a second lateral projection and a second tapered portion extending from the second lateral projection to the second end of the anchor portion, the second lateral projection defining a discontinuity between the first tapered portion of the second exterior surface and the second tapered portion of the second exterior surface; and
a second slot extending along the second interior surface between the second collar and the second lateral projection and configured to engage a corresponding ridge of a coupling of the shoulder articular body;
wherein the second recess is configured to secure the coupling of the shoulder articular body directly to the second interior surface, and
the second slot has a length that extends between the second collar and the second lateral projection and a width that extends circumferentially along the second interior surface, the length being longer than the width;
wherein the second end of the anchor portion is coupled to the stem; and
wherein the anchor portion and the first humeral anchor are identical.

14. A kit comprising:
a first humeral implant assembly, comprising:
a first humeral anchor that comprises:
a first end including a collar;
a second end;
an interior surface extending between the first end and the second end, the interior surface defining a recess that extends through an entirety of the first humeral anchor between the first end and the second end;
an exterior surface including a first tapered portion extending from the collar to a lateral projection and a second tapered portion extending from the lateral projection to the second end, the lateral projection defining a discontinuity between the first tapered portion and the second tapered portion; and
at least one slot extending along the interior surface between the collar and the lateral projection; and a first shoulder articular body comprising a locking component, wherein the at least one slot is configured to engage a corresponding ridge of the first shoulder articular body;

wherein the recess is configured to secure the locking component of the first shoulder articular body directly to the interior surface from the first end of the first humeral anchor, and the at least one slot has a length that extends between the collar and the lateral projection and a width that extends circumferentially along the interior surface, the length being longer than the width; and a second humeral implant assembly, comprising:
a second humeral anchor that comprises:
a first end including a second collar and a second end;
a second interior surface extending between the first end and the second end of the second humeral anchor, the second interior surface defining a second recess that extends through an entirety of the second humeral anchor between the first end of the second humeral anchor and the second end of the second humeral anchor;
a second exterior surface including a first tapered portion extending from the second collar to a second lateral projection and a second tapered portion extending from the second lateral projection to the second end of the second humeral anchor, the second lateral projection defining a discontinuity between the first tapered portion of the second exterior surface and the second tapered portion of the second exterior surface; and
at least one second slot extending along the second interior surface between the second collar and the second lateral projection; and a second shoulder articular body comprising a locking component, wherein the at least one second slot is configured to engage a corresponding ridge of the second shoulder articular body;

wherein the second recess is configured to secure the locking component of the second shoulder articular body directly to the second interior surface from the first end of the second humeral anchor, and the at least one second slot has a length that extends between the second collar and the second lateral projection and a width that extends circumferentially along the second interior surface, the length being longer than the width;

wherein the locking component of the first humeral implant assembly and the locking component of the second humeral implant assembly are configured to provide uniform insertion force during advancement of the first and second shoulder articular bodies into their respective humeral anchor.

* * * * *